US008841090B2

(12) United States Patent
Zhang et al.

(10) Patent No.: US 8,841,090 B2
(45) Date of Patent: *Sep. 23, 2014

(54) L-ARABINOSE FERMENTING YEAST

(71) Applicant: Alliance for Sustainable Energy, LLC, Golden, CO (US)

(72) Inventors: Min Zhang, Lakewood, CO (US); Arjun Singh, Lakewood, CO (US); Pirkko Suominen, Minnetonka, MN (US); Eric Knoshaug, Golden, CO (US); Mary Ann Franden, Centennial, CO (US); Eric Jarvis, Boulder, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/744,023

(22) Filed: Jan. 17, 2013

(65) Prior Publication Data

US 2013/0189788 A1    Jul. 25, 2013

Related U.S. Application Data

(62) Division of application No. 12/909,523, filed on Oct. 21, 2010, now Pat. No. 8,372,626, which is a division of application No. 11/912,493, filed as application No. PCT/US2007/064330 on Mar. 19, 2007, now Pat. No. 7,846,712.

(60) Provisional application No. 60/810,562, filed on Jun. 1, 2006.

(51) Int. Cl.
*C12P 21/04* (2006.01)
*C12N 15/81* (2006.01)
*C12P 7/08* (2006.01)

(52) U.S. Cl.
CPC .. *C12N 15/81* (2013.01); *C12P 7/08* (2013.01)
USPC ... 435/71.1; 435/69.1; 435/254.1; 435/320.1; 536/23.1; 536/23.7

(58) Field of Classification Search
CPC ........ C12N 15/00; C12N 15/10; C12N 15/12; C12N 15/63; C12N 15/64; C12N 15/81; C12N 1/14; C12N 1/15; C12N 1/16; C12Q 1/68; C12P 21/06; C12P 21/04; C07H 21/00; C07H 21/04
USPC ......... 435/69.1, 71.1, 254.1, 320.1; 536/23.1, 536/23.7
See application file for complete search history.

(56) References Cited

U.S. PATENT DOCUMENTS

| 5,272,071 A | 12/1993 | Chappel |
| 5,965,408 A | 10/1999 | Short |
| 7,846,712 B2 | 12/2010 | Zhang et al. |
| 8,372,626 B2 | 2/2013 | Zhang et al. |
| 2003/0186402 A1 | 10/2003 | Londesborough et al. |
| 2005/0142648 A1 | 6/2005 | Boles et al. |
| 2005/0260705 A1 | 11/2005 | Better |

FOREIGN PATENT DOCUMENTS

WO    9931241    6/1999

OTHER PUBLICATIONS

Altschul, "Basic Local Alignment Search Tool", J. Mol. Biol., 1990, pp. 403-410.
Alves-Araujo, "Cloning and Characterization of the MAL11 Gene Encoding from *Torulaspora delbrueckii*", FEMS Yeast Research, 2004, pp. 467-476.
Arnold, "When Blind is Better: Protein Design by Evolution", Nature Biotechnology, Jul. 1998, vol. 16, pp. 617-618.
Author Unknown, GenomeWalker™ Universal Kit User Manual, Clontech Laboratories, Inc., Published Apr. 25, 2007, Version PR742236 pp. 1-30.
Barnett, "The Utilization of Sugars by Yeasts", School of Biological Sciences, 1976, pp. 125-234.
Becker, "A Modified *Saccharomyces cerevisiae* Strain that Consumes L-Arabinose and Produces Ethanol", Applied and Environmental Microbiology, Jul. 2003, vol. 69, No. 7, pp. 4144-4150.
Billard, "Glucose Uptake in *Kluyveromyces lactis*: Role of the HGT1 Gene in Glucose Transport", J. Bacteriology, Oct. 1996, vol. 178, No. 20, pp. 5860-5866.
Bowie, "Deciphering the Message in Protein Sequences: Tolerance to Amino Acid Substitutions", Science, 1990, vol. 247, pp. 1306-1310.
Colbere-Garapin, "A New Dominant Hybrid Selective Marker for Higher Eukaryotic Cells", J. Mol. Biol., 1981, pp. 1-14.
Cosman, "ULBPs, Novel MHC Class . . . Through the NKG2D Receptor", Immunity, 2001, vol. 14, pp. 123-133.
Crameri, "DNA shuffling of a Family of Genes from Diverse Species Accelerates Directed Evolution", Nature, 1998, vol. 391, pp. 288-291.
Day, "Characterization of the Putative Maltose Transporters Encoded by YDL247w and YJRI60c", Yeast, 2002, 1015-1027.
Deanda, "Development of an Arabinose-Fermenting *Zymomonas mobilis* Strain by Metabolic Pathway Engineering", Applied and Environmental Microbiology, 1996, pp. 4465-4470.
Dujon, "Genome Evolution in Yeasts", Nature, 2004, vol. 430, pp. 35-44.
Hellinga, "Computational Protein Engineering", Nature Structural Biology, 1998, vol. 5, pp. 525-527.

(Continued)

*Primary Examiner* — Jennifer Graser
(74) *Attorney, Agent, or Firm* — John C. Stolpa

(57) ABSTRACT

An L-arabinose utilizing yeast strain is provided for the production of ethanol by introducing and expressing bacterial araA, araB and araD genes. L-arabinose transporters are also introduced into the yeast to enhance the uptake of arabinose. The yeast carries additional genomic mutations enabling it to consume L-arabinose, even as the only carbon source, and to produce ethanol. A yeast strain engineered to metabolize arabinose through a novel pathway is also disclosed. Methods of producing ethanol include utilizing these modified yeast strains.

10 Claims, 23 Drawing Sheets

(56) References Cited

OTHER PUBLICATIONS

Hespell, "Extraction and Characterization of Hemicellulose from the Corn Fiber Produced by Corn Wet-Milling Processes", J. Agric. food Chem., 1998, vol. 46, pp. 2615-2619.
Hill, "DMSO-Enhanced Whole Cell Yeast Transformation", Nucleic Acids Research, 1991, vol. 19, p. 5791.
Hofmann, "A Database of Membrane Spanning Protein Segments", Konferenz der Gesellschaft fur Biologische Chemie, 1993, vol. 374, p. 166.
Kao, "Genetics of Somatic Mammalian Cells . . . in Chinese Hamster Cells", Genetics, 1968, vol. 60, pp. 1275-1281.
Kotter, "Isolation and Characterization of Transformant", Current Genetics, 1990, vol. 18, pp. 493-500.
Kruckeberg, "The Hexose Transporter Family of *Saccharomyces cerevisiae*", Arch. Microbiol., 1996, 283-292, vol. 166.
Landschulz, "The Leucine Zipper: A Hypothetical Structure . . . DNA Binding Proteins", Science, 1988, 1759-1764, vol. 240.
Luckow, "Trends in the Development of Baculovirus Expression Vectors", Bio/Technology, 1988, 47-55, vol. 6.
McMillan, "Arabinose Utilization b Xylose-Fermenting Yeasts and Fungi", Applied Biochemistry and Biotechnology,1994, 569-584, vol. 45/46.
Mulligan, "Selection for Animal Cells That Express for Xanthine-Guanine Phosphoribosyltransferase", Proceedings of the National Academy of Sciences of the United States of America, 1981, 2072-2076, vol. 78.
O'Hare, "Transformation of Mouse Fibroblasts to . . . Dihydrofolate Reductase", Proc. Natl. Acad. Sci, 1981, 1527-1531, vol. 78.
Ostergaard, et al., "Metabolic Engineering of *Saccharomyces cerevisiae*", Microbiology and Molecular Biology Reviews, Mar. 2000, vol. 64, No. 1, pp. 34-50.
Pina, "Ffz1, A New Transporter Specific for Fructose from *Zygosaccharomyces bailii*", Microbiology, 2004, 2429-2433.
Richard, et al., "The Missing Link in the Fungal L-Arabinose Catabolic Pathway, Identification of the L-Xyulose Reductase Gene", Biochemistry, 2002, vol. 41, pp. 6432-6437.
Saha, et al., Production of L-arabitol for L-arabinose by *candida entomaea* and *Pichia guilliermondii*, Applied Microbiology and Biotechnology, Apr. 1996, vol. 45, No. 3, pp. 299-306.
Saitou, The Neighbor-Joining Method: A Method for Reconstructing Phylogenetic Trees, Mol. Biol. Evol . 1987, 406-425.
Santerre, "Expression of Prokaryotic Genes for Hygromycin . . . in Mouse L Cells", Gene, 1984, 147-156.
Sedlak, "Expression of *E. coli* araBAD Operon . . . in *Saccharomyces cerevisiae*", Enzyme and Microbial Technology, 2001, 16-24.
Segal, "Toward Controlling Gene Expression Target Sequences", Proc Natl. Acad. Sci., 1999, 2758-2763, vol. 96.
Shiraishi, "Effect of Surface Modification Using Various Acids on Electrodeposition of Lithium", Journal of Applied Electrochemistry, 1995, 584-591.
Smith, "Comparison of Biosequences", Advances in Applied Mathematics, 1981, 482-489.
Stambuk, "d-Xylose Transport by *Candida succiphila* and *Kluyveromyces marxianus*", Applied Biochemistry and Biotechnology, 2003, 255-263, vol. 105-108.
Tietz, "Determination of Alcohols by Gas Chromatography", Fundamentals of Clinical Chemistry, 1976, 1110-1111.
Van Den Burg, "Engineering an Enzyme to Resist Boiling", Proc. Natl. Acad. Sci., 1998, 2056-2060, vol. 95.
Wahlbom "Furfural, 5 Hydroxymethyl Furfural . . . in Recombinant *Saccharomyces cerevisiae*", Biotechnology and Bioengineering, 2002, 172-178, vol. 78.
Weierstall, "Cloning and Characterization of Three Genes of the Yeast *Pichia stipitis*", Molecular Microbiology,1999, 871-883.
Wigler, "Transformation of Mammalian Cells with an Amplifiable Dominant-Acting Gene", Proc. Natl. Acad. Sci, 1980, 3567-3570, vol. 77.
Zhang, Metabolic Engineering of a Pentose Metabolism Pathway in Ethanologenic *Zymomonas mobilis*, Science,1995, 240-243, vol. 267.
Zhao, "Molecular Evolution by Staggered Extension Process (StEP) in Vitro Recombination", Nature Biotechnology, 1998, 258-261, vol. 16.
International Search Report and Written Opinion of the International Searching Authority dated Dec. 11, 2007, for International Application No. PCT/US07/64330.
International Preliminary Report on Patentability for International (PCT) Application No. PCT/US07/64330, issued Dec. 3, 2008.
International Search Report and Written Opinion of the International Searching Authority dated Dec. 11, 2007, for International Application No. PCT/US07/64418.

FIG. 2

```
SEQ ID No4: 1   M   A   Y   E   D   K   L   V   A   P   A   L   K   F   R   N   F   L   D   K
SEQ ID No3: 1   ATGGCTTACGAGGACAAACTAGTGGCTCCGGCCTTGAAGTTTAGAAACTTTCTTGACAAA
            21  T   P   N   I   Y   N   P   Y   I   I   S   I   I   S   C   I   A   G   M   M
            61  ACTCCCAATATCTACAATCCATATATCATTTCTATAATCTCGTGCATTGCGGGTATGATG
            41  F   G   F   D   I   S   S   M   S   A   F   V   S   L   P   A   Y   V   N   Y
            121 TTCGGTTTTGATATTTCTTCAATGTCAGCGTTTGTCAGTTTACCAGCATACGTGAATTAT
            61  F   D   T   P   S   A   V   I   Q   G   F   I   T   S   A   M   A   L   G   S
            181 TTCGATACACCTTCAGCAGTGATTCAAGGATTTATCACATCTGCCATGGCTTTGGGTTCA
            81  F   F   G   S   I   A   S   A   F   V   S   E   P   F   G   R   R   A   S   L
            241 TTTTTCGGGTCAATTGCTTCTGCGTTTGTGTCTGAGCCATTTGGAAGACGAGCTTCCTTA
            101 L   T   C   S   W   F   W   M   I   G   A   A   I   Q   A   S   S   Q   N   R
            301 CTAACTTGTTCGTGGTTTTGGATGATAGGAGCAGCCATCCAAGCGTCTTCGCAGAACCGA
            121 A   Q   L   I   I   G   R   I   I   S   G   F   G   V   G   F   G   S   S   V
            361 GCTCAATTGATTATTGGTCGGATTATATCTGGATTTGGGGTTGGTTTCGGGTCGTCTGTG
            141 A   P   V   Y   G   S   E   M   A   P   R   K   I   R   G   R   I   G   G   I
            421 GCTCCCGTATATGGCTCCGAGATGGCACCTAGAAAAATTAGAGGAAGAATTGGTGGAATT
            161 F   Q   L   S   V   T   L   G   I   M   I   M   F   F   I   S   Y   G   T   S
            481 TTTCAATTATCTGTCACCCTCGGTATCATGATTATGTTCTTCATAAGTTACGGAACTTCT
            181 H   I   K   T   A   A   A   F   R   L   A   W   A   L   Q   I   I   P   G   L
            541 CATATTAAGACTGCGGCAGCTTTCAGGTTAGCCTGGGCACTCCAGATCATTCCTGGACTC
            201 L   M   C   I   G   V   F   F   I   P   E   S   P   R   W   L   A   K   Q   G
            601 CTCATGTGTATTGGTGTCTTCTTTATTCCAGAATCTCCTAGATGGTTGGCCAAACAAGGT
            221 H   W   D   E   A   E   I   I   V   A   K   I   Q   A   K   G   D   R   E   N
            661 CACTGGGACGAAGCCGAAATCATTGTAGCCAAAATTCAAGCCAAAGGAGATCGAGAAAAT
            241 P   D   V   L   I   E   I   S   E   I   K   D   Q   L   M   V   D   E   N   A
            721 CCCGATGTTTTGATTGAAATTTCGGAAATAAAAGACCAATTGATGGTTGACGAGAATGCC
            261 K   A   F   T   Y   A   D   L   F   S   K   K   Y   L   P   R   T   I   T   A
            781 AAAGCCTTTACCTATGCTGACTTGTTTTCGAAAAAATATCTTCCCAGAACCATCACAGCC
            281 M   F   A   Q   I   W   Q   Q   L   T   G   M   N   V   M   M   Y   Y   I   V
            841 ATGTTCGCTCAAATCTGGCAACAATTGACAGGAATGAATGTCATGATGTACTATATCGTT
            301 Y   I   F   E   M   A   G   Y   G   G   N   G   V   L   V   S   S   T   I   Q
            901 TACATTTTCGAAATGGCTGGCTACGGTGGAAATGGAGTGTTGGTATCATCGACAATTCAG
            321 Y   V   I   F   V   V   V   T   F   V   S   L   F   F   L   D   K   F   G   R
            961 TACGTTATCTTTGTCGTTGTTACATTTGTCTCATTATTCTTTTTGGACAAATTTGGAAGA
            341 R   K   I   L   L   V   G   A   A   S   M   M   T   W   Q   F   A   V   A   G
            1021 AGAAAAATTTTACTTGTCGGAGCAGCTTCCATGATGACCTGGCAGTTTGCAGTGGCAGGG
            361 I   L   A   R   Y   S   V   P   Y   D   L   S   D   T   V   K   I   K   I   P
            1081 ATCTTGGCCAGGTACTCGGTCCCGTACGATCTCAGCGATACTGTCAAAATTAAAATTCCT
            381 D   N   H   K   S   A   A   K   G   V   I   A   C   C   Y   L   F   V   A   S
            1141 GACAATCACAAATCGGCTGCAAAAGGTGTCATTGCATGCTGCTATCTTTTCGTAGCATCG
            401 F   G   F   S   W   G   V   G   I   W   L   Y   C   S   E   V   W   G   D   S
            1201 TTCGGATTTTCCTGGGGAGTTGGTATCTGGTTATACTGCTCTGAAGTCTGGGGAGACTCA
            421 Q   S   R   Q   R   G   A   A   V   S   T   A   S   N   W   I   F   N   F   A
            1261 CAATCGAGACAGAGAGGAGCCGCTGTGTCAACTGCTTCAAATTGGATTTTCAATTTTGCG
            441 L   A   M   F   T   P   S   S   F   K   N   I   T   W   K   T   Y   C   I   Y
            1321 CTCGCCATGTTCACACCATCTTCGTTTAAAAATATCACCTGGAAGACATACTGTATTTAT
            461 A   T   F   C   A   C   M   F   I   H   V   F   F   F   F   P   E   T   K   G
            1381 GCCACTTTCTGCGCATGTATGTTCATCCATGTGTTCTTCTTCTTCCCAGAAACCAAGGGG
            481 K   R   L   E   E   I   A   Q   I   W   E   E   K   I   P   A   W   K   T   T
            1441 AAGCGCTTGGAAGAAATTGCTCAAATTTGGGAAGAAAAAATTCCAGCTTGGAAAACCACC
            501 N   W   Q   P   H   V   P   L   L   S   D   H   E   L   A   E   K   I   N   A
            1501 AACTGGCAACCTCATGTTCCTTTGTTGTCGGACCACGAACTTGCGGAAAAGATCAATGCC
            521 E   H   V   E   N   V   N   S   R   E   Q   S   D   D   E   K   S   Q   V   *
            1561 GAACATGTGGAGAACGTGAATTCTAGGGAACAATCGGATGACGAGAAGTCGCAGGTATAA
```

FIG. 7

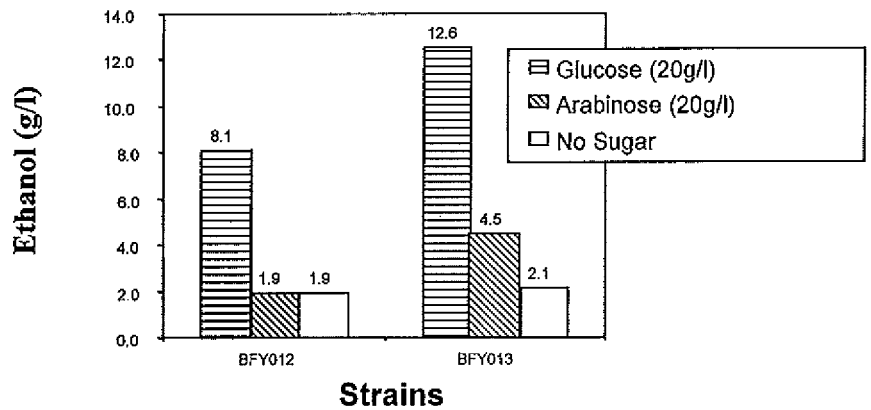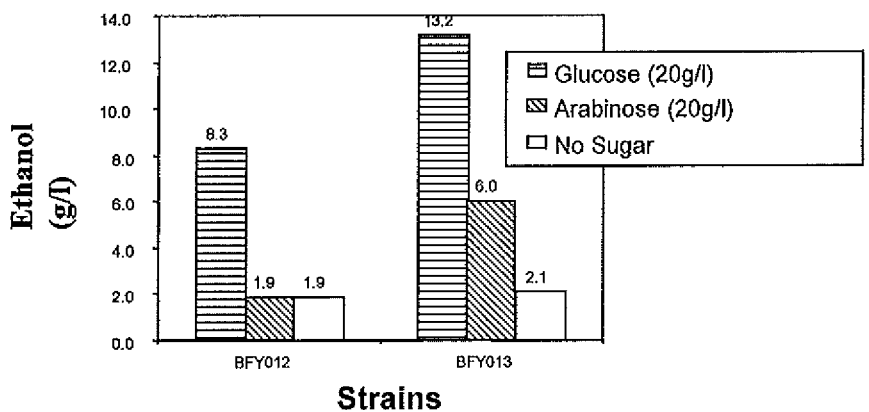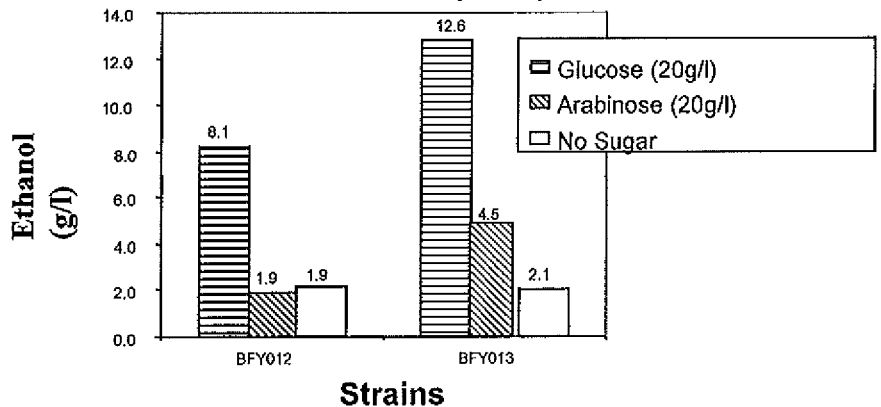
FIG. 16

SEQUENCE LISTING

```
<160> NUMBER OF SEQ ID NOS: 6

<210> SEQ ID NO 1
<211> LENGTH: 1671
<212> TYPE: DNA
<213> ORGANISM: Kluyveromyces marxianus
<220> FEATURE:
<221> NAME/KEY: CDS
<222> LOCATION: (1)..(1668)

<400> SEQUENCE: 1 atg act tta aaa gat aaa cta ttg ctc cgc aat atc gaa ttc aag gga        48
Met Thr Leu Lys Asp Lys Leu Leu Leu Arg Asn Ile Glu Phe Lys Gly
1               5                   10                  15 act ttc tat gcg aag ttc ccg caa att cac aac att tac gca atc ggt        96
Thr Phe Tyr Ala Lys Phe Pro Gln Ile His Asn Ile Tyr Ala Ile Gly
            20                  25                  30
```

-continued

| | |
|---|---|
| gtg att tcg tgt ata tct ggt ctc atg ttt ggt ttc gat atc tct tca<br>Val Ile Ser Cys Ile Ser Gly Leu Met Phe Gly Phe Asp Ile Ser Ser<br>35            40            45 | 144 |
| atg tct tcc atg atc ggt act gaa act tac aaa aaa tat ttt gac cat<br>Met Ser Ser Met Ile Gly Thr Glu Thr Tyr Lys Lys Tyr Phe Asp His<br>50            55            60 | 192 |
| cca aaa tcc att acc caa ggt ggt atc acc gcg tca atg tcc ggt ggt<br>Pro Lys Ser Ile Thr Gln Gly Gly Ile Thr Ala Ser Met Ser Gly Gly<br>65            70            75            80 | 240 |
| tcc ttc tta ggc tct tta ctc tct cct gct att tcc gat acc ttt ggc<br>Ser Phe Leu Gly Ser Leu Leu Ser Pro Ala Ile Ser Asp Thr Phe Gly<br>85            90            95 | 288 |
| aga aaa gtg tcg ttg cac att tgt gcc gtc ttg tgg atc gtc gga tgc<br>Arg Lys Val Ser Leu His Ile Cys Ala Val Leu Trp Ile Val Gly Cys<br>100           105           110 | 336 |
| att ttg caa agt gct gcc caa gac caa cca atg cta atc gct ggc cgt<br>Ile Leu Gln Ser Ala Ala Gln Asp Gln Pro Met Leu Ile Ala Gly Arg<br>115           120           125 | 384 |
| gtt atc gca ggg ttg ggt atc ggg ttc ggc tct ggt tct gct cca att<br>Val Ile Ala Gly Leu Gly Ile Gly Phe Gly Ser Gly Ser Ala Pro Ile<br>130           135           140 | 432 |
| tac tgt tct gaa atc tcc cca cca aag gtt aga ggc ttg atc acc ggt<br>Tyr Cys Ser Glu Ile Ser Pro Pro Lys Val Arg Gly Leu Ile Thr Gly<br>145           150           155           160 | 480 |
| ctt ttc cag ttc tct atc act gtt ggt att atg att ctc ttc tac gtt<br>Leu Phe Gln Phe Ser Ile Thr Val Gly Ile Met Ile Leu Phe Tyr Val<br>165           170           175 | 528 |
| ggt tac ggg tgc cac ttc ctc agt ggt aat ctt tca ttc aga ttg act<br>Gly Tyr Gly Cys His Phe Leu Ser Gly Asn Leu Ser Phe Arg Leu Thr<br>180           185           190 | 576 |
| tgg ggt ttg caa gtt atc cca gga ttt gtg ttg ctg tcg ggt gtc cta<br>Trp Gly Leu Gln Val Ile Pro Gly Phe Val Leu Leu Val Gly Val Leu<br>195           200           205 | 624 |
| ttc ttg cca gaa tcc cca cgt tgg ttg gct aac cac gac cgt tgg gaa<br>Phe Leu Pro Glu Ser Pro Arg Trp Leu Ala Asn His Asp Arg Trp Glu<br>210           215           220 | 672 |
| gaa act gag tca atc gtc gcc aag gtc gtc gcc aag ggt aac gta gac<br>Glu Thr Glu Ser Ile Val Ala Lys Val Val Ala Lys Gly Asn Val Asp<br>225           230           235           240 | 720 |
| gat gaa gaa gtc aag ttc caa ttg gaa gaa att aaa gag cag gtg att<br>Asp Glu Glu Val Lys Phe Gln Leu Glu Glu Ile Lys Glu Gln Val Ile<br>245           250           255 | 768 |
| ctt gat gct gcc gcc aag aac ttc tcc ttc aag gat ttg cta aga cca<br>Leu Asp Ala Ala Ala Lys Asn Phe Ser Phe Lys Asp Leu Leu Arg Pro<br>260           265           270 | 816 |
| aag acc aga aag aag ctc ttt gtt ggt gtg tgt gct caa atg tgg caa<br>Lys Thr Arg Lys Lys Leu Phe Val Gly Val Cys Ala Gln Met Trp Gln<br>275           280           285 | 864 |
| caa ttg tgt ggt atg aac gtt atg atg tac tac att gtg tac gtc ttt<br>Gln Leu Cys Gly Met Asn Val Met Met Tyr Tyr Ile Val Tyr Val Phe<br>290           295           300 | 912 |
| aac atg gct ggt tac act ggt aac acc aac ttg gtt gca tct tcc att<br>Asn Met Ala Gly Tyr Thr Gly Asn Thr Asn Leu Val Ala Ser Ser Ile<br>305           310           315           320 | 960 |
| caa tac gtc ttg aac gtg cta atg act ttc cct gca cta ttc tta atc<br>Gln Tyr Val Leu Asn Val Leu Met Thr Phe Pro Ala Leu Phe Leu Ile<br>325           330           335 | 1008 |
| gat aaa gtc ggt aga aga cct gtc ttg atc gtt ggt ggt att ttc atg<br>Asp Lys Val Gly Arg Arg Pro Val Leu Ile Val Gly Gly Ile Phe Met<br>340           345           350 | 1056 |

| ttc aca tgg ttg ttc gct gtc gct ggt ttg ttg gca tca tat tcc gtc | 1104 |
| Phe Thr Trp Leu Phe Ala Val Ala Gly Leu Leu Ala Ser Tyr Ser Val | |
|   355               360               365 | |

| cca gct cca aat ggt gtt aac ggt gat gat act gtc aca atc aga atc | 1152 |
| Pro Ala Pro Asn Gly Val Asn Gly Asp Asp Thr Val Thr Ile Arg Ile | |
| 370               375               380 | |

| cca gac aag cac aag tcc gcc gct aag ggt gtc att gca tgt tca tac | 1200 |
| Pro Asp Lys His Lys Ser Ala Ala Lys Gly Val Ile Ala Cys Ser Tyr | |
| 385               390               395               400 | |

| ttg ttc gtc tgc tct ttc gct cca acc tgg ggt att ggt atc tgg att | 1248 |
| Leu Phe Val Cys Ser Phe Ala Pro Thr Trp Gly Ile Gly Ile Trp Ile | |
|           405               410               415 | |

| tac tgt tcc gaa att ttc aac aac atg gaa aga gcc aag ggt tcc tct | 1296 |
| Tyr Cys Ser Glu Ile Phe Asn Asn Met Glu Arg Ala Lys Gly Ser Ser | |
|               420               425               430 | |

| gtg gct gct gct acc aac tgg gca ttc aac ttc gct ttg gcg atg ttc | 1344 |
| Val Ala Ala Ala Thr Asn Trp Ala Phe Asn Phe Ala Leu Ala Met Phe | |
|               435               440               445 | |

| gtc cca tct gca ttc aag aac atc tca tgg aaa aca tac atc gtc ttt | 1392 |
| Val Pro Ser Ala Phe Lys Asn Ile Ser Trp Lys Thr Tyr Ile Val Phe | |
| 450               455               460 | |

| ggt gtc ttt tca gtt gca ttg act gtc caa acc tac ttc atg ttc cca | 1440 |
| Gly Val Phe Ser Val Ala Leu Thr Val Gln Thr Tyr Phe Met Phe Pro | |
| 465               470               475               480 | |

| gaa act aga ggt aag acc ttg gaa gaa atc gac caa atg tgg gtc gac | 1488 |
| Glu Thr Arg Gly Lys Thr Leu Glu Glu Ile Asp Gln Met Trp Val Asp | |
|               485               490               495 | |

| aac atc cca gcc tgg aag act agc agc tac atc cca caa ttg cct atc | 1536 |
| Asn Ile Pro Ala Trp Lys Thr Ser Ser Tyr Ile Pro Gln Leu Pro Ile | |
|               500               505               510 | |

| atc gaa gat gaa ttt ggt aac aag ttg ggt ttg ttg ggt aac cca caa | 1584 |
| Ile Glu Asp Glu Phe Gly Asn Lys Leu Gly Leu Leu Gly Asn Pro Gln | |
|               515               520               525 | |

| cat ctc gag cat gtt aaa tcc gtc gaa aag gat act gta gtg gaa aaa | 1632 |
| His Leu Glu His Val Lys Ser Val Glu Lys Asp Thr Val Val Glu Lys | |
|               530               535               540 | |

| tta gaa tcg tca gag gct aat agc agc agc tcg gtc tag | 1671 |
| Leu Glu Ser Ser Glu Ala Asn Ser Ser Ser Ser Val | |
| 545               550               555 | |

<210> SEQ ID NO 2
<211> LENGTH: 556
<212> TYPE: PRT
<213> ORGANISM: Kluyveromyces marxianus

<400> SEQUENCE: 2

Met Thr Leu Lys Asp Lys Leu Leu Leu Arg Asn Ile Glu Phe Lys Gly
1               5                   10                  15

Thr Phe Tyr Ala Lys Phe Pro Gln Ile His Asn Ile Tyr Ala Ile Gly
            20                  25                  30

Val Ile Ser Cys Ile Ser Gly Leu Met Phe Gly Phe Asp Ile Ser Ser
        35                  40                  45

Met Ser Ser Met Ile Gly Thr Glu Thr Tyr Lys Lys Tyr Phe Asp His
    50                  55                  60

Pro Lys Ser Ile Thr Gln Gly Gly Ile Thr Ala Ser Met Ser Gly Gly
65                  70                  75                  80

Ser Phe Leu Gly Ser Leu Leu Ser Pro Ala Ile Ser Asp Thr Phe Gly
                85                  90                  95

```
Arg Lys Val Ser Leu His Ile Cys Ala Val Leu Trp Ile Val Gly Cys
                100                 105                 110

Ile Leu Gln Ser Ala Ala Gln Asp Gln Pro Met Leu Ile Ala Gly Arg
            115                 120                 125

Val Ile Ala Gly Leu Gly Ile Gly Phe Gly Ser Gly Ser Ala Pro Ile
        130                 135                 140

Tyr Cys Ser Glu Ile Ser Pro Pro Lys Val Arg Gly Leu Ile Thr Gly
145                 150                 155                 160

Leu Phe Gln Phe Ser Ile Thr Val Gly Ile Met Ile Leu Phe Tyr Val
                165                 170                 175

Gly Tyr Gly Cys His Phe Leu Ser Gly Asn Leu Ser Phe Arg Leu Thr
            180                 185                 190

Trp Gly Leu Gln Val Ile Pro Gly Phe Val Leu Val Gly Val Leu
        195                 200                 205

Phe Leu Pro Glu Ser Pro Arg Trp Leu Ala Asn His Asp Arg Trp Glu
210                 215                 220

Glu Thr Glu Ser Ile Val Ala Lys Val Val Ala Lys Gly Asn Val Asp
225                 230                 235                 240

Asp Glu Glu Val Lys Phe Gln Leu Glu Glu Ile Lys Glu Gln Val Ile
            245                 250                 255

Leu Asp Ala Ala Ala Lys Asn Phe Ser Phe Lys Asp Leu Leu Arg Pro
        260                 265                 270

Lys Thr Arg Lys Lys Leu Phe Val Gly Val Cys Ala Gln Met Trp Gln
    275                 280                 285

Gln Leu Cys Gly Met Asn Val Met Met Tyr Tyr Ile Val Tyr Val Phe
290                 295                 300

Asn Met Ala Gly Tyr Thr Gly Asn Thr Asn Leu Val Ala Ser Ser Ile
305                 310                 315                 320

Gln Tyr Val Leu Asn Val Leu Met Thr Phe Pro Ala Leu Phe Leu Ile
            325                 330                 335

Asp Lys Val Gly Arg Arg Pro Val Leu Ile Val Gly Gly Ile Phe Met
        340                 345                 350

Phe Thr Trp Leu Phe Ala Val Ala Gly Leu Leu Ala Ser Tyr Ser Val
    355                 360                 365

Pro Ala Pro Asn Gly Val Asn Gly Asp Asp Thr Val Thr Ile Arg Ile
370                 375                 380

Pro Asp Lys His Lys Ser Ala Ala Lys Gly Val Ile Ala Cys Ser Tyr
385                 390                 395                 400

Leu Phe Val Cys Ser Phe Ala Pro Thr Trp Gly Ile Gly Ile Trp Ile
            405                 410                 415

Tyr Cys Ser Glu Ile Phe Asn Asn Met Glu Arg Ala Lys Gly Ser Ser
        420                 425                 430

Val Ala Ala Ala Thr Asn Trp Ala Phe Asn Phe Ala Leu Ala Met Phe
    435                 440                 445

Val Pro Ser Ala Phe Lys Asn Ile Ser Trp Lys Thr Tyr Ile Val Phe
450                 455                 460

Gly Val Phe Ser Val Ala Leu Thr Val Gln Thr Tyr Phe Met Phe Pro
465                 470                 475                 480

Glu Thr Arg Gly Lys Thr Leu Glu Glu Ile Asp Gln Met Trp Val Asp
            485                 490                 495

Asn Ile Pro Ala Trp Lys Thr Ser Ser Tyr Ile Pro Gln Leu Pro Ile
        500                 505                 510
```

```
Ile Glu Asp Glu Phe Gly Asn Lys Leu Gly Leu Leu Gly Asn Pro Gln
            515                 520                 525

His Leu Glu His Val Lys Ser Val Glu Lys Asp Thr Val Val Glu Lys
        530                 535                 540

Leu Glu Ser Ser Glu Ala Asn Ser Ser Ser Ser Val
545                 550                 555

<210> SEQ ID NO 3
<211> LENGTH: 1620
<212> TYPE: DNA
<213> ORGANISM: Pichia guilliermondii
<220> FEATURE:
<221> NAME/KEY: CDS
<222> LOCATION: (1)..(1617)

<400> SEQUENCE: 3
```

| | | | | | | | | | | | | | | | | |
|---|---|---|---|---|---|---|---|---|---|---|---|---|---|---|---|---|
| atg | gct | tac | gag | gac | aaa | cta | gtg | gct | ccg | gcc | ttg | aag | ttt | aga | aac | 48 |
| Met | Ala | Tyr | Glu | Asp | Lys | Leu | Val | Ala | Pro | Ala | Leu | Lys | Phe | Arg | Asn | |
| 1 | | | | 5 | | | | | 10 | | | | | 15 | | |
| ttt | ctt | gac | aaa | act | ccc | aat | atc | tac | aat | cca | tat | atc | att | tct | ata | 96 |
| Phe | Leu | Asp | Lys | Thr | Pro | Asn | Ile | Tyr | Asn | Pro | Tyr | Ile | Ile | Ser | Ile | |
| | | | 20 | | | | | 25 | | | | | 30 | | | |
| atc | tcg | tgc | att | gcg | ggt | atg | atg | ttc | ggt | ttt | gat | att | tct | tca | atg | 144 |
| Ile | Ser | Cys | Ile | Ala | Gly | Met | Met | Phe | Gly | Phe | Asp | Ile | Ser | Ser | Met | |
| | 35 | | | | | 40 | | | | | 45 | | | | | |
| tca | gcg | ttt | gtc | agt | tta | cca | gca | tac | gtg | aat | tat | ttc | gat | aca | cct | 192 |
| Ser | Ala | Phe | Val | Ser | Leu | Pro | Ala | Tyr | Val | Asn | Tyr | Phe | Asp | Thr | Pro | |
| 50 | | | | | 55 | | | | | 60 | | | | | | |
| tca | gca | gtg | att | caa | gga | ttt | atc | aca | tct | gcc | atg | gct | ttg | ggt | tca | 240 |
| Ser | Ala | Val | Ile | Gln | Gly | Phe | Ile | Thr | Ser | Ala | Met | Ala | Leu | Gly | Ser | |
| 65 | | | | | 70 | | | | | 75 | | | | | 80 | |
| ttt | ttc | ggg | tca | att | gct | tct | gcg | ttt | gtg | tct | gag | cca | ttt | gga | aga | 288 |
| Phe | Phe | Gly | Ser | Ile | Ala | Ser | Ala | Phe | Val | Ser | Glu | Pro | Phe | Gly | Arg | |
| | | | | 85 | | | | | 90 | | | | | 95 | | |
| cga | gct | tcc | tta | cta | act | tgt | tcg | tgg | ttt | tgg | atg | ata | gga | gca | gcc | 336 |
| Arg | Ala | Ser | Leu | Leu | Thr | Cys | Ser | Trp | Phe | Trp | Met | Ile | Gly | Ala | Ala | |
| | | | 100 | | | | | 105 | | | | | 110 | | | |
| atc | caa | gcg | tct | tcg | cag | aac | cga | gct | caa | ttg | att | att | ggt | cgg | att | 384 |
| Ile | Gln | Ala | Ser | Ser | Gln | Asn | Arg | Ala | Gln | Leu | Ile | Ile | Gly | Arg | Ile | |
| | 115 | | | | | 120 | | | | | 125 | | | | | |
| ata | tct | gga | ttt | ggg | gtt | ggt | ttc | ggg | tcg | tct | gtg | gct | ccc | gta | tat | 432 |
| Ile | Ser | Gly | Phe | Gly | Val | Gly | Phe | Gly | Ser | Ser | Val | Ala | Pro | Val | Tyr | |
| 130 | | | | | 135 | | | | | 140 | | | | | | |
| ggc | tcc | gag | atg | gca | cct | aga | aaa | att | aga | gga | aga | att | ggt | gga | att | 480 |
| Gly | Ser | Glu | Met | Ala | Pro | Arg | Lys | Ile | Arg | Gly | Arg | Ile | Gly | Gly | Ile | |
| 145 | | | | | 150 | | | | | 155 | | | | | 160 | |
| ttt | caa | tta | tct | gtc | acc | ctc | ggt | atc | atg | att | atg | ttc | ttc | ata | agt | 528 |
| Phe | Gln | Leu | Ser | Val | Thr | Leu | Gly | Ile | Met | Ile | Met | Phe | Phe | Ile | Ser | |
| | | | | 165 | | | | | 170 | | | | | 175 | | |
| tac | gga | act | tct | cat | att | aag | act | gcg | gca | gct | ttc | agg | tta | gcc | tgg | 576 |
| Tyr | Gly | Thr | Ser | His | Ile | Lys | Thr | Ala | Ala | Ala | Phe | Arg | Leu | Ala | Trp | |
| | | | 180 | | | | | 185 | | | | | 190 | | | |
| gca | ctc | cag | atc | att | cct | gga | ctc | ctc | atg | tgt | att | ggt | gtc | ttc | ttt | 624 |
| Ala | Leu | Gln | Ile | Ile | Pro | Gly | Leu | Leu | Met | Cys | Ile | Gly | Val | Phe | Phe | |
| | | 195 | | | | | 200 | | | | | 205 | | | | |
| att | cca | gaa | tct | cct | aga | tgg | ttg | gcc | aaa | caa | ggt | cac | tgg | gac | gaa | 672 |
| Ile | Pro | Glu | Ser | Pro | Arg | Trp | Leu | Ala | Lys | Gln | Gly | His | Trp | Asp | Glu | |
| | 210 | | | | | 215 | | | | | 220 | | | | | |
| gcc | gaa | atc | att | gta | gcc | aaa | att | caa | gcc | aaa | gga | gat | cga | gaa | aat | 720 |
| Ala | Glu | Ile | Ile | Val | Ala | Lys | Ile | Gln | Ala | Lys | Gly | Asp | Arg | Glu | Asn | |
| 225 | | | | | 230 | | | | | 235 | | | | | 240 | |

-continued

| | | |
|---|---|---|
| ccc gat gtt ttg att gaa att tcg gaa ata aaa gac caa ttg atg gtt<br>Pro Asp Val Leu Ile Glu Ile Ser Glu Ile Lys Asp Gln Leu Met Val<br>245 250 255 | 768 |
| gac gag aat gcc aaa gcc ttt acc tat gct gac ttg ttt tcg aaa aaa<br>Asp Glu Asn Ala Lys Ala Phe Thr Tyr Ala Asp Leu Phe Ser Lys Lys<br>260 265 270 | 816 |
| tat ctt ccc aga acc atc aca gcc atg ttc gct caa atc tgg caa caa<br>Tyr Leu Pro Arg Thr Ile Thr Ala Met Phe Ala Gln Ile Trp Gln Gln<br>275 280 285 | 864 |
| ttg aca gga atg aat gtc atg atg tac tat atc gtt tac att ttc gaa<br>Leu Thr Gly Met Asn Val Met Met Tyr Tyr Ile Val Tyr Ile Phe Glu<br>290 295 300 | 912 |
| atg gct ggc tac ggt gga aat gga gtg ttg gta tca tcg aca att cag<br>Met Ala Gly Tyr Gly Gly Asn Gly Val Leu Val Ser Ser Thr Ile Gln<br>305 310 315 320 | 960 |
| tac gtt atc ttt gtc gtt gtt aca ttt gtc tca tta ttc ttt ttg gac<br>Tyr Val Ile Phe Val Val Val Thr Phe Val Ser Leu Phe Phe Leu Asp<br>325 330 335 | 1008 |
| aaa ttt gga aga aga aaa att tta ctt gtc gga gca gct tcc atg atg<br>Lys Phe Gly Arg Arg Lys Ile Leu Leu Val Gly Ala Ala Ser Met Met<br>340 345 350 | 1056 |
| acc tgg cag ttt gca gtg gca ggg atc ttg gcc agg tac tcg gtc ccg<br>Thr Trp Gln Phe Ala Val Ala Gly Ile Leu Ala Arg Tyr Ser Val Pro<br>355 360 365 | 1104 |
| tac gat ctc agc gat act gtc aaa att aaa att cct gac aat cac aaa<br>Tyr Asp Leu Ser Asp Thr Val Lys Ile Lys Ile Pro Asp Asn His Lys<br>370 375 380 | 1152 |
| tcg gct gca aaa ggt gtc att gca tgc tgt tat ctt ttc gta gca tcg<br>Ser Ala Ala Lys Gly Val Ile Ala Cys Cys Tyr Leu Phe Val Ala Ser<br>385 390 395 400 | 1200 |
| ttc gga ttt tcc tgg gga gtt ggt atc tgg tta tac tgc tct gaa gtc<br>Phe Gly Phe Ser Trp Gly Val Gly Ile Trp Leu Tyr Cys Ser Glu Val<br>405 410 415 | 1248 |
| tgg gga gac tca caa tcg aga cag aga gga gcc gct gtg tca act gct<br>Trp Gly Asp Ser Gln Ser Arg Gln Arg Gly Ala Ala Val Ser Thr Ala<br>420 425 430 | 1296 |
| tca aat tgg att ttc aat ttt gcg ctc gcc atg ttc aca cca tct tcg<br>Ser Asn Trp Ile Phe Asn Phe Ala Leu Ala Met Phe Thr Pro Ser Ser<br>435 440 445 | 1344 |
| ttt aaa aat atc acc tgg aag aca tac tgt att tat gcc act ttc tgc<br>Phe Lys Asn Ile Thr Trp Lys Thr Tyr Cys Ile Tyr Ala Thr Phe Cys<br>450 455 460 | 1392 |
| gca tgt atg ttc atc cat gtg ttc ttc ttc cca gaa acc aag ggg<br>Ala Cys Met Phe Ile His Val Phe Phe Phe Phe Pro Glu Thr Lys Gly<br>465 470 475 480 | 1440 |
| aag cgc ttg gaa gaa att gct caa att tgg gaa gaa aaa att cca gct<br>Lys Arg Leu Glu Glu Ile Ala Gln Ile Trp Glu Glu Lys Ile Pro Ala<br>485 490 495 | 1488 |
| tgg aaa acc acc aac tgg caa cct cat gtt cct ttg ttg tcg gac cac<br>Trp Lys Thr Thr Asn Trp Gln Pro His Val Pro Leu Leu Ser Asp His<br>500 505 510 | 1536 |
| gaa ctt gcg gaa aag atc aat gcc gaa cat gtg gag aac gtg aat tct<br>Glu Leu Ala Glu Lys Ile Asn Ala Glu His Val Glu Asn Val Asn Ser<br>515 520 525 | 1584 |
| agg gaa caa tcg gat gac gag aag tcg cag gta taa<br>Arg Glu Gln Ser Asp Asp Glu Lys Ser Gln Val<br>530 535 | 1620 |

```
<210> SEQ ID NO 4
<211> LENGTH: 539
<212> TYPE: PRT
<213> ORGANISM: Pichia guilliermondii

<400> SEQUENCE: 4

Met Ala Tyr Glu Asp Lys Leu Val Ala Pro Ala Leu Lys Phe Arg Asn
1               5                   10                  15

Phe Leu Asp Lys Thr Pro Asn Ile Tyr Asn Pro Tyr Ile Ile Ser Ile
            20                  25                  30

Ile Ser Cys Ile Ala Gly Met Met Phe Gly Phe Asp Ile Ser Ser Met
        35                  40                  45

Ser Ala Phe Val Ser Leu Pro Ala Tyr Val Asn Tyr Phe Asp Thr Pro
    50                  55                  60

Ser Ala Val Ile Gln Gly Phe Ile Thr Ser Ala Met Ala Leu Gly Ser
65                  70                  75                  80

Phe Phe Gly Ser Ile Ala Ser Ala Phe Val Ser Glu Pro Phe Gly Arg
                85                  90                  95

Arg Ala Ser Leu Leu Thr Cys Ser Trp Phe Trp Met Ile Gly Ala Ala
            100                 105                 110

Ile Gln Ala Ser Ser Gln Asn Arg Ala Gln Leu Ile Ile Gly Arg Ile
        115                 120                 125

Ile Ser Gly Phe Gly Val Gly Phe Gly Ser Ser Val Ala Pro Val Tyr
    130                 135                 140

Gly Ser Glu Met Ala Pro Arg Lys Ile Arg Gly Arg Ile Gly Ile
145                 150                 155                 160

Phe Gln Leu Ser Val Thr Leu Gly Ile Met Ile Met Phe Phe Ile Ser
                165                 170                 175

Tyr Gly Thr Ser His Ile Lys Thr Ala Ala Ala Phe Arg Leu Ala Trp
            180                 185                 190

Ala Leu Gln Ile Ile Pro Gly Leu Leu Met Cys Ile Gly Val Phe Phe
        195                 200                 205

Ile Pro Glu Ser Pro Arg Trp Leu Ala Lys Gln Gly His Trp Asp Glu
    210                 215                 220

Ala Glu Ile Ile Val Ala Lys Ile Gln Ala Lys Gly Asp Arg Glu Asn
225                 230                 235                 240

Pro Asp Val Leu Ile Glu Ile Ser Glu Ile Lys Asp Gln Leu Met Val
                245                 250                 255

Asp Glu Asn Ala Lys Ala Phe Thr Tyr Ala Asp Leu Phe Ser Lys Lys
            260                 265                 270

Tyr Leu Pro Arg Thr Ile Thr Ala Met Phe Ala Gln Ile Trp Gln Gln
        275                 280                 285

Leu Thr Gly Met Asn Val Met Met Tyr Tyr Ile Val Tyr Ile Phe Glu
    290                 295                 300

Met Ala Gly Tyr Gly Gly Asn Gly Val Leu Val Ser Ser Thr Ile Gln
305                 310                 315                 320

Tyr Val Ile Phe Val Val Val Thr Phe Val Ser Leu Phe Phe Leu Asp
                325                 330                 335

Lys Phe Gly Arg Arg Lys Ile Leu Leu Val Gly Ala Ala Ser Met Met
            340                 345                 350

Thr Trp Gln Phe Ala Val Ala Gly Ile Leu Ala Arg Tyr Ser Val Pro
        355                 360                 365

Tyr Asp Leu Ser Asp Thr Val Lys Ile Lys Ile Pro Asp Asn His Lys
    370                 375                 380
```

```
Ser Ala Ala Lys Gly Val Ile Ala Cys Cys Tyr Leu Phe Val Ala Ser
385                 390                 395                 400

Phe Gly Phe Ser Trp Gly Val Gly Ile Trp Leu Tyr Cys Ser Glu Val
            405                 410                 415

Trp Gly Asp Ser Gln Ser Arg Gln Arg Gly Ala Ala Val Ser Thr Ala
            420                 425                 430

Ser Asn Trp Ile Phe Asn Phe Ala Leu Ala Met Phe Thr Pro Ser Ser
        435                 440                 445

Phe Lys Asn Ile Thr Trp Lys Thr Tyr Cys Ile Tyr Ala Thr Phe Cys
    450                 455                 460

Ala Cys Met Phe Ile His Val Phe Phe Phe Pro Glu Thr Lys Gly
465                 470                 475                 480

Lys Arg Leu Glu Glu Ile Ala Gln Ile Trp Glu Lys Ile Pro Ala
                485                 490                 495

Trp Lys Thr Thr Asn Trp Gln Pro His Val Pro Leu Leu Ser Asp His
            500                 505                 510

Glu Leu Ala Glu Lys Ile Asn Ala Glu His Val Glu Asn Val Asn Ser
        515                 520                 525

Arg Glu Gln Ser Asp Asp Glu Lys Ser Gln Val
    530                 535
```

<210> SEQ ID NO 5
<211> LENGTH: 1725
<212> TYPE: DNA
<213> ORGANISM: Saccharomyces cerevisiae
<220> FEATURE:
<221> NAME/KEY: CDS
<222> LOCATION: (1)..(1722)

<400> SEQUENCE: 5

```
atg gca gtt gag gag aac aat gtg cct gtt gtt tca cag caa ccc caa    48
Met Ala Val Glu Glu Asn Asn Val Pro Val Val Ser Gln Gln Pro Gln
1               5                   10                  15 gct ggt gaa gac gtg atc tct tca ctc agt aaa gat tcc cat tta agc    96
Ala Gly Glu Asp Val Ile Ser Ser Leu Ser Lys Asp Ser His Leu Ser
            20                  25                  30 gca caa tct caa aag tat tcc aat gat gaa ttg aaa gcc ggt gag tca   144
Ala Gln Ser Gln Lys Tyr Ser Asn Asp Glu Leu Lys Ala Gly Glu Ser
        35                  40                  45 ggg cct gaa ggc tcc caa agt gtt cct ata gag ata ccc aag aag ccc   192
Gly Pro Glu Gly Ser Gln Ser Val Pro Ile Glu Ile Pro Lys Lys Pro
    50                  55                  60 atg tct gaa tat gtt acc gtt tcc ttg ctt tgt ttg tgt gtt gcc ttc   240
Met Ser Glu Tyr Val Thr Val Ser Leu Leu Cys Leu Cys Val Ala Phe
65                  70                  75                  80 ggc ggc ttc atg ttt ggc tgg gat acc agt act att tct ggg ttt gtt   288
Gly Gly Phe Met Phe Gly Trp Asp Thr Ser Thr Ile Ser Gly Phe Val
                85                  90                  95 gtc caa aca gac ttt ttg aga agg ttt ggt atg aaa cat aag gat ggt   336
Val Gln Thr Asp Phe Leu Arg Arg Phe Gly Met Lys His Lys Asp Gly
            100                 105                 110 acc cac tat ttg tca aac gtc aga aca ggt tta atc gtc gcc att ttc   384
Thr His Tyr Leu Ser Asn Val Arg Thr Gly Leu Ile Val Ala Ile Phe
        115                 120                 125 aat att ggc tgt gcc ttt ggt ggt att ata ctt tcc aaa ggt gga gat   432
Asn Ile Gly Cys Ala Phe Gly Gly Ile Ile Leu Ser Lys Gly Gly Asp
    130                 135                 140
```

```
atg tat ggc cgt aaa aag ggt ctt tcg att gtc gtc tcg gtt tat ata         480
Met Tyr Gly Arg Lys Lys Gly Leu Ser Ile Val Val Ser Val Tyr Ile
145                 150                 155                 160 gtt ggt att atc att caa att gcc tct atc aac aag tgg tac caa tat         528
Val Gly Ile Ile Ile Gln Ile Ala Ser Ile Asn Lys Trp Tyr Gln Tyr
                165                 170                 175 ttc att ggt aga atc ata tct ggt ttg ggt gtc ggc ggc atc gct gtc         576
Phe Ile Gly Arg Ile Ile Ser Gly Leu Gly Val Gly Gly Ile Ala Val
            180                 185                 190 tta tgt cct atg ttg atc tct gaa att gct cca aag cac ttg aga ggc         624
Leu Cys Pro Met Leu Ile Ser Glu Ile Ala Pro Lys His Leu Arg Gly
        195                 200                 205 aca cta gtt tct tgt tat cag ctg atg att act gca ggt atc ttt ttg         672
Thr Leu Val Ser Cys Tyr Gln Leu Met Ile Thr Ala Gly Ile Phe Leu
    210                 215                 220 ggc tac tgt act aat tac ggt aca aag agc tat tcg aac tca gtt caa         720
Gly Tyr Cys Thr Asn Tyr Gly Thr Lys Ser Tyr Ser Asn Ser Val Gln
225                 230                 235                 240 tgg aga gtt cca tta ggg cta tgt ttc gct tgg tca tta ttt atg att         768
Trp Arg Val Pro Leu Gly Leu Cys Phe Ala Trp Ser Leu Phe Met Ile
                245                 250                 255 ggc gct ttg acg tta gtt cct gaa tcc cca cgt tat tta tgt gag gtg         816
Gly Ala Leu Thr Leu Val Pro Glu Ser Pro Arg Tyr Leu Cys Glu Val
            260                 265                 270 aat aag gta gaa gac gcc aag cgt tcc att gct aag tct aac aag gtg         864
Asn Lys Val Glu Asp Ala Lys Arg Ser Ile Ala Lys Ser Asn Lys Val
        275                 280                 285 tca cca gag gat cct gcc gtc cag gcc gag tta gat ctg atc atg gcc         912
Ser Pro Glu Asp Pro Ala Val Gln Ala Glu Leu Asp Leu Ile Met Ala
    290                 295                 300 ggt ata gaa gct gaa aaa ctg gct ggc aat gcg tcc tgg ggg gaa tta         960
Gly Ile Glu Ala Glu Lys Leu Ala Gly Asn Ala Ser Trp Gly Glu Leu
305                 310                 315                 320 ttt tcc acc aag acc aaa gta ttt caa cgt ttg ttg atg ggt gtg ttt        1008
Phe Ser Thr Lys Thr Lys Val Phe Gln Arg Leu Leu Met Gly Val Phe
                325                 330                 335 gtt caa atg ttc caa caa tta acc ggt aac aat tat ttt ttc tac tac        1056
Val Gln Met Phe Gln Gln Leu Thr Gly Asn Asn Tyr Phe Phe Tyr Tyr
            340                 345                 350 ggt acc gtt att ttc aag tca gtt ggc ctg gat gat tcc ttt gaa aca        1104
Gly Thr Val Ile Phe Lys Ser Val Gly Leu Asp Asp Ser Phe Glu Thr
        355                 360                 365 tcc att gtc att ggt gta gtc aac ttt gcc tcc act ttc ttt agt ttg        1152
Ser Ile Val Ile Gly Val Val Asn Phe Ala Ser Thr Phe Phe Ser Leu
    370                 375                 380 tgg act gtc gaa aac ttg ggg cgt cgt aaa tgt tta ctt ttg ggc gct        1200
Trp Thr Val Glu Asn Leu Gly Arg Arg Lys Cys Leu Leu Leu Gly Ala
385                 390                 395                 400 gcc act atg atg gct tgt atg gtc atc tac gcc tct gtt ggt gtt act        1248
Ala Thr Met Met Ala Cys Met Val Ile Tyr Ala Ser Val Gly Val Thr
                405                 410                 415 aga tta tat cct cac ggt aaa agc cag cca tct tct aaa ggt gcc ggt        1296
Arg Leu Tyr Pro His Gly Lys Ser Gln Pro Ser Ser Lys Gly Ala Gly
            420                 425                 430 aac tgt atg att gtc ttt acc tgt ttt tat att ttc tgt tat gcc aca        1344
Asn Cys Met Ile Val Phe Thr Cys Phe Tyr Ile Phe Cys Tyr Ala Thr
        435                 440                 445 acc tgg gcg cca gtt gcc tgg gtc atc aca gca gaa tca ttc cca ctg        1392
Thr Trp Ala Pro Val Ala Trp Val Ile Thr Ala Glu Ser Phe Pro Leu
    450                 455                 460
```

```
aga gtc aag tcg aaa tgt atg gcg ttg gcc tct gct tcc aat tgg gta    1440
Arg Val Lys Ser Lys Cys Met Ala Leu Ala Ser Ala Ser Asn Trp Val
465                 470                 475                 480 tgg ggg ttc ttg att gca ttt ttc acc cca ttc atc aca tct gcc att    1488
Trp Gly Phe Leu Ile Ala Phe Phe Thr Pro Phe Ile Thr Ser Ala Ile
                485                 490                 495 aac ttc tac tac ggt tat gtc ttc atg ggc tgt ttg gtt gcc atg ttt    1536
Asn Phe Tyr Tyr Gly Tyr Val Phe Met Gly Cys Leu Val Ala Met Phe
            500                 505                 510 ttt tat gtc ttt ttc ttt gtt cca gaa act aaa ggc cta tcg tta gaa    1584
Phe Tyr Val Phe Phe Phe Val Pro Glu Thr Lys Gly Leu Ser Leu Glu
        515                 520                 525 gaa att caa gaa tta tgg gaa gaa ggt gtt tta cct tgg aaa tct gaa    1632
Glu Ile Gln Glu Leu Trp Glu Glu Gly Val Leu Pro Trp Lys Ser Glu
    530                 535                 540 ggc tgg att cct tca tcc aga aga ggt aat aat tac gat tta gag gat    1680
Gly Trp Ile Pro Ser Ser Arg Arg Gly Asn Asn Tyr Asp Leu Glu Asp
545                 550                 555                 560 tta caa cat gac gac aaa ccg tgg tac aag gcc atg cta gaa taa        1725
Leu Gln His Asp Asp Lys Pro Trp Tyr Lys Ala Met Leu Glu
                565                 570

<210> SEQ ID NO 6
<211> LENGTH: 574
<212> TYPE: PRT
<213> ORGANISM: Saccharomyces cerevisiae

<400> SEQUENCE: 6

Met Ala Val Glu Glu Asn Asn Val Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Ser Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220
```

```
Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
            245                 250                 255

Gly Ala Leu Thr Leu Val Pro Glu Ser Pro Arg Tyr Leu Cys Glu Val
            260                 265                 270

Asn Lys Val Glu Asp Ala Lys Arg Ser Ile Ala Lys Ser Asn Lys Val
            275                 280                 285

Ser Pro Glu Asp Pro Ala Val Gln Ala Glu Leu Asp Leu Ile Met Ala
            290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
    450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
            485                 490                 495

Asn Phe Tyr Tyr Gly Tyr Val Phe Met Gly Cys Leu Val Ala Met Phe
            500                 505                 510

Phe Tyr Val Phe Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
            530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570
```

L-ARABINOSE FERMENTING YEAST

CROSS-REFERENCE TO RELATED APPLICATIONS

This application is a divisional application of U.S. application Ser. No. 12/909,523, filed Oct. 21, 2010, now U.S. Pat. No. 8,372,626, issued Feb. 12, 2013, which is a divisional application of U.S. application Ser. No. 11/912,493, filed Oct. 24, 2007, now U.S. Pat. No. 7,846,712, issued Dec. 7, 2010, which is a national stage entry of International Application No. PCT/U.S.07/64330, filed Mar. 19, 2007, which claims priority to U.S. Provisional Application No. 60/810,562, filed Jun. 1, 2006. The contents of each application listed above are incorporated by reference in their entirety.

CONTRACTUAL ORIGIN

The United States Government has rights in this invention under Contract No. DE-AC36-99GO10337 between the United States Department of Energy and the National Renewable Energy Laboratory, a Division of the Midwest Research Institute.

BACKGROUND

Fuel ethanol is a suitable alternative to fossil fuels. Ethanol may be produced from plant biomass, which is an economical and renewable resource that is available in large amounts. Examples of biomass include agricultural feedstocks, paper wastes, wood chips and so on. The sources of biomass vary from region to region based on the abundance of natural or agricultural biomass that is available in a particular region. For example, while sugar cane is the primary source of biomass used to produce ethanol in Brazil, corn-derived biomass, corn starch is a large source of biomass to produce ethanol in the United States. Other agricultural feedstocks include, by way of example: straw; grasses such as switchgrass; grains; and any other lignocellulosic or starch-bearing material.

A typical biomass substrate contains from 35-45% cellulose, 25-40% hemicellulose, and 15-30% lignin, although sources may be found that deviate from these general ranges. As is known in the art, cellulose is polymer of glucose sub-units, and hemicellulose contains mostly xylose. Arabinose is also a significant fermentable substrate that is found in biomass, such as corn fiber and many herbaceous crops in varying amounts. Other researchers have investigated the utilization of arabinose and hemicellulose, as reported by Hespell, R. B. 1998. *Extraction and characterization of hemicellulose from the corn fiber produced by corn wet-milling processes*. J. Agric. Food Chem. 46:2615-2619, and McMillan, J. D., and B. L. Boynton. 1994. *Arabinose utilization by xylose-fermenting yeasts and fungi*. Appl. Biochem, Biotechnol. 45-46: 569-584. The two most abundant types of pentose that exist naturally are D-xylose and L-arabinose.

It is problematic that most of the currently available ethanol-producing microorganisms are only capable of utilizing hexose sugar, such as glucose. This is confirmed by a review of the art, such as is reported by Barnett, J. A. 1976. The utilization of sugars by yeasts. Adv. Carbohydr. Chem. Biochem. 32:125-234. Many types of yeast, especially *Saccharomyces cerevisiae* and related species, are very effective in fermenting glucose-based feedstocks into ethanol through anaerobic fermentation. However, these glucose-fermenting yeasts are unable to ferment xylose or L-arabinose, and are unable to grow solely on these pentose sugars. Although other yeast species, such as *Pichia stipitis* and *Candida shehatae*, can ferment xylose to ethanol, they are not as effective as *Saccharomyces* for fermentation of glucose and have a relatively low level of ethanol tolerance. Thus, the present range of available yeast are not entirely suitable for large scale industrial production of ethanol from biomass.

Most bacteria, including *E. coli* and *Bacillus subtilis*, utilize L-arabinose for aerobic growth, but they do not ferment L-arabinose to ethanol. These and other microorganisms, such as *Zymononas mobilis*, have also been genetically modified to produce ethanol from hexose or pentose. This has been reported, for example, in Deanda, K., M. Zhang, C. Eddy, and S. Picataggio, 1996, Development of an arabinose-fermenting *Zymomonas mobilis* strain by metabolic pathway engineering. Appl. Environ. Microbiol. 62:4465-4470; and Zhang, M., C. Eddy, K. Deanda, M. Finkelstein, and S. Picataggio, 1995 Metabolic engineering of a pentose metabolism pathway in ethanologenic *Zymomonas mobilis*. Science 267: 240-243. However, it remains the case that the low alcohol tolerance of these non-yeast microorganisms limits their utility in the ethanol industry.

Much effort has been made over the last decade or so, without truly overcoming the problem of developing new strains that ferment xylose to generate ethanol. Such efforts are reported, for example, in Kotter, P., R. Amore, C. P. Hollenberg, and M. Ciriacy. 1990. Isolation and characterization of the *Pichia stipitis* xylitol dehydrogenase gene, XYL2, and construction of a xylose-utilizing *Saccharomyces cerevisiae* transformant. Curr. Genet. 18:493-500; and Wahlbom, C. P., and B. Hahn-Hagerdal, 2002 Recent studies have been conducted on yeast strains that potentially ferment arabinose. Sedlak, M., and N. W. Ho. 2001. Expression of *E. coli* araBAD operon encoding enzymes for metabolizing L-arabinose in *Saccharomyces cerevisiae*, Enzyme Microb. Technol. 28:16-24 discloses the expression of an *E. coli* araBAD operon encoding enzymes for metabolizing L-arabinose in *Saccharomyces cerevisiae*. Although this strain expresses araA, araB and araD proteins, it is incapable of producing ethanol.

U.S. patent application Ser. No. 10/983,951 by Boles and Becker discloses the creation of a yeast strain that may ferment L-arabinose. However, the overall yield is relatively low, at about 60% of theoretical value. The rate of arabinose transport into *S. cerevisiae* may be a limiting factor for complete utilization of the pentose substrate. Boles and Becker attempted to enhance arabinose uptake by overexpressing the GAL2-encoded galactose permease in *S. cerevisiae*. However, the rate of arabinose transport using galactose permease was still much lower when compared to that exhibited by non-conventional yeast such as *Kluyveronmyces marxianus*. Another limitation that may have contributed to the low yield of ethanol in the modified strain of Becker and Boles is the poor activity of the L-arabinose isomerase encoded by the bacterial araA gene. Although Becker and Boles used an araA gene from *B. subtilis* instead of one from *E. coli*, the specific activity of the enzyme was still low. Other workers in the field have reported that low isomerase activity is a bottleneck in L-arabinose utilization by yeast.

There remains a need for new arabinose-fermenting strains that are capable of producing ethanol at high yield. There is further a need to identify novel arabinose transporters for introduction into *Saccharomyces cerevisiae* to boost the production of ethanol from arabinose.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The presently disclosed instrumentalities overcome some of the problems outlined above and advance the art by providing new yeast strains that are capable of using L-arabinose to produce ethanol at a relatively high yield. Since the yeast galactose permease may facilitate uptake of arabinose, any Gal+ strain possessing endogenous galactose permease activity may be used as described below. Although S. cerevisiae is used by way of example, the scope of coverage extends to any organisms possessing endogenous pathways to generate ethanol from arabinose and to organisms into which components of such arabinose metabolic pathways or arabinose transporters may be introduced. The use of S. cerevisiae is preferred.

In a brief overview of the recombinant technique, the endogenous yeast aldose reductase (AR) gene is disrupted by replacing the AR coding sequence with the yeast LEU2 gene. Because the yeast aldose reductase is the first enzyme to metabolize arabinose in yeast, an AR⁻ strain is used to reduce diversion of arabinose to unwanted byproducts and to prevent possible inhibition of the isomerase by arabitol. The bacterial araA, araB, and araD genes are cloned into appropriate yeast expression vectors. The expression constructs containing all three ara genes are introduced in the AR⁻ strain and the transformants were capable of making ethanol from L-arabinose.

In another aspect of this disclosure, two novel arabinose transporter genes, termed KmLAT1 and PgLAT2, have been cloned and characterized from two non-conventional yeast species, *Kluyveromyces marxianus* and *Pichia guilliermondii* (also known as *Candida guilliermondii*), respectively. Both *Kluyveromyces marxianus* and *Pichia guilliermondii* are efficient utilizers of L-arabinose, which renders them ideal sources for cloning L-arabinose transporter genes.

The KmLAT1 gene may be isolated using functional complementation of an adapted *S. cerevisiae* strain that could not grow on L-arabinose because it lacked sufficient L-arabinose transport activity. KmLat1 protein has a predicted length of 556 amino acids encoded by a single ORF of 1668 bp. It is a transmembrane protein having high homology to sugar transporters of many different yeast species. When KmLat1 is expressed in *S. cerevisiae*, transport assays using labeled L-arabinose show that this transporter has the kinetic characteristics of a low affinity arabinose transporter, with $K_m=230$ mM and $V_{max}=55$ nmol/mg·min. Transport of L-arabinose by KmLat1 is not significantly inhibited by common uncoupling agents but is out-competed by glucose, galactose, xylose, and maltose.

The PgLAT2 gene may be isolated using the technique of differential display from *Pichia guilliermondii*. The PgLAT2 gene has an ORF of 1617 nucleotides encoding a protein with a predicted length of 539 amino acids. When PgLAT2 is expressed in *S. cerevisiae*, transport assays show that this transporter has almost identical L-arabinose transport kinetics as that of wildtype *Pichia guilliermondii*. The PgLat2 transporter when expressed in *S. cerevisiae* has a K, of 0.07 mM and of 18 nmol/mg-min for L-arabinose transport. Inhibition experiments show significant inhibition of the PgLat2 transporter by protonophores (e.g., $NaN_3$, DNP, and CCP) and H+-adenosine triphosphatase (ATPase) inhibitors (e.g., DESB and DCCD) similar to inhibition in wildtype *P. guilliermondii*. Competition experiments show that L-arabinose uptake by the PgLat2 transporter is inhibited by glucose, galactose, xylose and to a lesser extent by maltose.

The transport kinetics of *S. cerevisiae* Gal2p have been measured and compared to those of KmLat1. The *S. cerevisiae* GAL2 gene (SEQ ID NO 5) under control of a TDH3 promoter exhibits 28 times greater (8.9 nmol/mg·min) L-arabinose transport rate as compared to GAL2 gene under control of a ADH1 promoter. The GAL2-encoded permease (SEQ ID NO 6) shows a K, of 550 mM and a $V_{max}$ of 425 nmol/mg·min for L-arabinose transport and a $K_m$ of 25 mM and a $V_{max}$ of 76 nmol/mg·min for galactose transport. Although L-arabinose transport by both KmLAT1 and GAL2 encoded permeases is out-competed by glucose or galactose, the inhibitory effects of glucose or galactose are greater on the GAL2 encoded permease than on the KmLAT1 encoded transporter.

It is further disclosed here that a *S. cerevisiae* strain may be transformed with different combinations of the KmLAT1 and PgLAT2 transporter genes and a plasmid carrying the GAL2 gene native to *S. cerevisiae*. The doubling time for the PgLat2p and Gal2p co-expressing cells grown on L-arabinose is markedly shorter than that of the cells expressing only Gal2p, suggesting that L-arabinose uptake may have been enhanced in these cells. In addition, the PgLat2p and Gal2p co-expressing cells appear to grow to a higher optical density at saturation, suggesting that this strain may be able to utilize the L-arabinose in the medium more completely. This conclusion is supported by HPLC analysis which shows significantly less residual L-arabinose in the culture of cells expressing PgLat2p and Gal2p.

In one embodiment, the transformed strains that carry the new transporter genes may be further transformed with plasmids carrying three bacterial genes, araA, araB and araC, which encode proteins that may be utilized for arabinose utilization and fermentation. In another embodiment, the bacterial genes, araA, araB and araC, may be transformed into a yeast strain that does not carry any of the new transporter genes.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2 shows the DNA (SEQ ID NO. 1) sequence of *Kluyveromyces marxianus* KmLAT1, and the predicted protein sequence (SEQ ID NO: 2).

FIG. 7 shows the DNA (SEQ ID NO. 3) sequence of *Pichia guilliermondii* PgLAT2, and the predicted protein sequence (SEQ ID NO. 4).

FIG. 16 shows histogram with the result of ethanol production in cell-free fermentation using yeast cells expressing the three bacterial genes araB, araA, and araD.

DETAILED DESCRIPTION

Figure 1:
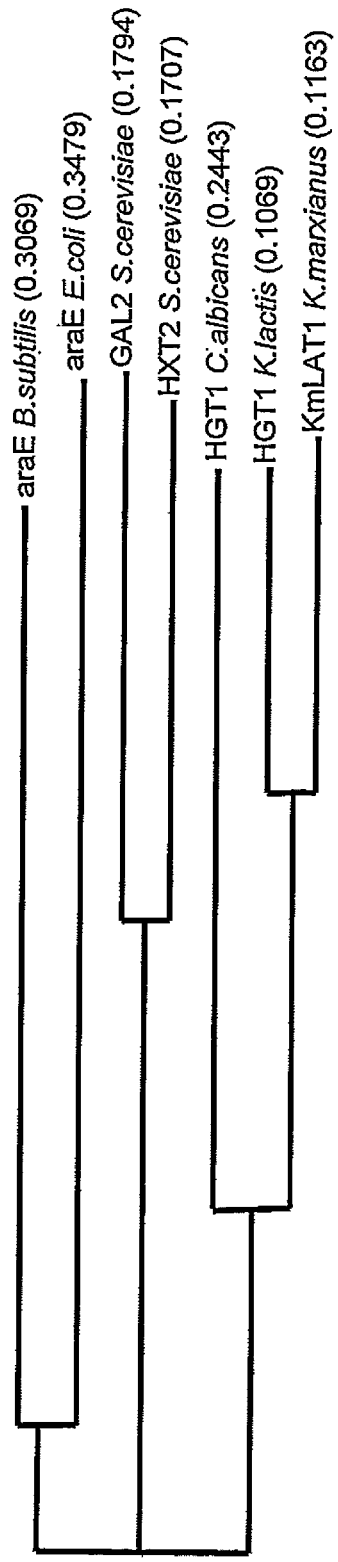
FIG. 1 shows the relationship between KmLAT1 and other transporters based on the neighbor joining method (Saitou and Nei 1987).

There will now be shown and described methods for producing transgenic yeast that are capable of metabolizing arabinose and producing ethanol. In the discussion below, parenthetical mention is made to publications from the references section for a discussion, of related procedures that may be found useful from a perspective of one skilled in the art. This is done to demonstrate what is disclosed by way of nonlimiting example.

The following definitions are provided to facilitate understanding of certain terms used frequently herein and are not meant to limit the scope of the present disclosure.

"Amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiqnitination, acetylation, amidation, glycosylation, covalent attachment of flavin, ADP-ribosylation, cross linking, iodination, methylation, and the like.

"Antibody" refers to a generally Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other Well known recombinant antibodies are included in this definition.

"Antisense" refers to polynucleotide sequences that are complementary to target "sense" polynucleotide sequence.

"Biomass" refers collectively to organic non-fossil material. "Biomass" in the present disclosure refers particularly to plant material that is used to generate fuel, such as ethanol. Examples of biomass includes but are not limited to corn fiber, dried distiller's grain, jatropha, manure, meat and bone meal, miscanthus, peat, plate waste, landscaping waste, maize, rice hulls, silage, stover, maiden grass, switchgrass, whey, and bagasse from sugarcane.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

The term "derivative" refers to compounds that are derived from a predecessor compound by way of chemical or physical modification. For example, a compound is a sugar derivatives if it is formed by oxidization of one or more terminal groups to carboxylic acids, by reduction of a carbonyl group, by substitution of hydrogen(s), amino group(s), thiol group(s), etc, for one or more hydroxyl groups on a sugar, or if it is formed by phosphorylation on a sugar molecule.

"Expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1-18:88).

"Fusion protein" refers to a first protein attached to a second, heterologous protein. Preferably, the heterologous protein is fused via recombinant DNA techniques, such that the first and second proteins are expressed in frame. The heterologous protein may confer a desired characteristic to the fusion protein, for example, a detection signal, enhanced stability or stabilization of the protein, facilitated oligomerization of the protein, or facilitated purification of the fusion protein. Examples of heterologous proteins useful as fusion proteins include molecules having full-length or partial protein sequence of KmLat1 or PgLat2. Further examples include peptide tags such as histidine tag (6-His), leucine zipper, substrate targeting moieties, signal peptides, and the like. Fusion proteins are also meant to encompass variants and derivatives of KmLat1 or PgLat2 polypeptides that are generated by conventional site-directed mutagenesis and more modern techniques such as directed evolution, discussed infra.

"Genetically engineered" refers to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of the desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetic engineering techniques include but are not limited to expression vectors, targeted homologous recombination and gene activation (see, for example, U.S. Pat. No. 5,272,071 to Chappel) and trans activation by engineered transcription factors (sec, for example, Segal et al., 1999, *Proc Natl Acad Sci USA* 96(6):2758-63). Genetic engineering also encompasses any mutagenesis techniques wherein a cell is exposed to chemicals to induce errors in DNA replication or to accelerate gene recombination. The term "spontaneous mutation" refers to mutations that occurs at a much lower rate as a result of genetic recombination or DNA replication errors that occur naturally from generation to generation.

"Heterologous" refers to DNA, RNA and/or polypeptides derived from different organisms or species, for example a bacterial polypeptide is heterologous to yeast.

"Homology" refers to a degree of similarity between polynucleotides, having significant effect on the efficiency and strength of hybridization between polynucleotide molecules. The term also refers to a degree of similarity between polypeptides. Two polypeptides having greater than or equal to about 60% similarity are presumptively homologous.

"Host," "Host cell" or "host cells" refers to cells expressing a heterologous polynucleotide molecule: The term "heterologous" means non-native. For instance, when a gene that is not normally expressed in an organism is introduced and expressed in that host organism, such an expression is heterologous. Host cells of the present disclosure express polynucleotides encoding KmLAT1 or PgLAT2 or a fragment thereof. Examples of suitable host cells useful in the present disclosure include, but are not limited to, prokaryotic and eukaryotic cells. Specific examples of such cells include bacteria of the genera *Escherichia, Bacillus*, and *Salmonella*, as well as members of the genera *Pseudomonas, Streptomyces*, and *Staphylococcus*; fungi, particularly filamentous fungi such as *Trichoderma* and *Aspergillus, Phanerochaete Chrysosporium* and other white rot fungi; also other fungi including *Fusaria*, molds, and yeast including *Saccharomyces* sp., *Pichia* sp., and *Candida* sp. and the like; plants e.g. *Arabidopsis*, cotton, barley, tobacco, potato, and aquatic plants and the like; SF9 insect cells (Summers and Smith, 1987, *Texas Agriculture Experiment Station Bulletin*, 1555), and the like. Other specific examples include mammalian cells such as human embryonic kidney cells (293 cells), Chinese hamster ovary (CHO) cells (Puck et al., 1958, *Proc. Natl. Acad. Sci. USA* 60, 1275-1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), murine myeloma cells such as P3/NSI/1-Ag4-1 (ATCC TIB-18), P3X63Ag8 (ATCC TIB-9), SP2/0-Ag14 (ATCC CRL-1581) and the like. The most preferred host is *Saccharomyces cerevisiae*.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

"Identity" refers to a comparison of two different DNA or protein sequences by comparing pairs of nucleic acid or amino acids within the two sequences. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482-489.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in this context include single and double stranded DNA, single and double stranded RNA, and hybrid molecules having mixtures of single and double stranded DNA and RNA. The polynucleotides may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein makes Up for at least about 90% of a composition. In other words, it refers to a target protein that is free from at least 5-10% of contaminating proteins. Purification of a protein from contaminating proteins may be accomplished using known techniques, including ammonium sulfate or ethanol precipitation, acid precipitation, heat precipitation, anion or cation exchange chromatography, phosphocellulose chromatography, hydrophobic interaction chromatography, affinity chromatography, hydroxylapatite chromatography, size-exclusion chromatography, and lectin chromatography. Various protein purification techniques are illustrated in *Current Protocols in Molecular Biology*, Ausubel et al., eds. (Wiley & Sons, New York, 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al, 1980, *Proc Natl Acad Sci USA* 77:3567; O'Hare et al., 1981, *Proc Natl Acad Sci USA,* 78:1527), the OPT protein that confers resistance to mycophenolic acid (Mulligan & Berg, 1981, *PNAS USA*, 78:2072), the neomycin resistance marker that confers resistance to the aminoglycoside G-418 (Calberre-Garapin et al., 1981, *J Mol Biol,* 150:1), the Hygro protein that confers resistance to hygromycin B (Santerre et al., 1984, *Gene* 30:147), and the Zeocin™ resistance marker (Invitrogen). In addition, the herpes simplex virus thymidine kinase, hypoxanthine-guanine phosphoribosyltransferase and adenine phosphoribosyltransferase genes may be employed in tk⁻, hgprt⁻ and aprt⁻ cells, respectively.

"Transform" means the process of introducing a gene into a host cell. The gone may be foreign in origin, but the gene may also derive from the host. A transformed host cell is termed a "transformant." The introduced gene may be integrated onto the chromosome of the host, or the gene may remain on a stand-alone vector independent of the host chromosomes.

"Variant", as used herein, means a polynucleotide or polypeptide molecule that differs from a reference molecule. Variants may include nucleotide changes that result in amino acid substitutions, deletions, fusions, or truncations in the resulting variant polypeptide when compared to the reference polypeptide.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA. Examples of vectors useful in the methods disclosed herein include, but are not limited to, plasmids, bacteriophages, cosmids, retroviruses, and artificial chromosomes.

For purpose of this disclosure, unless otherwise stated, the techniques used May be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc), *PCR Protocols: A Guide to Methods and Applications* (Innis et al, (1990) Academic Press, San. Diego, Calif.), Culture of Animal Cells: A Manual of Basic Technique, 2$^{nd}$ ed. (R. I. Freshney (1987) Liss, Inc., New York, N.Y.), and *Gene Transfer and Expression Protocols,* pp 1091128, ed. E. J. Murray, The Humana Press Inc., Clifton, N.J.).

Unless otherwise indicated, the term "yeast," "yeast strain" or "yeast cell" refers to baker's yeast, *Saccharomyces cerevisiae*. Other yeast species, such as *Kluyveromyces marxianus* or *Pichia guilliermondii,* are referred to as non-conventional yeast in this disclosure. Strains of *S. cerevisiae,* depository information, and plasmids used for this disclosure are listed in Table 1, 2 and Table 3, respectively. The yeast *kluyveromyces marxianus* CBS-1089 is obtained from the Centraalbureau voor Schimmelcultures (CBS) collection. *Pichia guilliermondii* NRRL Y-2075 is obtained from the Agricultural Research Service Culture Collection (NRRL).

TABLE 1

*S. cerevisiae* Strains Used in this Disclosure

| Strain | Genotype | Plasmids |
|---|---|---|
| BFY001 | MATa ura3-52 trp1-Δ63 his3-Δ200 leu2-Δ1 | |
| BFY002 | MATa ura3-52 trp1-Δ63 his3-Δ200 leu2-Δ1 yhr104w::LEU2 | |
| BFY507 | MATa ura3-52 trp1-Δ63 his3-Δ200 leu2-Δ1 yhr104w::LEU2 adapted for growth on L-arabinose | p138, p42 |
| BFY518 | same as BFY507 | p138 |
| BFY566 | same as BFY518 | p138, p171 |
| BFY590 | same as BFY518 gal2Δ::HIS3 | p138 |
| BFY597 | same as BFY590 | p138, p42 |
| BFY598 | same as BFY590 | p138, p187 |
| BFY012 | same as BFY002 | pBFY004, pBFY013, pBFY012 |
| BFY013 | same as BFY002 | pBFY007, pBFY016, pBFY014 |
| BFY014 | same as BFY002 | pBFY007, pBFY015, pBFY017 |
| BFY015 | same as BFY002 | pBFY005, pBFY016, pBFY019 |
| BFY016 | same as BFY002 | pBFY005, pBFY018, pBFY017 |
| BFY017 | same as BFY002 | pBFY009, pBFY018, pBFY014 |
| BFY018 | same as BFY002 | pBFY009, pBFY015, pBFY019 |
| BFY057 | MATa his3D1 leu2D0 ura3D0 met15D0 gal80D::G418 yhr104w::LEU2 | |
| BFY534 | same as BFY057 | p144, p165 |
| BFY535 | same as BFY057 | p144, pBFY13 |
| BFY605 | same as BFY590 | p244 |
| BFY625 | MATa his3Δ1 leu2Δ0 ura3Δ0 trp1Δ met15Δ0 gal80Δ::G418 adapted for growth on L-arabinose | pBFY12, pBFY13, p138 |
| BFY626 | Same as BFY625 | pBFY12, p138, p204 |

Yeast strains may be grown on liquid or media with 2% agar for solid media. Where appropriate, some amino acids or nucleic acids are purposely left out from the media for plasmid maintenance. Growth conditions are typically 30° C. unless otherwise indicated, with shaking in liquid cultures: Anaerobic conditions are generally more-favorable to metabolize the various sugars to ethanol.

A number of the yeast strains listed in Table 1 have been deposited at the American Type Culture Collection (ATM) in accordance with the provisions of the Budapest Treaty on the International Recognition of the Deposit of Microorganisms for the Purposes of Patent Procedures. In each instance, the yeast strain was deposited by the inventors listed herein on Mar. 16, 2007 at American Type Culture Collection, 10801 University Boulevard, Manassas, Va. 20110 U.S.A.

TABLE 2

Depository Information
Yeast Strain/Accession Number

BFY013/PTA-8258
BFY534/PTA-8257
BFY598/PTA-8256
BFY626/PTA-8255

TABLE 3

Plasmids Used in this Disclosure

| Plasmid | Marker and expressed genes |
|---|---|
| p42 | URA3, GAL2 over-expression |
| p138 | TRP1, *B. subtilis* araA, *E. coli* araB, *E. coli* araD |
| p144 | *E. coli* araB, D; *B. subtilis* araA in pBFY012 |
| p165 | HIS3, GAL2 over-expression |
| p171 | HIS3, 8.8 kb *K. marxianus* genomic DNA fragment |
| p187 | URA3, KmLAT1 over-expression plasmid |
| p204 | HIS3, PgLAT2 over-expression plasmid |
| p244 | URA3, PgLAT2 over-expression plasmid |
| pBFY004 | control 2μ vector with PGK promoter, GAL10 terminator and Trp1 marker |
| pBFY005 | *E. coli* araB in pBFY004 |
| pBFY007 | *E. coli* araA in pBFY004 |
| pBFY009 | *E. coli* araD in pBFY004 |
| pBFY012 | control 2μ vector with PGK promoter, GAL10 terminator and Ura3 marker |
| pBFY013 | control 2μ vector with PGK promoter, GAL10 terminator and His3 marker |
| pBFY014 | *E. coli* araB in pBFY012 |
| pBFY015 | *E. coli* araB in pBFY013 |
| pBFY016 | *E. coli* araD in pBFY013 |
| pBFY017 | *E. coli* araD in pBFY012 |
| pBFY018 | *E. coli* araA in pBFY013 |
| pBFY019 | *E. coli* araA in pBFY012 |

Yeast cells may be grown in rich media YPD or minimum media conventionally used in the field. YPD medium contains about 1% yeast extract, 2% peptone and 2% dextrose. Yeast minimum media typically contains 0.67% of yeast nitrogen base ("YNB") without amino acids supplemented with appropriate amino acids or purine or pyrimidine bases. An amount of sugar, typically 2% unless otherwise indicated, may be used as carbon source, including glucose (dextrose), galactose, maltose or L-arabinose among others. Adaptation for growth oil L-arabinose is performed as described in for example, Becker and Boles (2003) with modifications as detailed in Example 3.

Over-expression plasmids are constructed by cloning the gene for over-expression downstream of the *S. cerevisiae* PGK1 or TDH3 promoter in a 2μ-based vector. Construction of a DNA library is detailed in the Examples. Note that other like *S. cerevisiae* promoters can also be used for overexpression, including ADH112, PDC1, PGII, etc.

*E. coli* cells may be grown in LB liquid media or on LB agar plates supplemented with ampicillin at 100 μg/ml as needed. Transformation of *E. coli* DH5α is by electrotransformation according to a protocol by Invitrogen (Invitrogen 11319-019). After transformation, the bacterial cells are plated on LB plates containing 100 μg/ml ampicillin for selection. Transformation of *S. cerevisiae* was performed using a DMSO-enhanced lithium-acetate procedure as described with the following modifications (Hill et al., 1991). Cells are harvested and initially washed in water, 600 μl of PEG4000 solution is added and 70 μl DMSO is added just prior to heat shocking. Cells are heat-shocked for 15 min at 42° C. and the last wash step is skipped. Cells are resuspended in 10 mM TE solution and plated.

Yeast DNA is isolated using the Easy DNA kit according to manufacturer's protocol (Invitrogen, K1800-01). DNA manipulations and library construction are performed as described in Molecular Cloning: A Laboratory Manual (1989), except otherwise specifically indicated in this disclosure. Plasmids are cured from yeast by growing the strain in rich non-selective media overnight followed by plating on non-selective media. Isolated colonies are replica plated to screen for loss of selective markers. Plasmid rescue is performed by transforming isolated yeast DNA into *E. coli* followed by isolation and characterization, *E. coli* plasmid isolation is accomplished using plasmid spin mini-prep kit according to the manufacturer's manual (Qiagen, 27106). PCR-based chromosomal walking is performed using the Universal Genome Walker Kit as described (BD Biosciences, K1807-1).

For the transport assays, cells may be grown in minimal media supplemented with 20 g/L of L-arabinose. Cells are collected in mid-growth and washed twice before suspension in water at 30 mg/ml. Uptake of L-(1-$^{14}$C)arabinose (54 mCi/mmol, Moravek Biochemicals Inc.) or D-(1-$^{14}$C) galactose (57 mCi/mmol, Amersham Biosciences) is measured as previously described by Stambuk et al. (2003). Assays are performed in 30 seconds to maintain initial rates after appropriate experiments to ensure uptake is linear for at least 1 minute. Transport activity is described as nano-moles of labeled sugar transported per mg cell dry weight per minute. Inhibition and competition assays are performed as previously described by Stambuk et al, (2003).

Sequencing results showed that the KmLAT1 gene contains an ORF of 1668 bp in length. The predicted amino acid sequence of KmLAT1 shares homology with high-affinity glucose transporters, in particular, with HGT1 from *K. lactis* (Table 4). KmLAT1 transporter shows a much higher similarity with high-affinity glucose transporters from non-conventional yeast than with transporter proteins encoded by the bacterial araE gene or hexose transporters from *S. cereviiae* (FIG. 1).

TABLE 4

Properties and similarities of KmLat1 to other sugar transporters.

| gene | Predicted protein (no. of aa/no. of kDa) | pI of protein | Predicted transmembrane regions | Degree of identity (%)/ similarity (%) | Organism | Putative function of gene product |
|---|---|---|---|---|---|---|
| KmLatI | 556/ 61.3 | 8.22 | 12 | — | *K. marxianus*[1] | L-arabinose transporter |
| KlHgtI | 551/ 60.8 | 5.76 | 12 | 77/89 | *K. lactis*[2] | high affinity glucose transporter |
| AEL042Cp | 547/ 59.8 | 8.82 | 12 | 65/82 | *A. gossypii*[3] | putative hexose transporter |
| DEHA0E01738g | 545/ 61.1 | 5.55 | 12 | 52/70 | *D. hansenii*[4] | hexose transporter |

TABLE 4-continued

Properties and similarities of KmLat1 to other sugar transporters.

| gene | Predicted protein (no. of aa/no. of kDa) | pI of protein | Predicted transmembrane regions | Degree of identity (%)/ similarity (%) | Organism | Putative function of gene product |
|---|---|---|---|---|---|---|
| CaHgt1 | 545/ 60.7 | 8.05 | 12-13 | 50/71 | C. albicans[5] | putative hexose transporter |
| CaHgt2 | 545/ 60.4 | 8.48 | 12-14 | 51/71 | C. albicans[6] | putative hexose transporter |

Accession numbers:
1: Not yet assigned,
2: 1346290,
3; AEL042C,
4: DEHA0E01738g,
5; CAA76406,
6: orfl9.3668

Figure 2:
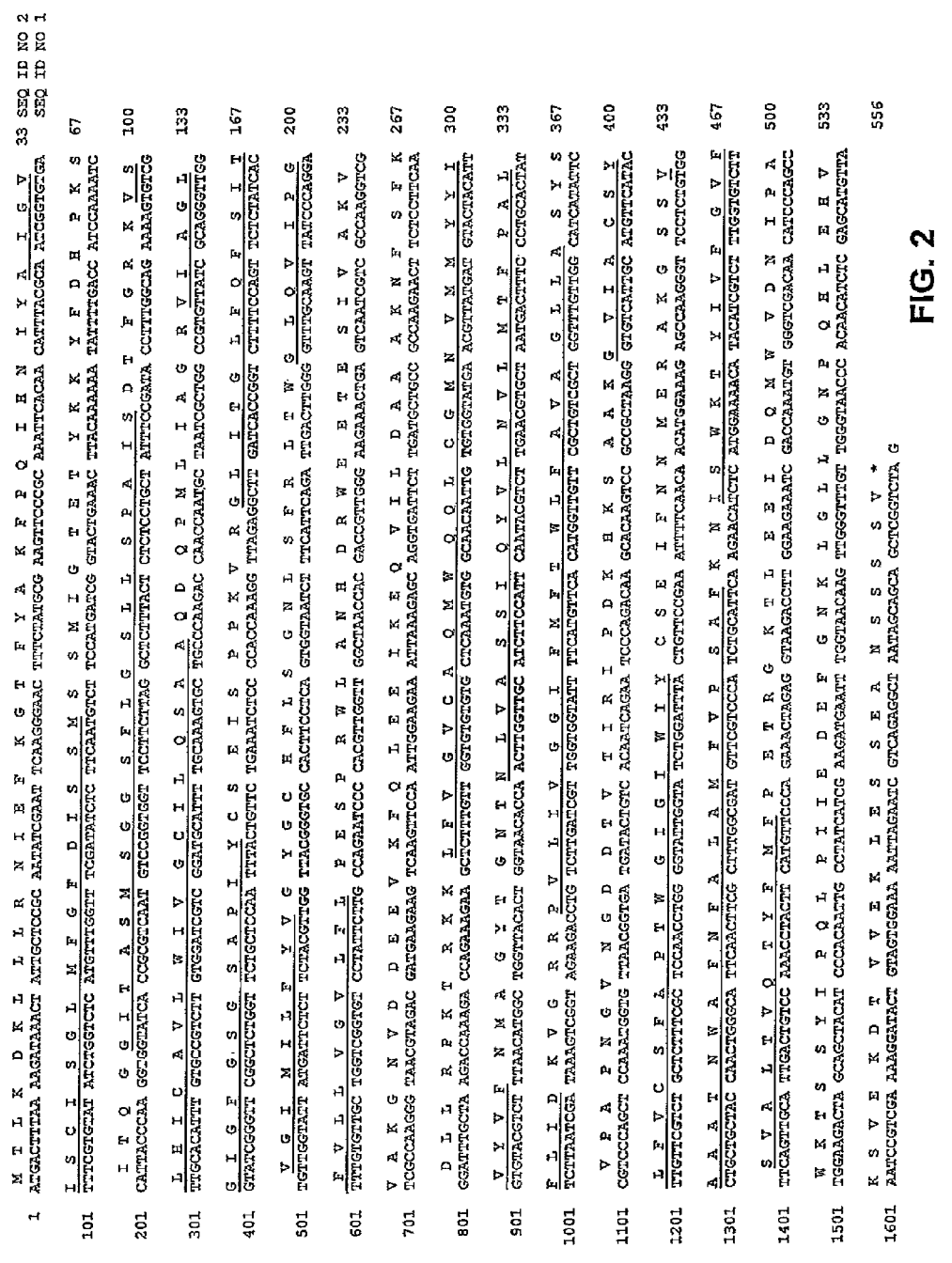

Transmembrane regions predicted for KmLat1 and PgLat2 by the software Tmpred shows 12 transmembrane regions with a larger intercellular loop between regions 6 and 7 (FIG. 2) (See Hofmann et al, 1993), typical of GAL2 and other yeast sugar transporters having 10-12 transmembrane regions (See e.g., Alves-Araujo et al., 2004; Day et al., 2002; Kruckeberg et al., 1996; Pina et al., 2004; and Weierstall et al. 1999).

Like other members of the transporter family, and in particular sugar transporters, KmLat1 and PgLat2 polypeptides are useful in facilitating the uptake of various sugar molecules into the cells. It is envisioned that KmLat1 or PgLat2 polypeptides could be used for other purposes, for example, in analytical instruments or other processes where uptake of sugar is required. KmLat1 or PgLat2 polypeptides may be used alone or in combination with one or more other transporters to facilitate the movement of molecules across a membrane structure, which function may be modified by one skilled in the relevant art, all of which are within the scope of the present disclosure.

The KmLAT1 polypeptides include isolated polypeptides having an amino acid sequence as shown below in Example 2; and in SEQ ID NO:2, as well as variants and derivatives, including fragments, having substantial sequence similarity to the amino acid sequence of SEQ ID NO:2 and that retain any of the functional activities of KmLAT1, PgLAT2 Polypeptides include isolated polypeptides having an amino acid sequence as shown below in Example 5; and in SEQ ID NO:4, as well as variants and derivatives, including fragments, having substantial sequence similarity to the amino acid sequence of SEQ ID NO:4 and that retain any of the functional activities of PgLAT2. The functional activities of the KmLAT1 or PgLAT2 polypeptides include but are not limited to transport of L-arabinose across cell membrane. Such activities may be determined, for example, by subjecting the variant, derivative, or fragment to a arabinose transport assay as detailed, for example in Example 4.

Variants and derivatives of KmLAT1 or PgLAT2 include, for example, KmLAT1 or PgLAT2 polypeptides modified by covalent or aggregative conjugation with other chemical moieties, such as glycosyl groups, polyethylene glycol (PSG) groups, lipids, phosphate, acetyl groups, and the like.

The amino acid sequence of KmLAT1 or PgLAT2 polypeptides is preferably at least about 60% identical, amore preferably at least about 70% identical, more preferably still at least about 80% identical, and in some embodiments at least about 90%, 95%, 96%, 97%, 98%, and 99% identical, to the KmLAT1 and PgLAT2 amino acid sequences of SEQ ID NO: 2 and SEQ ID NO: 4, respectively. The percentage sequence identity, also termed homology (see definition above) may be readily determined, for example, by comparing the two polypeptide sequences using any of the computer programs commonly employed for this purpose, such as the Gap program (Wisconsin Sequence Analysis Package, Version 8 for Unix, Genetics Computer Group, University Research Park, Madison, Wis.), which uses the algorithm of Smith and Waterman, 1981, Adv. Appl. Math. 2; 482-489.

Variants and derivatives of the KmLAT1 or PgLAT2 polypeptides may further include, for example, fusion proteins formed of a KmLAT1 or PgLAT2 polypeptide and another polypeptide. Fusion protein may be formed between a fragment of the KmLAT1 polypeptide and another polypeptide, such that the fusion protein may retain none or only part of the activities normally performed by the full-length KmLAT1 or PgLAT2 polypeptide. Preferred polypeptides for constructing the fusion protein include those that facilitate purification or oligomerization, or those that enhance KmLAT1 or PgLAT2 stability and/or transport capacity or transport rate for sugars, especially for arabinose. Preferred polypeptides may also include those that gain enhanced transport capability when fused with KmLAT1, PgLAT2 or fragments thereof.

KmLAT1 or PgLAT2 variants and derivatives may contain conservatively substituted amino acids, meaning that one or more amino acid may be replaced by an amino acid that does not alter the secondary and/or tertiary structure of the polypeptide. Such substitutions may include the replacement of an amino acid, by a residue having similar physicochemical properties, such as substituting one aliphatic residue (Ile, Val, Leu, or Ala) for another, or substitutions between basic residues. Lys and Arg, acidic residues Glu and Asp, amide residues Gin and Asn, hydroxyl residues Ser and Tyr, or aromatic residues Phe and Tyr. Phenotypically silent amino acid exchanges are described more fully in Bowie et al, 1990. In addition, functional KmLAT1 or PgLAT2 polypeptide variants include those having amino acid substitutions, deletions, or additions to the amino acid sequence outside functional regions of the protein. Techniques for making these substitutions and deletions are well known in the art and include, for example, site-directed mutagenesis.

The KmLAT1 or PgLAT2 polypeptides may be provided in an isolated form, or in a substantially purified form. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. Preferably, protein chromatography is employed for purification.

A preferred form of KmLAT1 or PgLAT2 polypeptides is that of recombinant polypeptides expressed by suitable hosts. In one preferred embodiment, when heterologous expression of KmLAT1 or PgLAT2 is desired, the coding sequences of KmLAT1 or PgLAT2 may be modified in accordance with the codon usage of the host. Such modification may result in increase protein expression of a foreign in the host. Furthermore, the hosts may simultaneously produce other transporters such that multiple transporters are expressed in the same cell, wherein the different transporters may form oligomers to transport the same sugar. Alternatively, the different transporters may function independently to transport different sugars. Such recombinant cells may be useful in crude fermentation processing or in other industrial processing.

KmLAT1 or PgLAT2 polypeptides may be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide may be any molecule or compound, including metal ions (for example, metal affinity columns), antibodies, antibody fragments, or any protein or peptide that preferentially binds the heterologous peptide to permit purification of the fusion protein.

KmLAT1 or PgLAT2 polypeptides may be modified to facilitate formation of KmLAT1 or PgLAT2 oligomers. For example, KmLAT1 polypeptides may be fused to peptide moieties that promote oligomerization, such as leucine zippers and certain antibody fragment polypeptides, for example, Fe polypeptides. Techniques for preparing these fusion proteins are known, and are described, for example, in WO 99/31241 and in Cosman et. al., 2001. Fusion to an Fe polypeptide offers the additional advantage of facilitating purification by affinity chromatography over Protein A or Protein G columns, Fusion to a leucine-zipper (LZ), for example, a repetitive heptad repeat, often with four or five leucine residues interspersed with other amino acids, is described in Landschultz et al., 1988.

It is also envisioned that an expanded set of variants and derivatives of KmLAT1 or PgLAT2 polynucleotides and/or polypeptides may be generated to select for useful molecules, where such expansion is achieved not only by conventional methods such as site-directed mutagenesis but also by more modern techniques, either independently or in combination.

Site-directed-mutagenesis is considered an informational approach to protein engineering and may rely on high-resolution crystallographic structures of target proteins for specific amino acid changes (van den Burg et. al. 1998). For example, modification of the amino acid sequence of KmLAT1 or PgLAT2 polypeptides may be accomplished as is known in the art, such as by introducing mutations at particular locations by oligonucleotide-directed mutagenesis. Site-directed-mutagenesis may also take advantage of the recent advent of computational methods for identifying site-specific changes for a variety of protein engineering objectives (Hellinga, 1998).

The more modern techniques include, but are not limited to, non-informational mutagenesis techniques (referred to generically as "directed evolution"). Directed evolution, in conjunction with high-throughput screening, allows testing of statistically meaningful variations in protein conformation (Arnold, 1998). Directed evolution technology may include diversification methods similar to that described by Crameri et al. (1998), site-saturation mutagenesis, staggered extension process (StEP) (Zhao et al., 1998), and DNA synthesis/reassembly (U.S. Pat. No. 5,965,408).

Fragments of the KmLAT1 or PgLAT2 polypeptide may be used, for example, to generate specific anti-KmLAT1 antibodies. Using known selection techniques, specific epitopes may be selected and used to generate monoclonal or polyclonal antibodies, Such antibodies have utility in the assay of KmLAT1 or PgLAT2 activity as welt as in purifying recombinant KmLAT1 or PgLAT2 polypeptides from genetically engineered host cells.

The disclosure also provides polynucleotide molecules encoding the KmLAT1 or PgLAT2 polypeptides discussed above, KmLAT1 or PgLAT2 polynucleotide molecules include polynucleotide molecules having the nucleic acid sequence shown in SEQ ID NO:1 and SEQ ID NO:3, respectively; polynucleotide molecules that hybridize to the nucleic acid sequence of SEQ ID NO:1 and SEQ ID NO:3, respectively, under high stringency hybridization conditions (for example, 42°, 2.5 hr., 6×SCC, 0.1% SDS); and polynucleotide molecules having substantial nucleic acid sequence identity with the nucleic acid sequence of SEQ ID NO:1 and SEQ ID NO:3, respectively. It will be appreciated that such polynucleotide molecules also broadly encompass equivalent substitutions of codons that may be translated to produce the same amino acid sequences, truncated fragments of the polynucleotide molecules, and polynucleotide molecules with a high incidence of homology, such as 90%, 95%, 96%, 97%, 98%, or 99% or more homology with respect to what is disclosed.

The KmLAT1 or PgLAT2 polynucleotide molecules of the disclosure are preferably isolated molecules encoding the KmLAT1 or PgLAT2 polypeptide having an amino acid sequence as shown in SEQ ID NO:2 and SEQ ID NO:4, respectively, as well as derivatives, variants, and useful fragments of the KmLAT1 or PgLAT2 polynucleotide. The KmLAT1 or PgLAT2 polynucleotide sequence may include deletions, substitutions, or additions to the nucleic acid sequence of SEQ ID NO:1 and SEQ ID NO:3, respectively.

The KmLAT1 or PgLAT2 polynucleotide molecule may be cDNA, chemically synthesized DNA, DNA amplified by PCR, RNA, or combinations thereof. Due to the degeneracy of the genetic code, two DNA sequences may differ and yet encode identical amino acid sequences. The present disclosure thus provides an isolated polynucleotide molecule having a KmLAT1 or PgLAT2 nucleic acid sequence encoding KmLAT1 or PgLAT2 polypeptide, wherein the nucleic acid sequence encodes a polypeptide having the complete amino acid sequences as shown in SEQ ID NO:2 and SEQ ID NO:4, respectively, or variants, derivatives, and fragments thereof.

The KmLAT1 or PgLAT2 polynucleotides of the disclosure have a nucleic acid sequence that is at least about 60% identical to the nucleic acid sequence shown in SEQ ID NO:1 and SEQ ID NO:3, respectively, in some embodiments at least about 70% identical to the nucleic acid sequence shown in SEQ ID NO: 1 and SEQ ID NO: 3, respectively, at least, about 80% identical to the nucleic acid sequence shown in SEQ ID NO:1 and SEQ ID NO:3, respectively, and in other embodiments at least about 90%-95%, 96%, 97%, 98%, 99%% identical to the nucleic acid sequence shown in SEQ ID NO: 1 and SEQ ID NO:3, respectively, Nucleic acid sequence identity is determined by known methods, for example by aligning two sequences in a software program such as the BLAST program (Altschul, S. F. et al. (1990) J. Mol. Biol. 215:403-419, from the National Center for Biotechnology Information (http://www.ncbi.nlm.nih.gov/BLAST/).

The KmLAT1 or PgLAT2 polynucleotide molecules of the disclosure also include isolated polynucleotide molecules having a nucleic acid sequence that hybridizes under high stringency conditions (as defined above) to a the nucleic acid sequence shown in SEQ ID NO: 1 and SEQ ID NO:3, respectively. Hybridization of the polynucleotide is to at least about 15 contiguous nucleotides, or at least about 20 contiguous nucleotides, and in other embodiments at least about 30 contiguous nucleotides, and in still other embodiments at least about 100 contiguous nucleotides of the nucleic acid sequence shown in SEQ ID NO:1 and SEQ ID NO:3, respectively.

Useful fragments of the KmLAT1 or PgLAT2 polynucleotide molecules described herein, include probes and primers. Such probes and primers may be used, for example, in PCR methods to amplify and detect the presence of KmLAT1 or PgLAT2 polynucleotides in vitro, as well as in Southern and Northern blots for analysis of KmLAT1 or PgLAT2. Cells expressing the KmLAT1 or PgLAT2 polynucleotide molecules may also be identified by the use of such probes. Methods for the production and use of such primers and probes are known. For PCR, 5' and 3' primers corresponding to a region at the termini of the KmLAT1 or PgLAT2 polynucleotide molecule may be employed to isolate and amplify the KmLAT1 or PgLAT2 polynucleotide using conventional techniques.

Other useful fragments of the KmLAT1 or PgLAT2 polynucleotides include antisense or sense oligonucleotides comprising a single-stranded nucleic acid sequence capable of binding to a target KmLAT1 or PgLAT2 mRNA (using a sense strand), or DNA (using an antisense strand) sequence.

The present disclosure also provides vectors containing the polynucleotide molecules, as well as host cells transformed with such vectors. Any of the polynucleotide Molecules of the disclosure may be contained in a vector, which generally includes a selectable marker and an origin of replication, for propagation in a host. The vectors may further include suitable transcriptional or translational regulatory sequences, such as those derived from a mammalian, fungal, bacterial, viral, or insect genes, operably linked to the KmLAT1 or PgLAT2 polynucleotide molecule. Examples of such regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a KmLAT1 or PgLAT2 DNA sequence if the promoter nucleotide sequence directs the transcription of the KmLAT1 or PgLAT2 sequence.

Selection of suitable vectors for the cloning of KmLAT1 or PgLAT2 polynucleotide molecules encoding the KmLAT1 or PgLAT2 polypeptides of this disclosure depends upon the host cell in which the vector will be transformed, and, where applicable, the host cell from which the target polypeptide is to be expressed. Suitable host cells for expression of KmLAT1 or PgLAT2 polypeptides include prokaryotes, yeast, and higher eukaryotic cells, each of which is discussed below. Selection of suitable combinations of vectors and host organisms is a routine matter from a perspective of skill.

The KmLAT1 or PgLAT2 polypeptides to be expressed in such host cells may also be fusion proteins that include sequences from other proteins. As discussed above, such regions may be included to allow, for example, enhanced functionality, improved stability, or facilitated purification of the KmLAT1 or PgLAT2 polypeptide. For example, a nucleic acid sequence encoding a peptide that binds strongly to arabinose may be fused in-frame to the transmembrane sequence of the KmLAT1 or PgLAT2 polypeptides so that the resulting fusion protein binds arabinose and transports the sugar across the cell membrane at a higher rate than the KmLAT1 or PgLAT2 transporter.

Suitable host cells for expression of target polypeptides include prokaryotes, yeast, and higher eukaryotic cells. Suitable prokaryotic hosts to be used for the expression of these polypeptides include bacteria of the genera *Escherichia*, *Bacillus*, and *Salmonella*, as well as members of the genera *Pseudomonas*, *Streptomyces*, and *Staphylococcus*.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pSPORT vectors, pGEM vectors (Promega, Madison, Wis.), pPROEX vectors (LTI, Bethesda, Md.), Bluescript vectors (Stratagem), and pQB vectors (Qiagen).

KmLAT1 or PgLAT2 may also be expressed in yeast host cells from genera including *Saccharomyces*, *Pichia*, and *Kluveromyces*. Preferred yeast host is *S. cerevisiae*. Yeast vectors will often contain an origin of replication sequence from a 2µ yeast plasmid for high copy vectors and a CEN sequence for a low copy number vector. Other sequences on a yeast vector may include an autonomously replicating sequence (ARS), a promoter region, sequences for polyadenylation, sequences for transcription termination, and a selectable marker gene. Vectors replicable in both yeast and *E. coli* (termed shuttle vectors) are preferred. In addition to the above-mentioned features of yeast vectors, a shuttle vector will also include sequences for replication and selection in *E. coli*.

Insect host cell culture systems may also be used for the expression of KmLAT1 or PgLAT2 polypeptides. The target polypeptides are preferably expressed using a baculovirus expression system, as described, for example, in the review by Luckow and Summers, 1988.

The choice of a suitable expression vector for expression of KmLAT1 or PgLAT2 polypeptides will depend upon the host cell to be used. Examples of suitable expression vectors for *E. coli* include pET, pUC, and similar vectors as is known in the art. Preferred vectors for expression of the KmLAT1 or PgLAT2 polypeptides include the shuttle plasmid pIJ702 for *Streptomyces lividans*, pGAPZalpha-A, B, C and pPICZalpha-A, B, C (Invitrogen) for *Pichia pastoris*, and pFE-1 and pFE-2 for filamentous fungi and similar vectors as is known in the art. The vectors preferred for expression in *S. cerevisiae* are listed in Table 2.

Modification of a KmLAT1 or PgLAT2 polynucleotide molecule to facilitate insertion into a particular vector (for example, by modifying restriction sites), ease of use in a particular expression system or host (for example, using preferred host codons), and the like, are known and are contemplated for use. Genetic engineering methods for the production of KmLAT1 or PgLAT2 polypeptides include the expression of the polynucleotide molecules in cell free expression systems, in host cells, in tissues, and in animal models, according to known methods.

This disclosure also provides reagents, compositions, and methods that are useful for analysis of KmLAT1 or PgLAT2 activity and for assessing the amount and rate of arabinose transport.

The KmLAT1 or PgLAT2 polypeptides of the present disclosure, in whole or in part, may be used to raise polyclonal and monoclonal antibodies that are useful in purifying KmLAT1 or PgLAT2, or detecting KmLAT1 or PgLAT2 polypeptide expression, as well as a reagent tool for characterizing the molecular actions of the KmLAT1 or PgLAT2 polypeptide. Preferably, a peptide containing a unique epitope of the KmLAT1 or PgLAT2 polypeptide is used in preparation of antibodies, using conventional techniques. Methods for the selection of peptide epitopes and production of antibodies are known. See, for example, *Antibodies: A Laboratory Manual*, Harlow and Land (eds.), 1988 Cold Spring Harbor Laboratory Press, Cold Spring Harbor, N.Y.; *Monoclonal Antibodies, Hybridomas: A New Dimension in Biological Analyses*, Kennet et al. (eds.), 1980 Plenum Press, New York.

Agents that modify, for example, to increase or decrease, KmLAT1 or PgLAT2 transport of arabinose or other sugars may be identified by the transport assay described in Example 4, for example. Performing the transport assay in the presence or absence of a test agent permits screening of such agents.

The KmLAT1 or PgLAT2 transport activity is determined in the presence or absence of a test agent and then compared. For instance, a lower KmLAT1 transport activity in the presence of the test agent, than in the absence of the test agent, indicates that the test agent has decreased the activity of the KmLAT1. Stimulators and inhibitors of KmLAT1 or PgLAT2 may be used to augment, inhibit, or modify KmLAT1 or PgLAT2 transport activity, and therefore may have potential industrial uses as well as potential use in further elucidation of the molecular actions of KmLAT1 or PgLAT2.

The KmLAT1 or PgLAT2 polypeptide of the disclosure is an effective arabinose transporter. In the methods of the disclosure, the sugar transporting effects of KmLAT1 or PgLAT2 are achieved by mixing cells expressing KmLAT1 or PgLAT2 with pure sugar or sugar-containing biomass. KmLAT1 or PgLAT2 may also be used in a cell-free system, KmLAT1 or PgLAT2 may be used under other conditions, for example, at elevated temperatures or under acidic pH. Other methods of using KmLAT1 or PgLAT2 to transport sugar, especially arabinose, for fermentation, are envisioned to be within the scope of what is disclosed, KmLAT1 or PgLAT2 polypeptides may be used in any known application currently utilizing a sugar transporter, all of which are within the scope of this disclosure.

It is shown in this disclosure that Gal2p is an effective L-arabinose transporter at high concentrations of arabinose, whereas KmLAT1 or PgLAT2 may be more effective at different concentrations of L-arabinose. Combination of the Gal2p and the two new transporters from non-conventional yeast may be employed to provide complementary transport into *S. cerevisiae* of L-arabinose down to very low residual concentration of arabinose.

It is shown here that combinatorial expression of Gal2p, KmLAT1 and PgLAT2 may enhance the Overall rate and extent of arabinose utilization by recombinant *S. cereviciae* cells expressing these transporters. As shown in Example 8, the doubling time for *S. cereviciae* strain expressing both PgLAT2 and Gal2p is shorter than *S. cereviciae* cells expressing Gal2p alone (15 hours vs. 19 hours), suggesting that L-arabinose uptake may be enhanced by the synergistic effect of PgLAT2 and Gal2p in these cells. Moreover, the PgLAT2 expressing strain appears to grow to a higher overall optical density at saturation, suggesting that this strain was able to utilize the carbon source (L-arabinose) in the medium more completely. This hypothesis is supported by HPLC analysis of the final culture media (Table 5) which indicates that there is significantly less residual L-arabinose in the culture of cells expressing Gal2p and PgLAT2 than in the culture of those expressing Gal2p alone. Thus, heterologous expression of either or both KmLAT1 and PgLAT2 in *S. cereviciae* may enhance arabinose utilization by facilitating arabinose transport when the concentration of arabinose is relatively low.

TABLE 5

Figure 11:
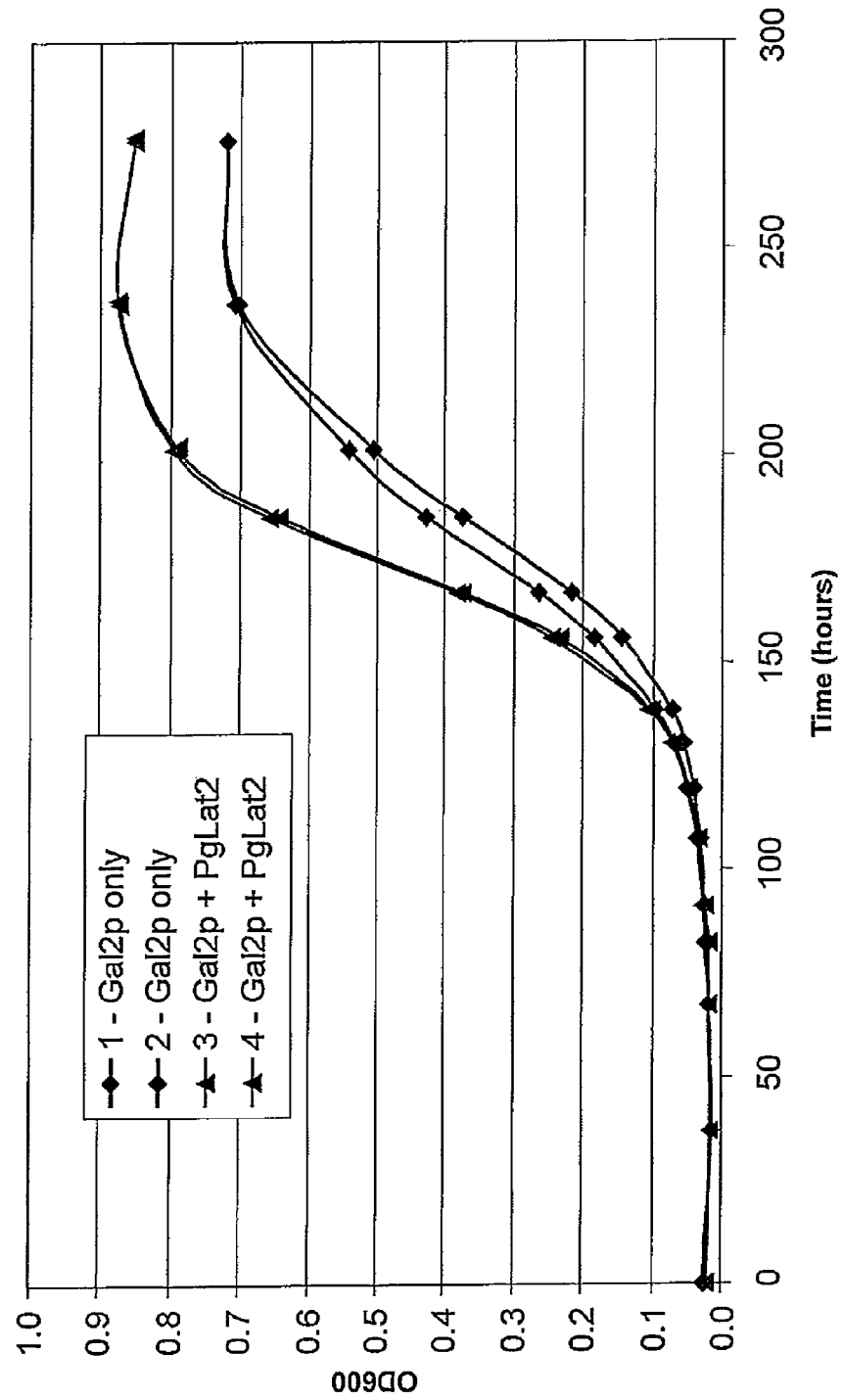
FIG. 11 shows comparison of the growth curves in 0.2% L-arabinose for *S. cerevisiae* cells expressing either. Gal2p alone or both Gal2p and PgLat2. The maximum growth density and growth rate are significantly enhanced in the strain expressing both Gal2p and PgLat2.

Doubling times and HPLC Measurement of Residual Arabinose Concentration in Cultures Described in FIG. 11.

| Flask | Transporters Expressed | Doubling Time (hours) | Final OD$_{600}$ | L-arabinose (g/L) by HPLC |
|---|---|---|---|---|
| 1 | Gal2p only | 19.2 | 0.72 | 0.68 |
| 2 | | 18.6 | 0.72 | 0.67 |
| 3 | Gal2p + PgLat2 | 15.0 | 0.85 | 0.49 |
| 4 | | 14.8 | 0.85 | 0.48 |

*starting L-arabinose concentration 1.89 g/L and media without L-arabinose had an undetectable level (<0.1 g/L).
ND = not determined.

L-arabinose metabolism in bacteria involves three enzymes: L-arabinose isomerase (araA), L-ribulokinase (araB), and L-ribulose-5-p 4-epimerase (araD), which may be collectively referred to as the "araBAD" proteins in this disclosure. The genes encoding these three enzymes may be referred to as the "araBAD" genes in this disclosure. The combined action of these three bacterial proteins convert L-arabinose to Xylulose-5-phosphate (See FIG. 3). *S. cerevisiae* contains the pathway to utilize and ferment the final product xylulose-5-phosphate and produce ethanol under certain conditions (see FIG. 3).

*S. cerevisiae* strain to be used to construct an arabinose fermenting yeast strain preferably possesses Gal$^+$ phenotype. A Gal$^+$ strain is likely to express galactose permease which may facilitate the uptake of arabinose by *S. cerevisiae*.

*S. cerevisiae* typically possesses endogenous aldose reductase ("AR") activity, which may divert arabinose to a pathway different from the one that may lead to the production of ethanol through the action of the bacterial araBAD proteins. Moreover, the arabitol generated by the AR protein may inhibit the isomerase encoded by araA. In order to increase the overall yield of ethanol from arabinose, it is preferable to use an AR-deficient strain to construct the arabinose fermenting yeast of the present disclosure. The AR-deficient strain may be obtained by screening for spontaneous mutations, or preferably by targeted gene disruption or mutation. An example of such gene disruption is detailed in Example 10.

Figure 3:
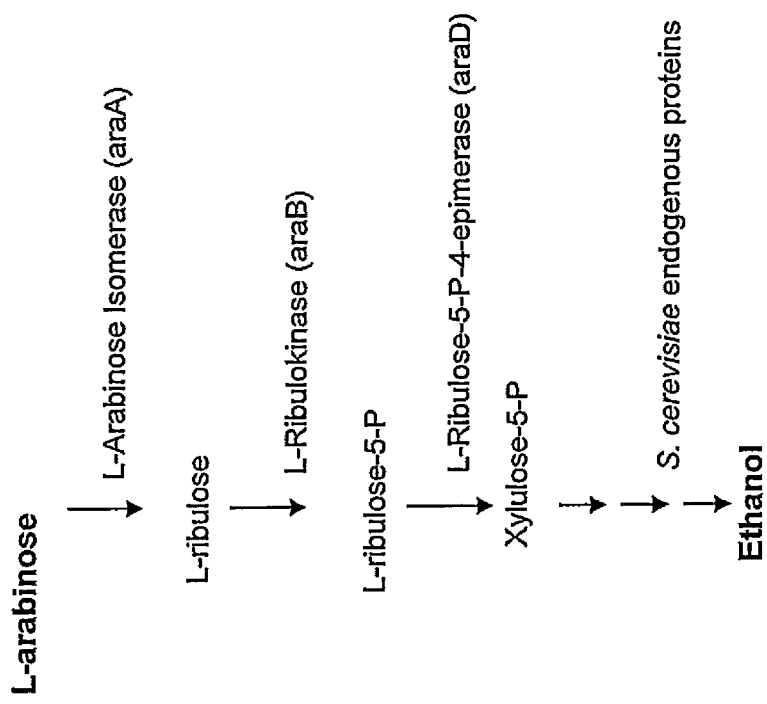
FIG. 3 is a schematic presentation of the arabinose metabolic pathway in recombinant yeast containing proteins encoded by three bacterial genes araB, araA, and araD.

As shown in FIG. 3, the engineered pathway utilizing bacterial araBAD converts L-arabinose to xylulose-5-P that *S. cerevisiae* can convert to ethanol using endogenous enzymatic activities. It is thus desirable to ensure that the arabinose metabolic pathway starting from xylutose to ethanol remains intact in the AR-deficient strain. This may be tested by comparing the growth of the AR-deficient strain with its parental strain on glucose or xylulose. If both strains proliferate at about the same rate on glucose or xylulose, it is likely that the AR gene disruption event has not negatively impacted the catabolism of glucose or xylulose.

The present disclosure also provides a new method to measure arabinose uptake by yeast cells. Traditionally, L-arabinose transport is measured by using radio-labeled substrate. Since aldose reductase, which converts L-arabinose to arabitol, is cytosolic, it is possible to use the formation of new arabitol as an indicator of arabinose uptake. Higher levels of arabitol indicates higher uptake of L-arabinose. To confirm the validity of this method, L-arabinose transport was measured using the traditional $^{14}$C-labeled L-arabinose in various yeast strains with different levels of arabitol formation. These experiments show that the level of arabitol formation corresponds well with the level of L-arabinose uptake.

Using this method, several high arabitol producing strains have been isolated, including two gal80 mutants and two otherwise wildtype strains, which have 3 to 4 folds higher L-arabinose and D-galactose transport activity than the BFY001 originally used to construct the arabinose fermenting strains. Bacterial genes encoding the araBAD proteins may be introduced into these strains to achieve higher rate of arabinose uptake and thus higher overall yield. This result also validates the indirect screening method for strains with higher arabinose transport activity.

Although the present disclosure teaches the introduction of foreign genes such as *E. coli* araBAD genes, into yeast cells, genes from other species encoding proteins that perform the same or similar function as the *E. coli* araBAD proteins, i.e., converting L-arabinose into various intermediates and eventually into ethanol, may be used in place of the *E. coli* araBAD genes (See e.g., Becker and Boles, 2003, using araA from *Bacillus subtilis*). The DNA of the foreign genes may be present in a host cell at one copy, or preferably, in more than one copy. The foreign genes may be under control of a constitutive promoter or an inducible promoter.

The foreign genes may be present as plasmids or minichromosomes in the host yeast cells, or alternatively, the plasmids carrying the foreign genes may be engineered so that the foreign genes are integrated into the chromosomes of the host through genetic recombination. In the latter case, the foreign tends to be maintained after generations, even when the host cells are grown in rich media where no selective pressure is present. By contrast, in the former case where the genes remain on a vector, the genes may be lost after a few generations. Under those circumstances, the host yeast cells are preferably grown in a minimum media supplemented with appropriate amino acids or purine or pyrimidine bases so that a selective pressure helps maintain the plasmids.

Cell-free or whole-cell fermentation may be used to convert arabinose to ethanol. In the whole cell fermentation process, the transformants may be grown on minimum media with appropriate supplementation to maintain the plasmids. The transformant cells are preferably grown on galactose to induce the expression of galactose permease. More preferably, the cells are grown on both arabinose and galactose before the fermentation assays, tri addition, transformant cells can be grown on both arabinose and glucose before the fermentation assays (see FIG. 19).

In the cell-free fermentation system, cells are harvested and the cells are lysed to release enzymes for the conversion of the sugar to ethanol. One bottleneck for a whole-cell fermentation system is the uptake of arabinose by the cells, which may explain its lower overall yield of ethanol than the cell free system. However, whole-cell fermentation is preferred because it is easier to perform. In a whole-cell fermentation system, the cells may be mixed directly with the biomass or other substrates, requiring no extra steps of cell-handling.

In a preferred embodiment, the various arabinose metabolic pathways disclosed here may be introduced into a *S. cerevisiae* strain that have been modified to facilitate its arabinose uptake. Such strain may include but are not limited to strains that express both the Gal2p and one or two of the novel arabinose transporters similar to the ones disclosed here. The expression levels of the array of arabinose transporters may be fine-tuned such that they are commensurate with the rate of arabinose metabolism inside the engineered yeast cells. Most preferably, the expression levels of the transporters may be linked to the arabinose metabolic rate in each cell, such that the arabinose is taken in more rapidly by those cells that convert arabinose to ethanol more efficiently.

The examples herein illustrate the present instrumentalities by way of illustration, and not by limitation. The chemicals, biological agents and other ingredients are presented as typical components or reactants, and the procedures described herein may represent but one of the typical ways to accomplish the goal of the particular experiment. It is understood that various modification may be derived in view of the foregoing disclosure without departing from the spirit of the present disclosure.

Example 1

Cloning of the New Transporter Gene KmLAT1

A *K. marxianus* genomic library was constructed in our yeast vector pBFY13 which contains the yeast 2p origin of replication, a URA3 selection cassette, and a BamHI site located between the PGK1 promoter and GAL10 terminator. After partial digestion of 200 µg of genomic DNA with Sau3AI restriction enzyme, fragments of 2-8 kb in length were gel-isolated and ligated into the BamHI site of pBFY013. This ligation reaction was then transformed into *E. coli* and plated for recovery. Plate counts produced ~3000 cfu's/10 µl of transformed cells and the plasmid DNA from 24 colonies was screened for presence of insert revealing 22 of 24 transformants had an insert ranging from 1 kb to ~8 kb giving an average insert size of 3.2 kb. The transformed cells were scraped from the plates, DNA recovered, and 5 µl was transformed into-competent-BFY518 cells. The strain, BFY518, was cured of the GAL2 over-expression plasmid negating its ability to form colonies on agar plates containing L-arabinose as the sole carbon source enabling restoration of colony formation by complementation with a heterologous L-arabinose transporter. To count the number of transformed yeast cells, 10 µl of the yeast library transformation were plated onto minimal glucose media yet the colonies were so dense that only an estimate of ~5000 colonies was possible. The rest of the transformation mix (~140 µl) was plated onto minimal media containing 2% L-arabinose for selection from which a small amount of background growth was noticed. The plates were then replica plated to fresh L-arabinose minimal media. The total number of cells plated for selection represented ~280,000 transformants representing fold coverage of the 10.7 mb *K. marxianus* genome (See Dujon et al., 2004). Two colonies grew on the replica plates and the plasmid DNA was rescued and re-transformed into BFY518 allowing growth once again on L-arabinose confirming that the *K. marxianus* genomic insert carried on these plasmids was responsible for growth. Restriction analysis suggested both plasmids harbored the same insert of approximately 8.8 kb in size.

Example 2

Sequence Analysis of the KmLAT1 Gene

Figure 4:
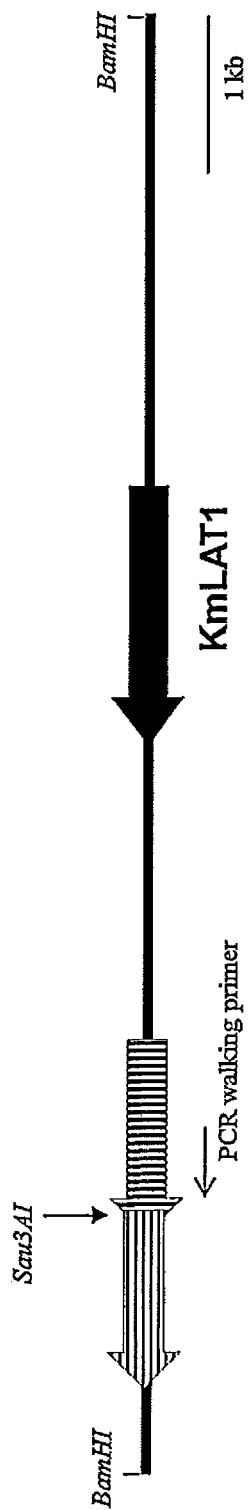
FIG. 4 shows the library insert from genomic *K. marxianus* DNA complements adapted *S. cerevisiae* for growth on L-arabinose. Cloning into the library expression vector is at the indicated BamHI restriction sites. The black block arrow is the L-arabinose transporter ORF responsible for complementation (KmLAT1). The block arrow with vertical stripes is the interrupted transporter ORF. The block arrow with the horizontal stripes is an un-related ORF ligated in place gratuitously during library construction. The Sau3AI restriction site where the transporter ORF was interrupted is shown. The primer used for PCR based genomic walking in *K. marxianus* is shown.

Sequencing results showed that both plasmids had identical inserts of 8838 kb containing two ORFs on the 5' end of the insert. Both of these ORFs showed strong homology to yeast sugar transporters. One transporter ORF was interrupted by a fragment of an unrelated ORF suggesting that recombination of fragments during ligation into the vector occurred in library construction (FIG. 4). Recombination of library fragments during ligation into the vector was shown by PCR walking experiments performed on *K. marxianus* genomic DNA. Walking was performed out of the transporter in a 5' direction and additional transporter sequence including the start codon was recovered rather than the additional sequence from the unrelated ORF. The uninterrupted transporter ORF, termed KmLAT1, was recovered twice more in another subsequent library screening. This ORF was 1668 bp in length and shared homology with high-affinity glucose transporters in particular, HGT1 from *K. lactis* (Table 4) and showed a much closer association with high-affinity glucose transporters from non-conventional yeasts than the bacterial araB genes or *S. cerevisiae* hexose transporters (FIG. 1).

Transmembrane region prediction by the software Tmpred shows 12 transmembrane regions with a larger intercellular loop between regions 6 and 7 (FIG. 2) (See Hofmann et al, 1993), typical of GAL2 and other yeast sugar transporters having 10-12 transmembrane regions (See e.g., Alves-Araujo et al., 2004; Day et al., 2002; Kruckeberg et al., 1996; Pina et al. 2004; and Weierstall et al. 1999).

Example 3

KmLat1 Expressed in *S. cerevisiae* Enables Growth on Arabinose

The coding sequence of KmLAT1 was isolated by PCR from genomic DNA of *K. marxianus* and cloned into a yeast 2μ plasmid under control of the PGK1 promoter of *S. cerevisiae*. This construct was transformed into a GAL2 deleted strain of *S. cerevisiae* adapted to L-arabinose. Briefly, cells are grown in appropriate selective glucose minimal media until saturation then washed and diluted to a starting $OD_{600}$ of 0.2 in minimal media supplemented with 2% L-arabinose. Cultures are incubated until exponential growth is observed then the cultures are diluted twice into the same media for continued growth to establish the final L-arabinose utilizing adapted strain which is purified on streak plates. Control plasmids carrying the yeast GAL2 gene and an empty vector were also used to transform yeast cells.

Figure 5:
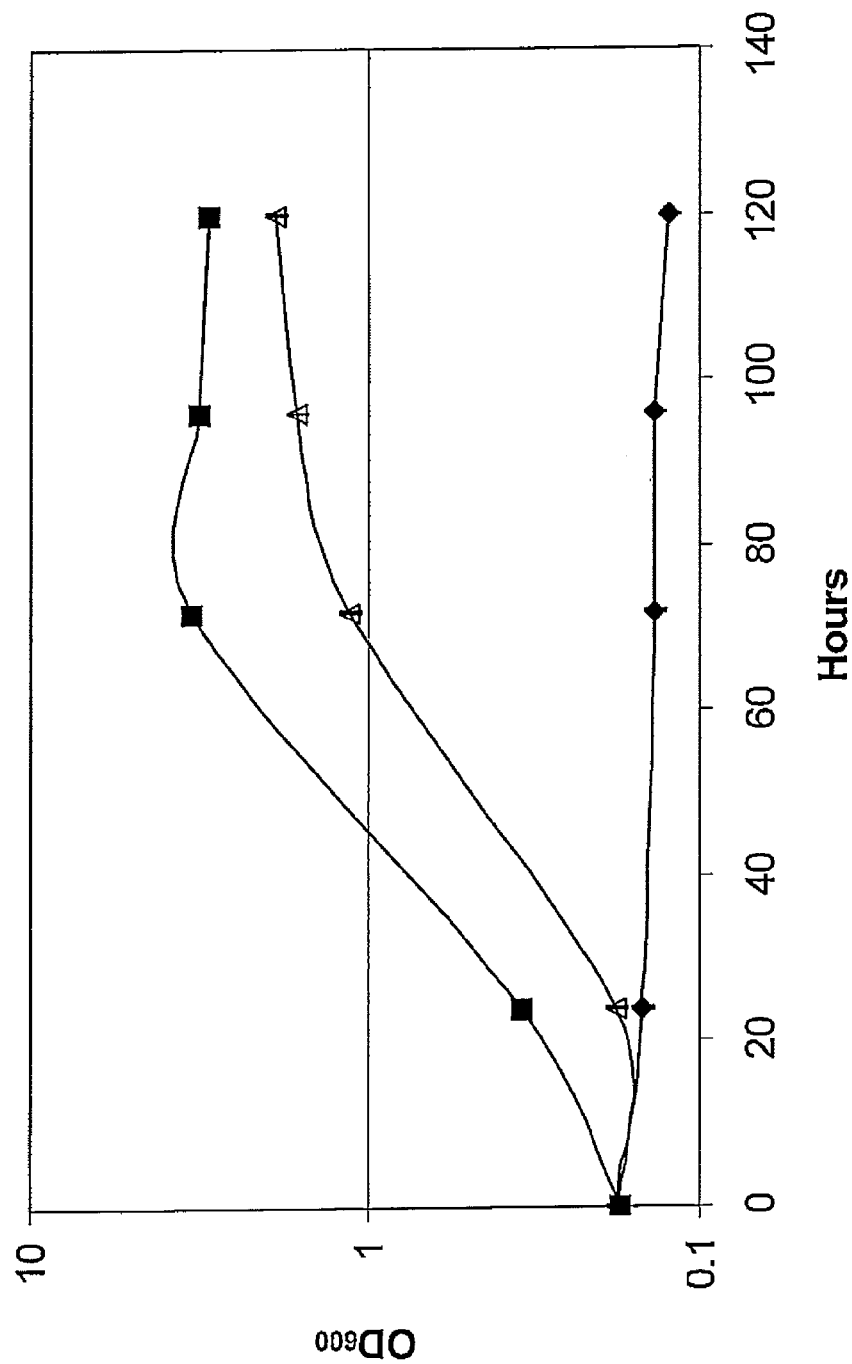
FIG. 5 shows the growth curve of *S. cerevisiae* expressing KmLAT1 (Δ), GAL2 (■) or a control vector (♦) on 2% L-arabinose.

Yeast cells with a 2μ plasmid carrying the KmLAT1 or GAL2 gene or cells with an empty 2μ plasmid were grown with shaking in liquid minimum media containing 2% L-arabinose as the sole carbon source. The $OD_{600}$ of each culture, was measured and monitored by 140 hours. Growth curve results show that KmLat1 is sufficient to support growth on L-arabinose when compared to cells harboring the empty vector which does not show any signs of growth (FIG. 5). This result confirms that the KmLat1 gene encodes an arabinose transporter that enables yeast cells to grow on L-arabinose.

Example 4

Comparison of the Arabinose Transport Kinetics between Gal2 and KmLat1 Expressed in *S. cerevisiae*

Figure 6A:
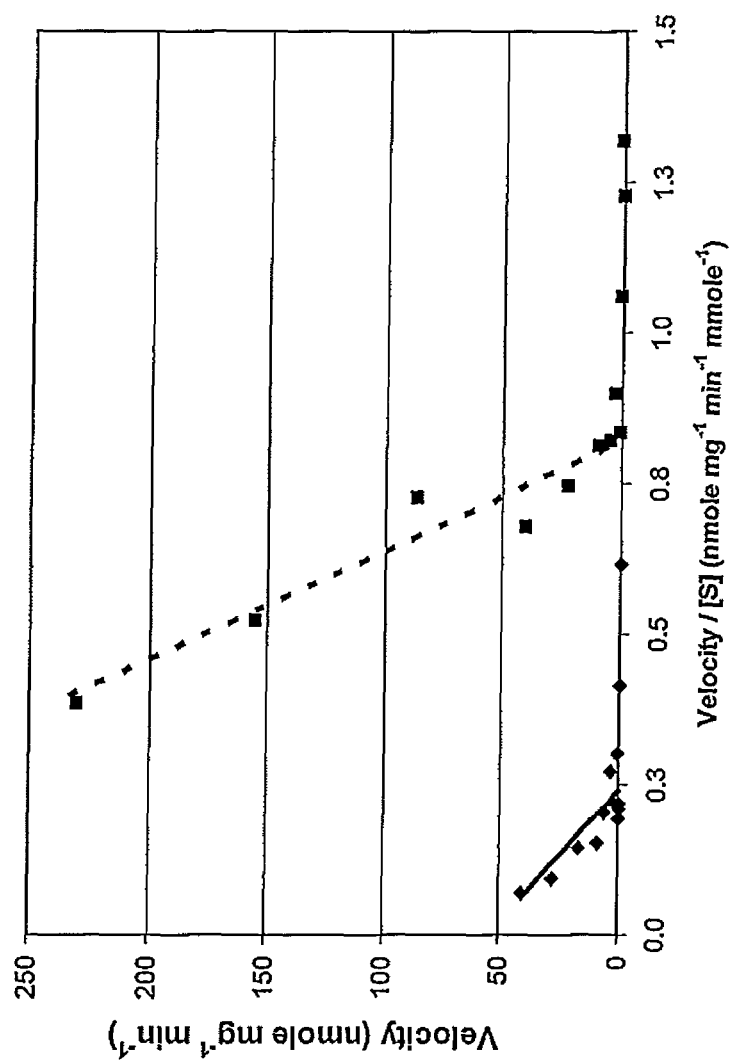
FIG. 6. (A): Eadie-Hofstee plot of L-arabinose uptake by KmLat1 (♦) or Gal2 (■) expressed in *S. cerevisiae* grown on 2% L-arabinose. (B): Comparison of Eadie-Hofstee plots of KmLat1 expressed in *S. cerevisiae* (♦) and wild type transport activity of *K. marxianus* (Δ) both grown on 2% L-arabinose.
Figure 6B:
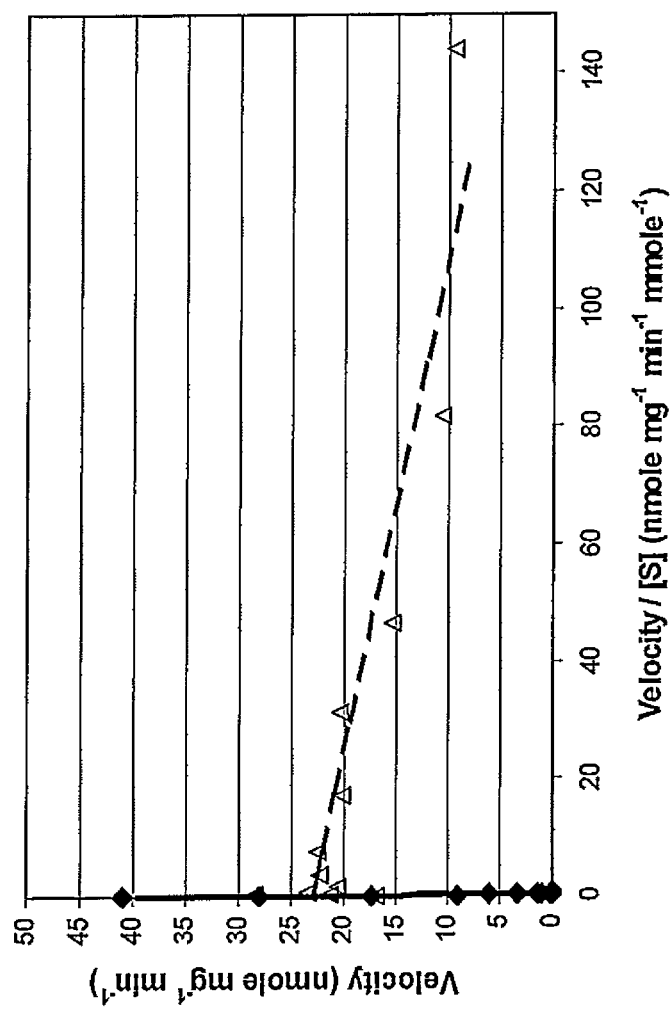

The transport characteristics of the KmLat1 and the Gal2 transporters expressed in *S. cerevisiae* were compared. Both transporters were expressed in a host background adapted for growth on L-arabinose in which the endogenous copy of GAL2 had been entirely replaced with a HIS3 selection marker. The KmLat1 transporter showed a low-affinity transporter having a $K_m$=230 mM and a $V_{max}$=55 nmol/mg·min (FIG. 6A). This is in contrast to the high-affinity active transport activity induced in the wild type *K. marxianus* when grown on 2% L-arabinose (FIG. 6B). These results suggest there are at least 2 transporters in *K. marxianus* that may transport L-arabinose but just the high-affinity activity is induced in the wild type when grown on 2% L-arabinose. Inhibition experiments showed that when KmLat1 is expressed in *S. cerevisiae* it is not significantly inhibited by protonophores such as $NaN_3$, DNP, and CCP. Neither is KmLat1 inhibited by H+-adenosine triphosphatase (ATPase) inhibitors such as DESB and DCCD (Table 6). This is in contrast to the transport activity in wild type *K. marxianus*, suggesting that KmLat1 is a facilitated diffusion permease similar to the Gal2 permease. Competition experiments showed that KmLat1 is out-competed by glucose, galactose, xylose, and maltose when expressed in *S. cerevisiae* (Table 6).

TABLE 6

Effect of Inhibitors or Competing Sugars on the Rate of L-Arabinose Transport in L-Arabinose-Grown *S. cerevisiae* Expressing GAL2 or KmLAT1

| Inhibitor or Competing Sugar | Concentration (mM) | Relative L-arabinose transport (%) Gal2 | KmLat1 |
|---|---|---|---|
| None | NA | 100[a] | 100[c] |
| $NaN_3$ | 10 | 66 | 11 |
| CCCP | 5 | 46 | 61 |
| DCCD | 5 | 69 | 55 |
| DNP | 5 | 72 | 75 |
| DESB | 5 | 81 | 100 |
| None | NA | 100[b] | 100[d] |
| Glucose | 900 | 10 | 17 |
| Galactose | 900 | 3 | 23 |
| Xylose | 900 | 25 | 25 |
| Maltose | 450 | ND | 38 |

[a]Uptake rate was 66.0 nmol mg$^{-1}$ min$^{-1}$ determined with 118 mM labeled L-arabinose.
[b]Uptake rate was 18.9 nmol mg$^{-1}$ min$^{-1}$ determined with 30 mM labeled L-arabinose.
[c]Uptake rate was 7.7 nmol mg$^{-1}$ min$^{-1}$ determined with 118 mM labeled L-arabinose.
[d]Uptake rate was 3.6 nmol mg$^{-1}$ min$^{-1}$ determined with 30 mM labeled L-arabinose.
ND, Not Done.

Transport kinetics of *S. cerevisiae* BFY597 over-expressing the Gal2 permease grown on 2% L-arabinose showed a $K_m$ of 550 mM and a $V_{max}$ of 425 nmol/mg·min for L-arabinose transport (FIG. 6A). Inhibition assays showed a reduction but not a complete inhibition of transport suggestive of facilitated diffusion transport (Table 6). Competition studies showed that glucose, galactose, and xylose significantly reduced L-arabinose transport indicating that these sugars are preferentially transported over L-arabinose (Table 6). The kinetics of galactose transport were also measured in this strain and indicate that Gal2p has a $K_m$ of 25 mM and a $V_{max}$ of 76 nmol/mg·min for galactose transport (data not shown) demonstrating a higher affinity for galactose that would out-compete L-arabinose for transport.

Example 5

Cloning of the New Transporter Gene PgLAT2

Wildtype *Pichia guilliermondii* NRRL Y-2075 was obtained from the Agricultural Research Service Culture Collection (NRRL). *Pichia guilliermondii* cells were grown in minimal media supplemented with 2% L-arabinose, galactose, or xylose. Cells were collected in mid-growth and washed twice in water before suspension in water at about 30 mg/ml. RNA was extracted from the cells using the acid phenol method (Ausubel, et al., Short Protocols in Molecular Biology, John Wiley and Sons, 1999). Briefly, approximately 15 ml of fresh culture was added to about 25 mL of crushed ice and centrifuged at 4° C. for 5 min at 3840×g. Cells were washed twice with cold DEPC-treated water, and the pellets were frozen at −80° C. After the pellets were resuspended in 400 ul TES (10 mM Tris HCl, pH 7.5, 5 mM EDTA, 0.5% SDS), 400 ul of acid phenol was added. The samples were vortexed vigorously for 10 sec, followed by incubation for 30-60 min at 65° C. with occasional vortexing. The tubes with the samples were then chilled on ice and spun for 5 min at 4° C. The aqueous phase was removed and re-extracted with chloroform. The aqueous phase was then ethanol precipitated using 0.1 volume of 3 M sodium acetate (pH 5.3) and two volumes of 100% ethanol. The pellet was washed using 80% ethanol, dried, and resuspended in 50 ul DEPC $H_2O$. Total RNA concentration was quantitated by measuring the $OD_{260}$ and visualized on agarose gels.

RNA purification, synthesis of cDNA, and differential display were performed at GenHunter Corporation according to standard techniques. DNA Bands showing higher levels of expression from arabinose-grown cells relative to xylose- or galactose-grown cells were reamplified using the differential display amplification primers. Direct sequencing was performed on the PCR products using the GenHunter arbitrary primers. In cases that did not yield clean sequence, the amplification products were cloned in the TOPO-TA vector pCR2.1 (Invitrogen) and individual clones were sequenced. Sequences were then compared to the databases using BLASTX analysis and those that showed similarity to known transporters or transporter like proteins were examined further. One of these sequences led to the identification of a novel transporter gene, PgLAT2 from *Pichia guilliermondii*. PgLAT2 gene has an ORF of 1617 nucleotides encoding a protein with a predicted length of 539 amino acids (FIG. 7).

Example 6

Characteristics of Sugar Transport by *Pichia guilliermondii*

The induction of L-arabinose transport in wild type *P. guilliermondii* was examined. Wildtype *Pichia guilliermondii* cells were grown in minimal media supplemented with 2% L-arabinose, galactose, or xylose while BFY605 cells were grown in the same media supplemented with 0.2% L-arabinose. Cells were collected in mid-growth and washed twice in water before suspension in water at about 30 mg/ml. Uptake of L-(1-$^{14}$C)arabinose (54 mCi/mmol, Moravek Biochemicals Inc.), D-(1-$^{14}$C)galactose (57 mCi/mmol, Amersham Biosciences), or D-(1-$^{14}$C)xylose (53 mCi/mmol, Moravek Biochemicals Inc.) was measured as previously described (Stambuk, Franden et al. 2003). Assays were performed in 5, 10, or 30 second periods to maintain initial rates. Appropriate experiments ensured uptake was linear for at least 1 minute. Transport activity was described as nmoles of labeled sugar transported per mg cell dry weight per minute. Inhibition and competition assays were performed as previously described (Stambuk, Franden et al. 2003).

Figure 8:
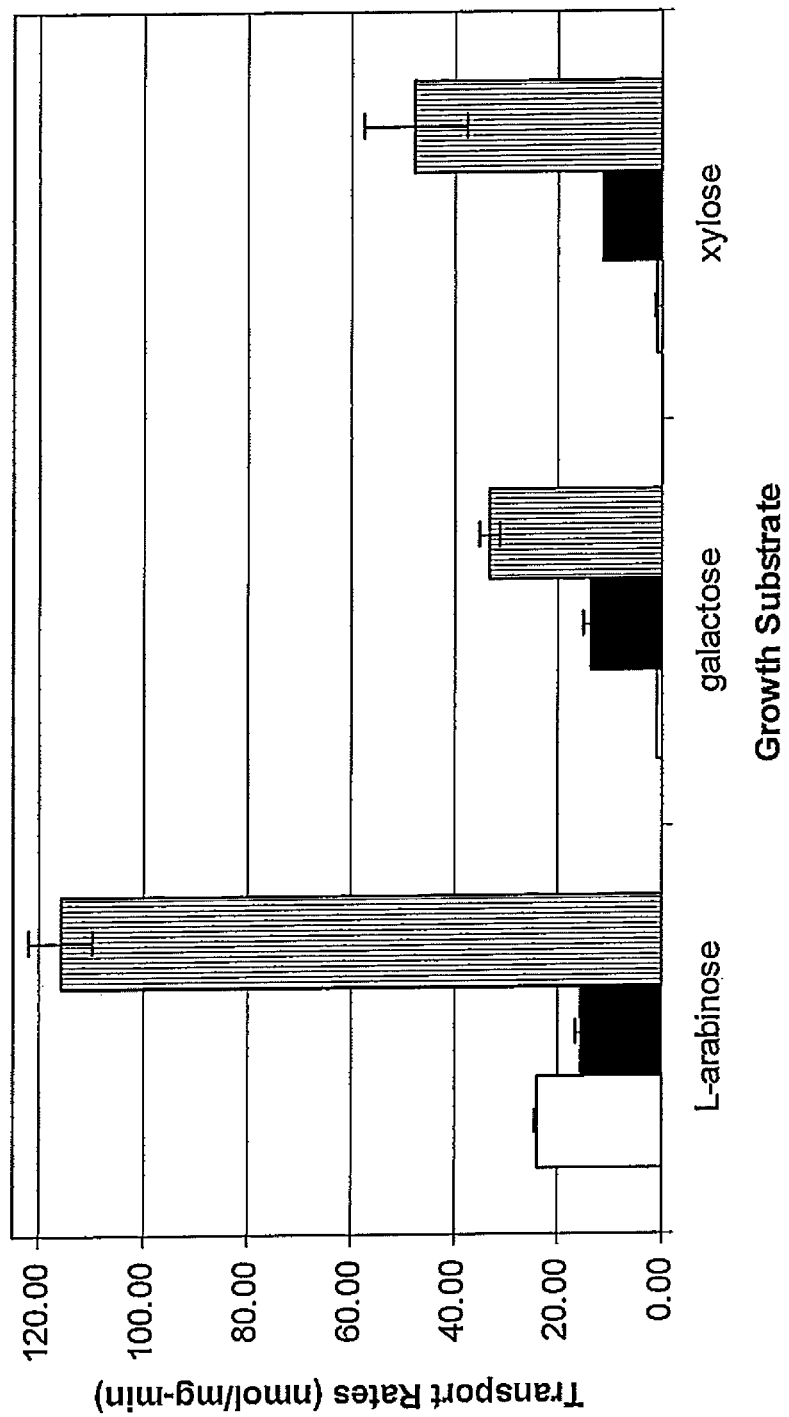
FIG. 8 shows the induction of L-arabinose transport in *P. guilliermondii*. Uptake of 13 mM labeled sugar was assayed for cells grown in minimal media containing 2% L-arabinose, D-galactose or D-xylose. White bars indicate labeled L-arabinose transport. Black bars indicate labeled galactose transport. Bars with vertical stripes indicate labeled xylose transport.
Figure 9:
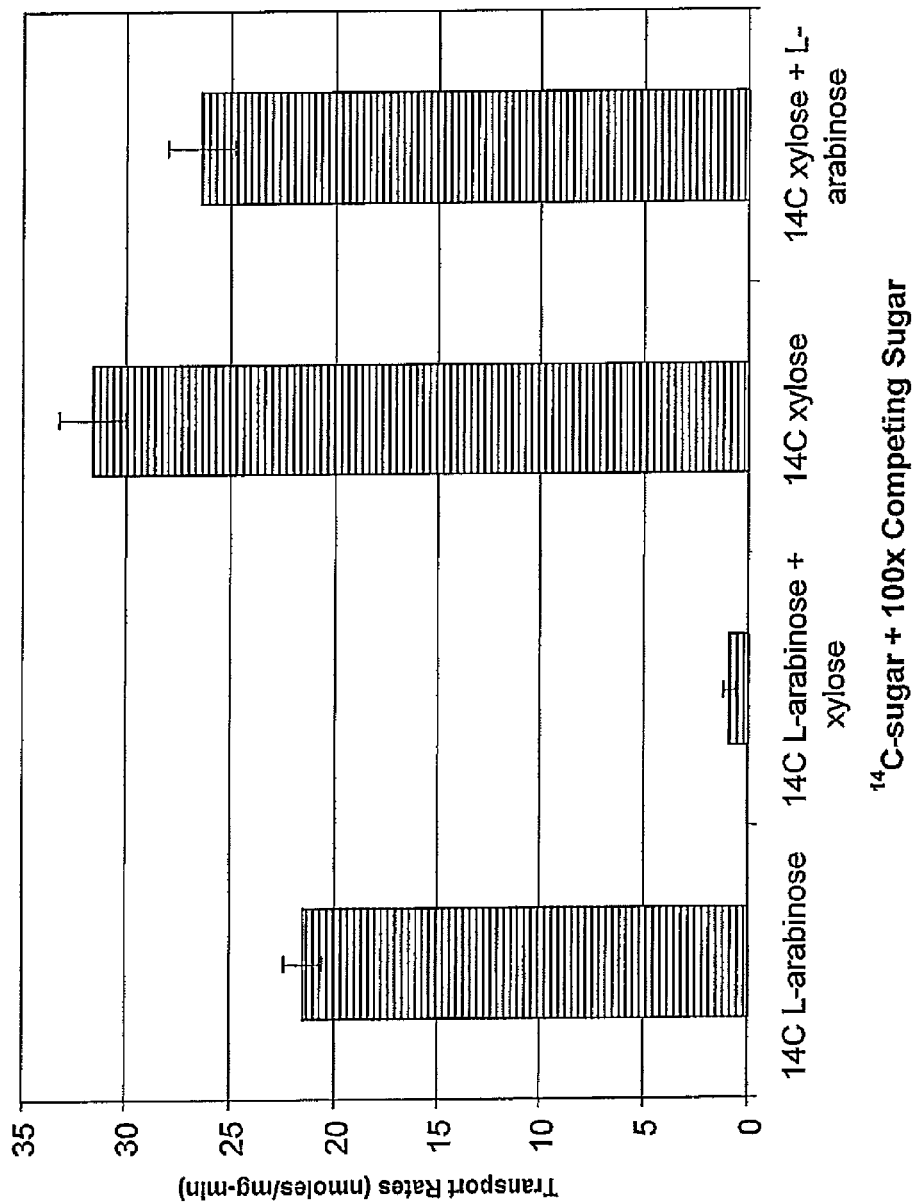
FIG. 9 shows the sugar transport competition analysis in *P. guilliermondii* grown in minimal L-arabinose medium.

Cells grown on L-arabinose were able to transport L-arabinose whereas cells grown on galactose or xylose were not able to transport L-arabinose. Additionally, xylose transport was about double in cells grown in L-arabinose media compared to cells grown in xylose media. Galactose was transported at the same rate independent of growth substrate (FIG. 8). Transport competition between L-arabinose and xylose was also examined. Uptake of labeled L-arabinose was reduced by 96% when 100× un-labeled xylose was included in the transport assay whereas uptake of labeled xylose was only reduced by 16% when 100× un-labeled L-arabinose was included in the assay (FIG. 9). This data suggests that in *P. guilliermondii*, growth on L-arabinose induces expression of a specific transport system capable of transporting L-arabinose and xylose. Additionally, this system preferentially transports xylose at the expense of L-arabinose if both sugars are present and has a higher transport velocity for xylose than the transport system induced when grown on xylose. By contrast, transport activity for L-arabinose is not induced when grown on xylose.

Example 7

Arabinose Transport Kinetics of PgLAT2 Expressed in *S. cerevisiae*

Figure 10:
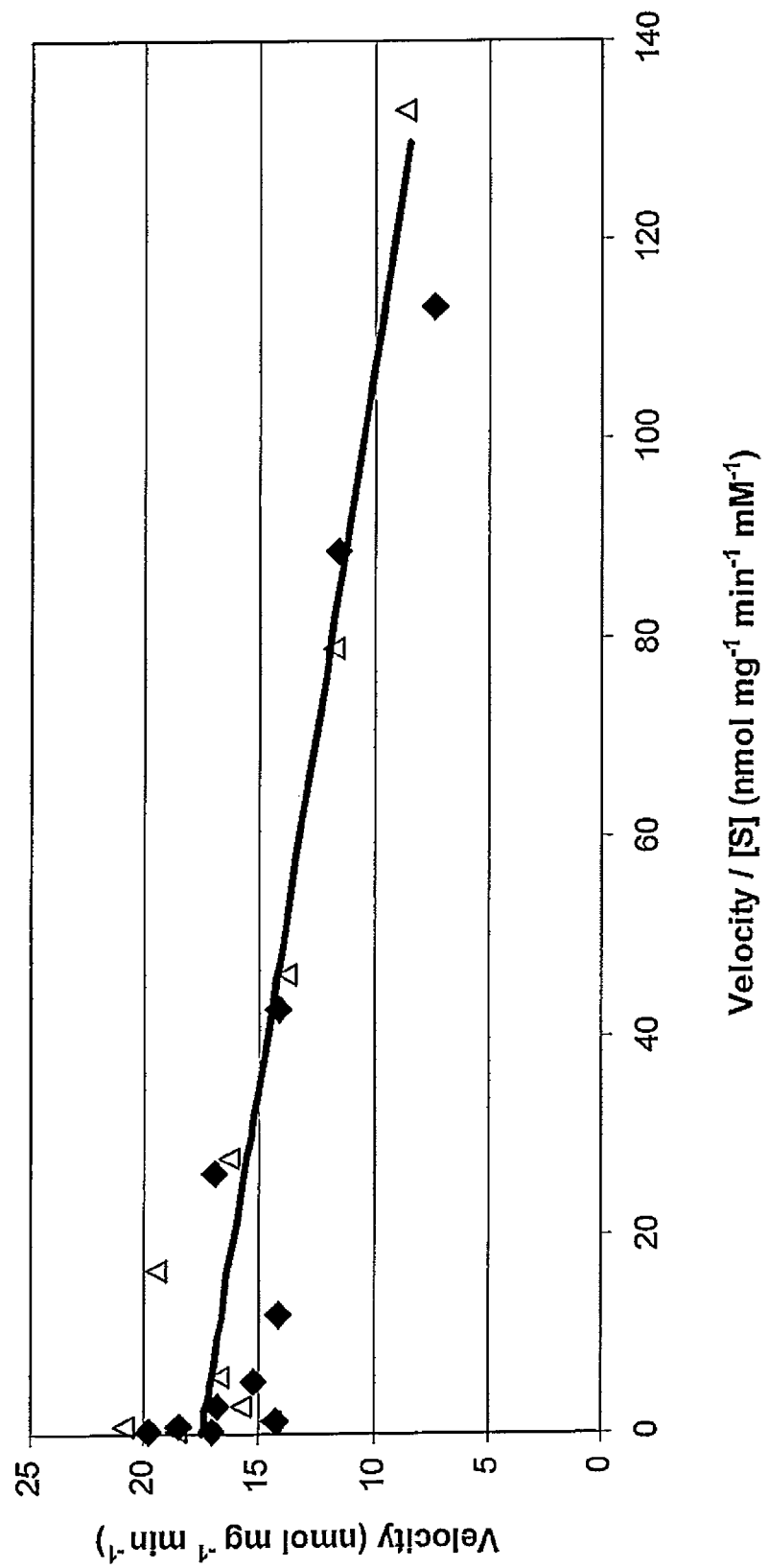
FIG. 10 shows the transport kinetics of L-arabinose by the PgLAT2 transporter expressed in *S. cerevisiae*. Open triangles indicate transport for wild type *P. guilliermondii* grown on L-arabinose. Black diamonds indicate transport for PgLAT2 expressed in *S. cerevisiae* grown on L-arabinose.

The L-arabinose transport characteristics of the PgLA 72 transporter expressed in *S. cerevisiae* grown on 0.2% L-arabinose medium showed the same L-arabinose transport characteristics as wildtype *P. guilliermondii* (FIG. 10). The PgLAT2 transporter when expressed in *S. cerevisiae* has a $K_m$=0.07 mM and $V_{Max}$=18 nmol/mg-min. Inhibition experiments showed significant inhibition of transport by protonophores ($NaN_3$, DNP, and CCP) and H+-adenosine triphosphatase (ATPase) inhibitors (DESB and DCCD) similar to the inhibition observed in wildtype *P. guilliermondii* (Table 7). Competition experiments showed that L-arabinose uptake by the PgLAT2 transporter was inhibited by glucose, galactose, xylose and to a lesser extent by maltose (Table 7).

TABLE 7

Effect of Inhibitors or Competing Sugars on the Rate of L-Arabinose Transport in L-Arabinose-Grown *P. guilliermondii* Y-2075 and *S. cerevisiae* BFY605

| Inhibitor or Competing Sugar | Concentration (mM) | Relative L-arabinose transport | |
|---|---|---|---|
| | | *P. guilliermondii* | *S. cerevisiae* (PgLAT2 transporter) |
| None[a] | — | 100 | 100 |
| $NaN_3$ | 10 | 1 | 16 |
| DNP | 5 | 0 | 4 |
| CCCP | 5 | 0 | 2 |
| DCCD | 5 | 22 | 36 |
| DESB | 5 | 8 | 1 |
| None[b] | — | 100 | 100 |
| Glucose | 120 | ND | 17 |
| Galactose | 120 | ND | 20 |
| Xylose | 120 | 4 | 0 |
| Maltose | 120 | ND | 30 |

[a]Rate of L-arabinose transport was 11.2 nmol mg$^{-1}$ min$^{-1}$ for *P. guilliermondii* and 10.4 nmol mg$^{-1}$ min$^{-1}$ for *S. cerevisiae* (PgLAT2 transporter) determined with 0.33 mM labeled L-arabinose.
[b]Rate of L-arabinose transport was 14.2 nmol mg$^{-1}$ min$^{-1}$ for *P. guilliermondii* and 14.4 nmol mg$^{-1}$ min$^{-1}$ for *S. cerevisiae* (PgLAT2 transporter) determined with 1.2 mM labeled L-arabinose.

The transport activities, inhibition profiles, and competition rates with respect to xylose of wildtype *P. guilliermondii* and of the PgLAT2 transporter expressed in *S. cerevisiae* are identical suggesting that *P. guilliermondii* has a single, high affinity, active transporter charged with uptake of L-arabinose. There are no L-arabinose transport activities that are unaccounted which suggests the presence of a single L-arabinose transporter in *P. guilliermondii*.

Example 8

Synergistic Effect on Growth Rate and Sugar Utilization by *S. cerevisiae* Expressing Gal2p and the New Transporter Proteins-PgLat2 and KmLat1

To determine the complementary effects on arabinose transport by the three transporters, namely, Gal2p, PgLat2 and KmLat1, yeast strains were constructed with appropriate selection markers to allow different pathway and transporter combinations to be expressed. All possible transporter combinations were generated by introducing transporter expression plasmids for PgLat2 and KmLat1 (or empty vectors) into *S. cerevisiae* strains expressing the bacterial genes araA, araB and araD (See e.g., Becker and Boles). All strains expressing Gal2p (due to the gal180Δ genotype), plus or minus other transporters, were able to grow on 2% or 0.2% L-arabinose after extensive lag times (a process termed "adaptation"). A relatively low concentration of L-arabinose (0.2%) was used in this experiment as strain differences are more pronounced at this concentration. Once "adapted" to growth on 0.2% L-arabinose, the strains were able to grow more quickly and growth curves for each transporter combination were generated.

FIG. 11 shows a comparison of shake flask growth curves for four strains on 0.2% L-arabinose, all of which express Gal2p (via the GAL80 deletion) in the absence or presence of the novel transporter PgLat2 (also see Table 5). A significant lag time was observed due to their inoculation from stationary cultures. However, once growth initiated, the growth rate was relatively rapid. The doubling time for each culture in the exponential phase of the curve is shown in Table 5. The doubling time for the PgLat2 and Gal2p co expressing cells was markedly shorter than in the cells expressing only Gal2p (15 hours vs. 19 hours). A second observation relates to the overall extent of growth. The PgLat2 expressing strain appeared to grow to a higher overall optical density at saturation, suggesting that this strain was able to utilize the carbon source (L-arabinose) in the medium more completely (FIG. 11).

Example 9

Co-expression of Gal2p with PgLAT2 or KmLAT1 Enables More Complete Utilization of Arabinose by Recombinant *S. cerevisiae*

Doubling times for the cultures described above in Example 8 were measured in early exponential phase for each culture. Doubling time was measured by the period of time taken for the number of cells to double in a given cell culture (See generally, Guthirie and Fink, 1991). The concentration of remaining L-arabinose at the 276 hour time point was determined by HPLC (for saturated cultures only). The concentration of L-arabinose in the starting media was about 1.89 and the concentration of L-arabinose in media without L-arabinose had an undetectable level (<0.1 g/L). As shown in Table 5, significantly less residual L-arabinose remained in the culture of cells expressing both Gal2p and PgLAat2 than in the culture of cells expressing Gal2p alone.

Example 10

Construction of *S. cerevisiae* Strain Deficient in Aldose Reductase (AR)

Based on the sequence of a presumptive AR gene, two oligonucleotide primers were designed and the AR gene along with 600 bp of flanking DNA were cloned by PCR using genomic DNA isolated from yeast as template. Using another set of primers, an AR deletion construct was made in which all the coding sequences of the AR gene were replaced with a restriction enzyme site (SalI). The yeast LEU2 gene was isolated as a SalI-XhoI fragment and cloned into the SalI site of the AR deletion construct. The DNA fragment containing the LEU2 gene and AR flanking sequences was Used to transform the leu2⁻ yeast strain BFY001. LEU⁺ transformants were isolated, grown and analyzed by Southern and PCR analysis to confirm that the AR gene in the gnome had been deleted and replaced with the LEU2 gene by homologous recombination.

One such transformant, designated BFY002, was chosen as a host for further construction of arabinose fermenting yeast strains. Shake-flask experiments were conducted and the results showed that arabitol formation in BFY002 had been reduced to about 50% in comparison with the parental strain BFY001.

Figure 12A:
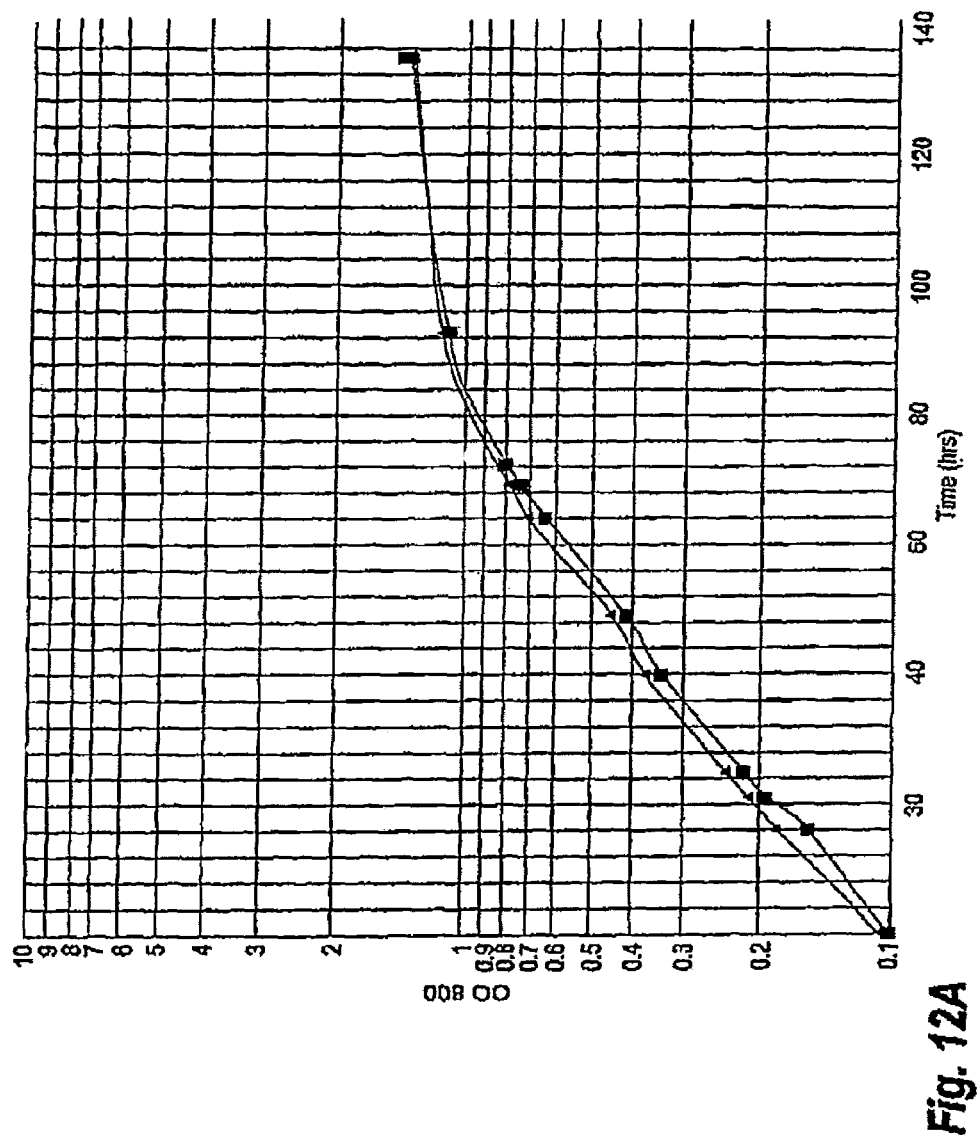
FIG. 12 shows the growth curves of BFY001 (parent) (black square) and BFY002 (ΔAR) (black triangle) on glucose and xylulose.
Figure 12B:
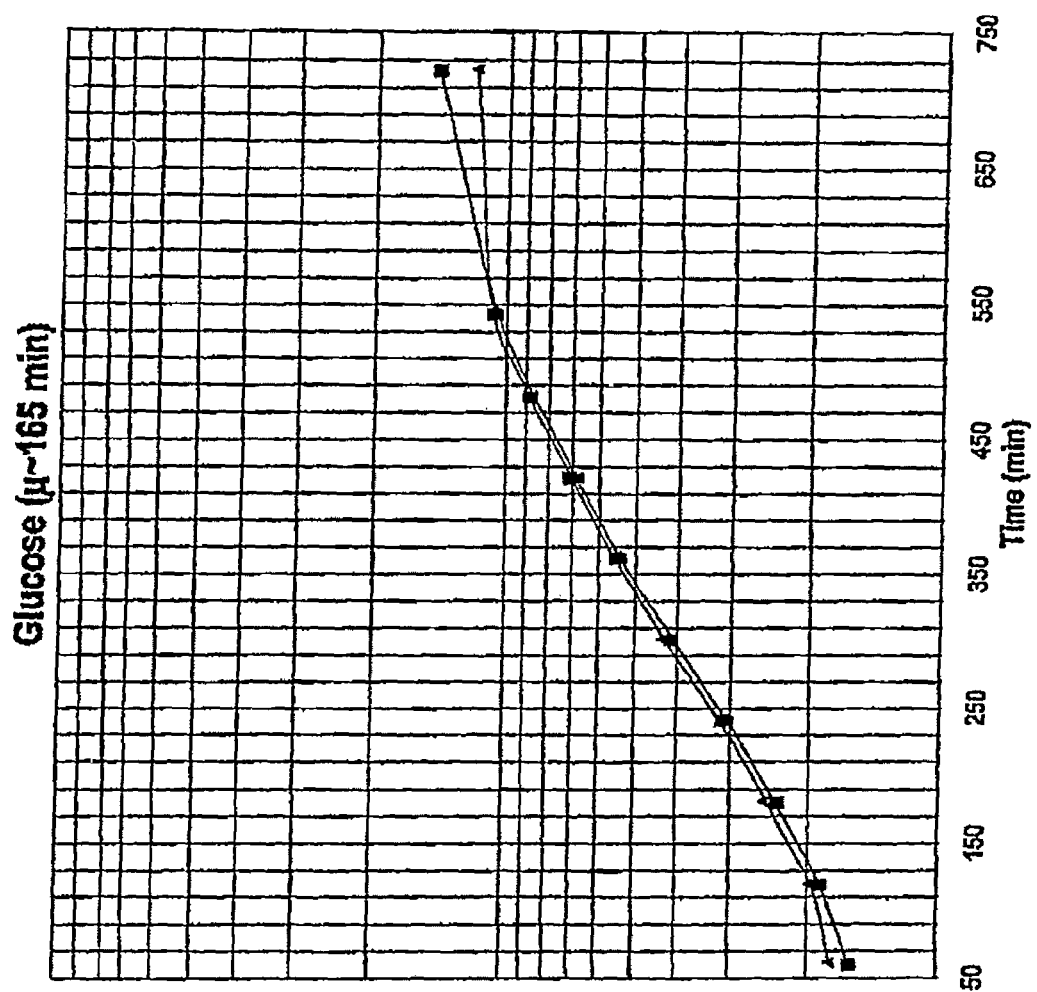

Growth of BFY002 on glucose and xylulose was compared with that of BFY001. Briefly, yeast strains BPY001 and BFY002 were grown in rich medium YPD. Cells were collected by centrifugation and washed with sterile water. The Washed cells Were suspended in water at the original density. 50 μl of this cell suspension was used to inoculate 5 ml of medium containing yeast nitrogen base ("YNB") supplemented with leucine ("Leu"), tryptophan ("Trp"), histidine ("Ms") and uracil ("Ura"), plus with 1% glucose or 1% xylulose. The growth of each strain on both media at 30° C. with shaking was monitored by measuring the $OD_{600}$ for about 6 generation times. As expected, both strains had much shorter doubling time on glucose than on xylulose. No significant difference in the growth curves was observed between BFY001 and BFY002 regardless of whether glucose or xylulose was used (FIG. 12).

Example 11

Isolation of *E. coli* araBAD Genes and *B. subtilis* araA and Introduction into *S. cerevisiae*

Primers were designed to isolate *E. coli* araA gene as a BglII fragment, and the araB and araD genes were isolated as BamHI fragments by PCR from plasmid pZB206. The fragments containing the three genes were cloned into a yeast expression vector pBFY004, which contains PGK promoter, GAL10 terminator, and TRP1 selection marker. Each plasmid carrying individual gene was then transformed into the yeast strain BFY002 in separate experiments. Transformants carrying individual plasmid were analyzed for the expression levels of each ara protein. L-ribulokinase (araB) and L-ribulose-5-P-4-epimerase (araD) were expressed at a higher level while L-arabinose isomerase (araA) was expressed at a lower level.

In order to introduce all three ara genes into the same cell, URA3 and HIS3 expression vectors for each ara gene were constructed by re-engineering the TRP1 plasmid, pBFY004. Briefly, the TRP1 coding sequence was removed and replaced with a SalI restriction site to generate a plasmid designated as pBFY011. Other selection markers, HIS3 or URA3, were then cloned into this plasmid. Another strategy for introducing all three ara genes into the same cell was to construct a plasmid carrying all three genes. Briefly this was done by combining each ara gene with a different promoter/terminator combination to prevent homologus recombination and thus loop-out of the genes with consequential loss of function. Primers were designed to clone the *E. coli* araD gene between the THD3 promoter and GAL2 terminator. This expression cassette was then moved to pBFY007 (which already has the E. coli araA gene cloned between the PGK1 promoter and GAL10 terminator) and designated pBFY051. Similarly primers were designed to clone the E. coli araB gene between the PGII promoter and the PDC1 terminator. This expression cassette was then moved to pBFY051 to create pBFY090 which now has all three E. coli ara genes. The B. subtilis araA gene was then isolated using PCR and cloned between the PGK1 promoter and GAL 10 terminator to replace the E. coli araA. The URA3 gene was isolated as a SalI fragment and cloned into the SalI site to construct the plasmid pBFY012. Similarly, a HIS3 expression vector) pBFY013, was constructed by engineering and cloning the HIS3 gene into pBFY011.

Figures 13A, 13B:
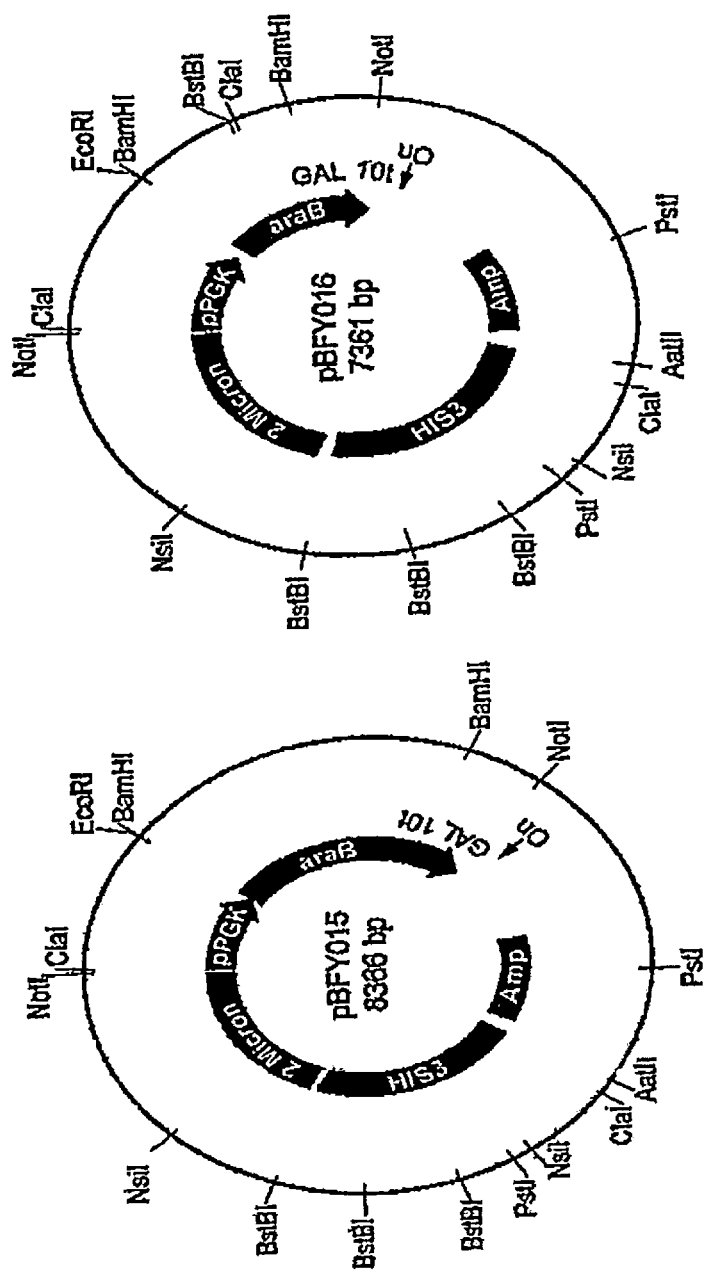
FIG. 13 shows the diagrams of the expression plasmids with araB, araA, and araD genes carrying the His3 selectable marker.
Figure 13C:
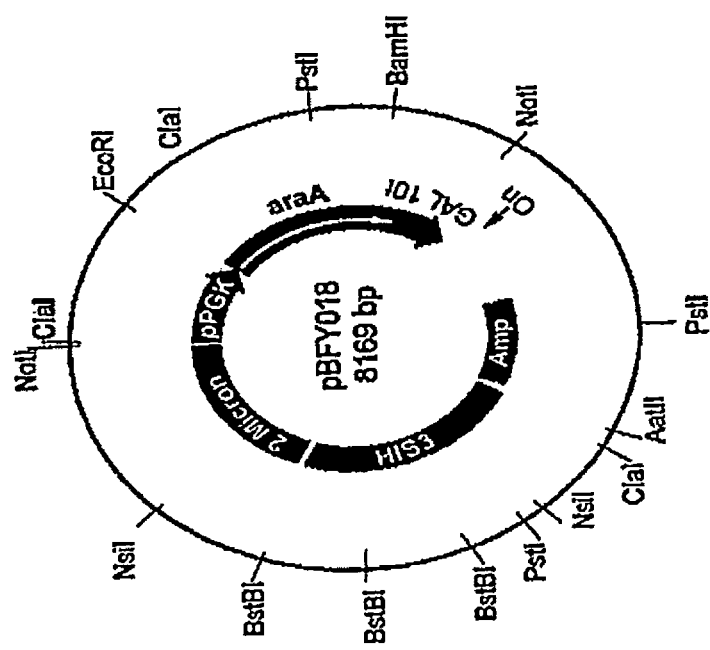
Figures 14A, 14B:
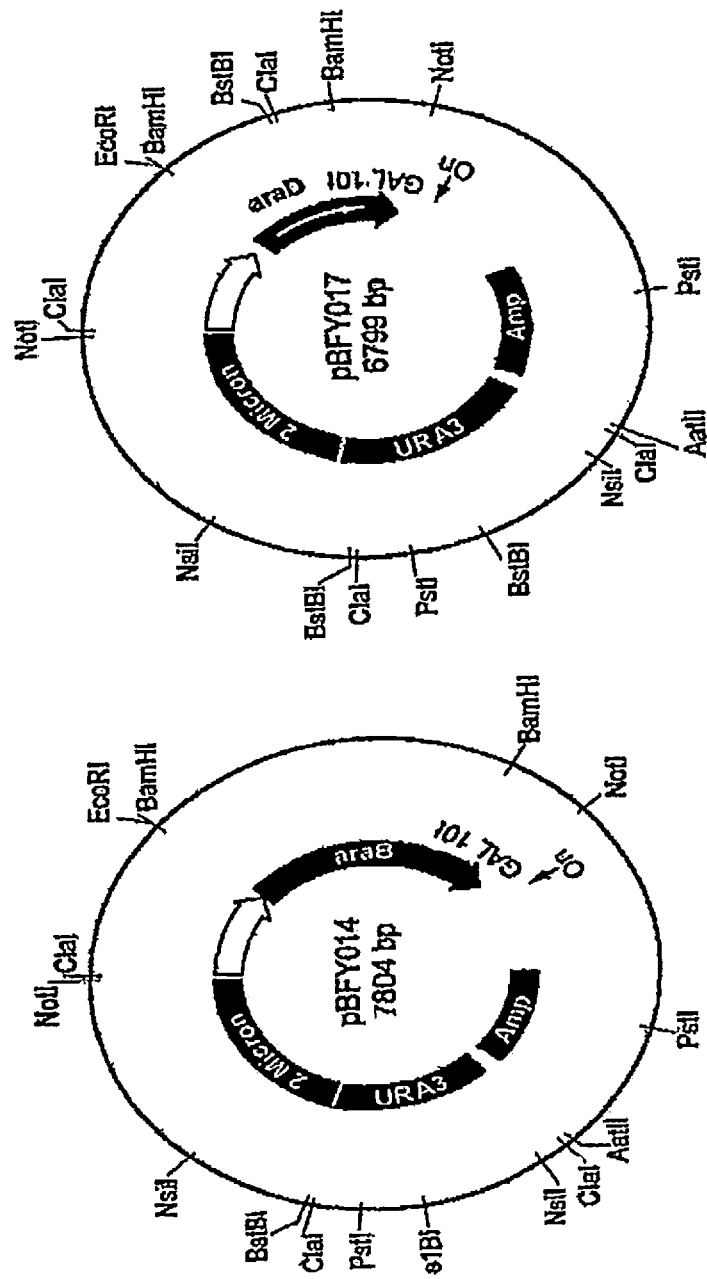
FIG. 14 shows the diagrams of the expression plasmids with araB, araA, and araD genes carrying the Ura3 selectable marker.
Figure 14C:
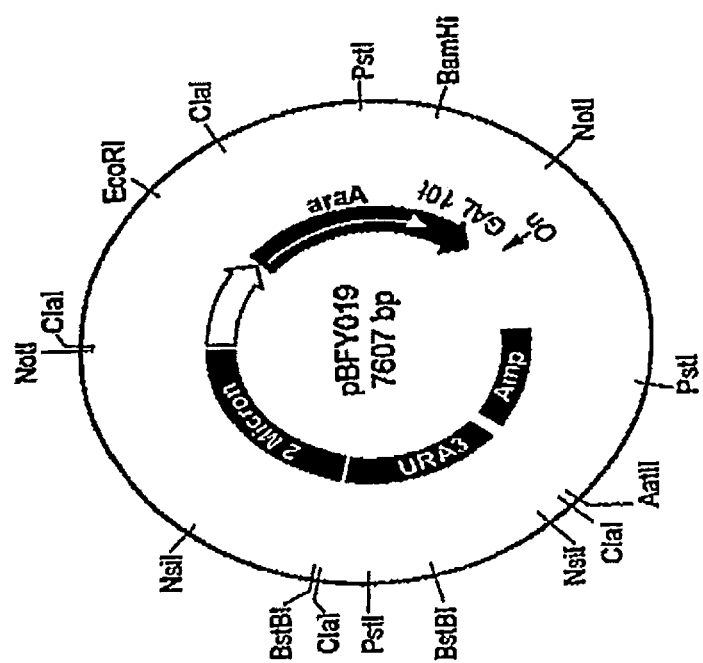

The engineered ara genes were cloned into each of these expression vectors to generate a series of expression vectors carrying each of the araBAD genes with either Trp1, Ura3 or His3 markers (Table 3; also see FIG. 13 and FIG. 14). Appropriate combinations of these expression vectors were introduced into the strain BFY002. Similarly, the plasmid containing all three ara genes was introduced into the strain BFY057. The transformants were characterized and assayed for growth and fermentation of arabinose.

plasmids present in the original yeast cells was estimated based on the number of E. coli transformants harboring each plasmid (Table 8).

TABLE 8

| Ratio of the 3 plasmids in BFY013 | |
|---|---|
| ara gene | Number |
| araB | 11 |
| araA | 4 |
| araD | 15 |

Example 13

Assays of Enzymatic Activities of araBAD Proteins Expressed in S. cerevisiae

The activities of the three E. coli enzymes heterologously expressed in S. cerevisiae were measured in the crude extracts of the yeast transformants according to protocol described in Becker and Boles, 2003. The results of these assays are summarized in Table 9. Table 10 compares the enzymatic activities of the two strains used for subsequent fermentation. The enzymatic assays were performed in the presence of absence of 20 mM $MnCl_2$, but it appears that $MnCl_2$ does not have significant effect on the overall results (Table 10).

TABLE 9

| Enzyme activities in transformants carrying all 3 ara genes | | | | | | | | |
|---|---|---|---|---|---|---|---|---|
| | L-arabinose isomerase (araA) Sp. act μmol/min/mg | | | L-ribulokinase (araB) Sp. act μmol/min/mg | | L-ribulose-5-P4-epimerase (araD) Sp. act μmol/min/mg | | |
| Strain | Oct 20-21 (1) | Oct 20-21 (2) | Dec 20-22 (2) | Oct 20-21 | Dec 20-22 | Oct 20-21 | Dec 20-22 | |
| BFY012 | nd | | | nd | | nd | nd | |
| BFY013 | 0.05 | 0.10 | 0.11 trp | 1.2 | 1.3 ura | 0.5 | 1.0 | his |
| BFY014 | 0.04 | 0.11 | 0.11 trp | 1.2 | 1.9 his | nd | nd | ura |
| BFY015 | nd | | nd ura | 2.4 | 2.8 trp | 0.39 | 0.9 | his |
| BFY016 | 0.03 | | 0.06 his | 2.4 | 2.4 trp | nd | nd | ura |
| BFY017 | 0.02 | | nd his | 0.9 | 1.1 ura | 1.56 | >3.5 | trp |
| BFY018 | 0.01 | | nd ura | 1.2 | 1.0 his | 1.12 | >2.2 | trp |
| Zymomonas | 0.85 | | | 0.9 | | 1.9 | | | nd = not detected
(1) = cysteine-carbazole
(2) = new method, NADH disappearance
All cultures were grown in selective medium (YNB +2% glc-trp-his-ura)

Example 12

Determination of the Copy Numbers of Plasmids Carrying araBAD in S. cerevisiae

The copy numbers of the three plasmids present in the strain BFY013 (Table 8) transformed as described in Example 11 were determined. On colony of BFY013 was isolated and used to inoculate a flask with yeast minimum medium. The cells were allowed to grown to exponential phase and the cells were harvested by centrifugation. Spheroplasts of the cells were prepared and DNA was extracted from these spheroplasts (See Guthrie and Fink, 1991). E. coli strain DH5α cells were then transformed with the extracted yeast DNA. Bacterial transformants were plated out and plasmid DNA in individual colonies was isolated and characterized by restriction digest followed by agarose gel electrophoresis. Assuming that the individual plasmids carrying each of the araBAD genes possessed the same capability to transform bacterial cells, the ratio between the copy numbers of each

TABLE 10

| Enzyme Activities in Strains Used for Fermentation | | | | | |
|---|---|---|---|---|---|
| Strain | $MnCl_2$ (20 mM) | Protein mg/ml | Isomerase (araA) Sp. act umol/min/mg | Kinase (araB) Sp. act umol/min/mg | Epimerase (araD) Sp. act umol/min/mg |
| BFY012 | No | 6.6 | nd | nd | nd |
| BFY012 | Yes | 6.1 | nd | nd | nd |
| BFY013 | No | 7.0 | 0.09 | 2.2 | 0.6 |
| BFY013 | Yes | 6.7 | 0.09 | 1.9 | 0.5 |

Example 14

Whole-Cell Fermentation in S. cerevisiae

Figure 15:
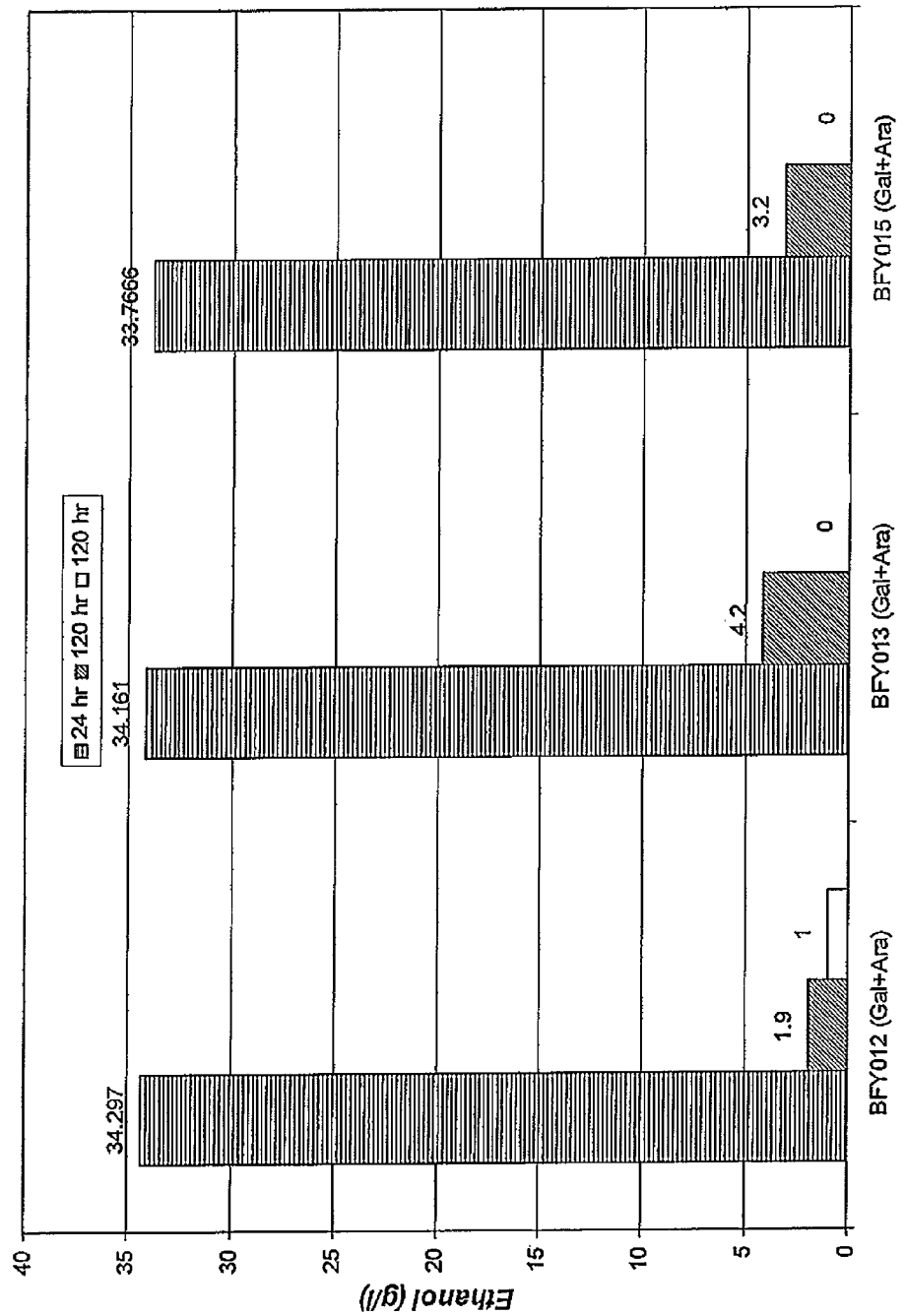
FIG. 15 shows histogram With the result of ethanol production in whole-cell fermentation using yeast cells expressing the three bacterial genes araB, araA, and araD.

The transformed yeast cells carrying bacterial genes araBAD were first grown in galactose or arabinose alone or in the presence of both galactose and arabinose in YNB. Cells were collected by centrifugation and washed in water. The washed cells were resuspended in liquid media containing 1% yeast extract and 2% peptone (YP). The cell suspensions were aliquoted into various tubes before appropriate sugars were added. The tubes were incubated at 30° C. and cell samples were taken at the time indicated. The samples were filtered and analyzed for ethanol concentration by gas chromatography (GC) according to Tietz, 1976 (Table 11 and FIG. 15) or by high performance liquid chromatography (HPLC). As shown in Table 11, cells that were grown in both galactose and arabinose immediately before the fermentation assay had a slightly higher overall yield of ethanol than cells grown in galactose alone during the same period. The strains BFY534 and BFY535 were grown in arabinose alone prior to fermentation. From a starting concentration of 19 g/L of L-arabinose, BFY534 and BFY535 used 12.7 and 11.8 g/L of L-arabinose to yield 4.7 and 4.9 g/L of ethanol in 48 hours respectively. The percentage of maximum theoretical conversion would thus be 75% and 78% respectively and a productivity of 0.012 EtOH/g cells hr for both strains. In an additional fermentation with strain BFY534 performed in shake flasks, 19.7 g/L of L-arabinose was converted to 8.5 g/L ethanol in 96 hrs giving 85% of the theoretical maximum conversion and a productivity of 0.017 g EtOH/g cells hr.

TABLE 11

Ethanol Concentration (g/l) from Whole Cell Fermentation

| Time (hrs) | Glucose (66.7 g/l) | | Arabinose (66.7 g/l) | | | No sugar | | |
|---|---|---|---|---|---|---|---|---|
| | 0 | 24 | 0 | 24 | 120 | 0 | 24 | 120 |
| BFY012 (Gal) | 1.9 | 33.6 | 1.0 | 1.1 | 1.8 | 1.0 | 0.9 | 1.8 |
| BFY013 (Gal) | 1.6 | 33.3 | 0.9 | 1.3 | 2.6 | 0.0 | 0.9 | 0 |
| BFY015 (Gal) | 1.5 | 33.8 | 0.9 | 1.3 | 2.5 | 0.0 | 0.9 | 1.3 |
| BFY012 (G + A) | 2.1 | 34.3 | 1.0 | 1.2 | 1.9 | 1.0 | 1.0 | 1 |
| BFY013 (G + A) | 1.7 | 34.2 | 1.0 | 1.8 | 4.2 | 0.9 | 1.0 | 0 |
| BFY015 (G + A) | 1.5 | 33.8 | 0.0 | 1.5 | 3.2 | 0.0 | 1.0 | 0 |

Example 15

Cell-Free Fermentation in *S. cerevisiae*

Figure 17:
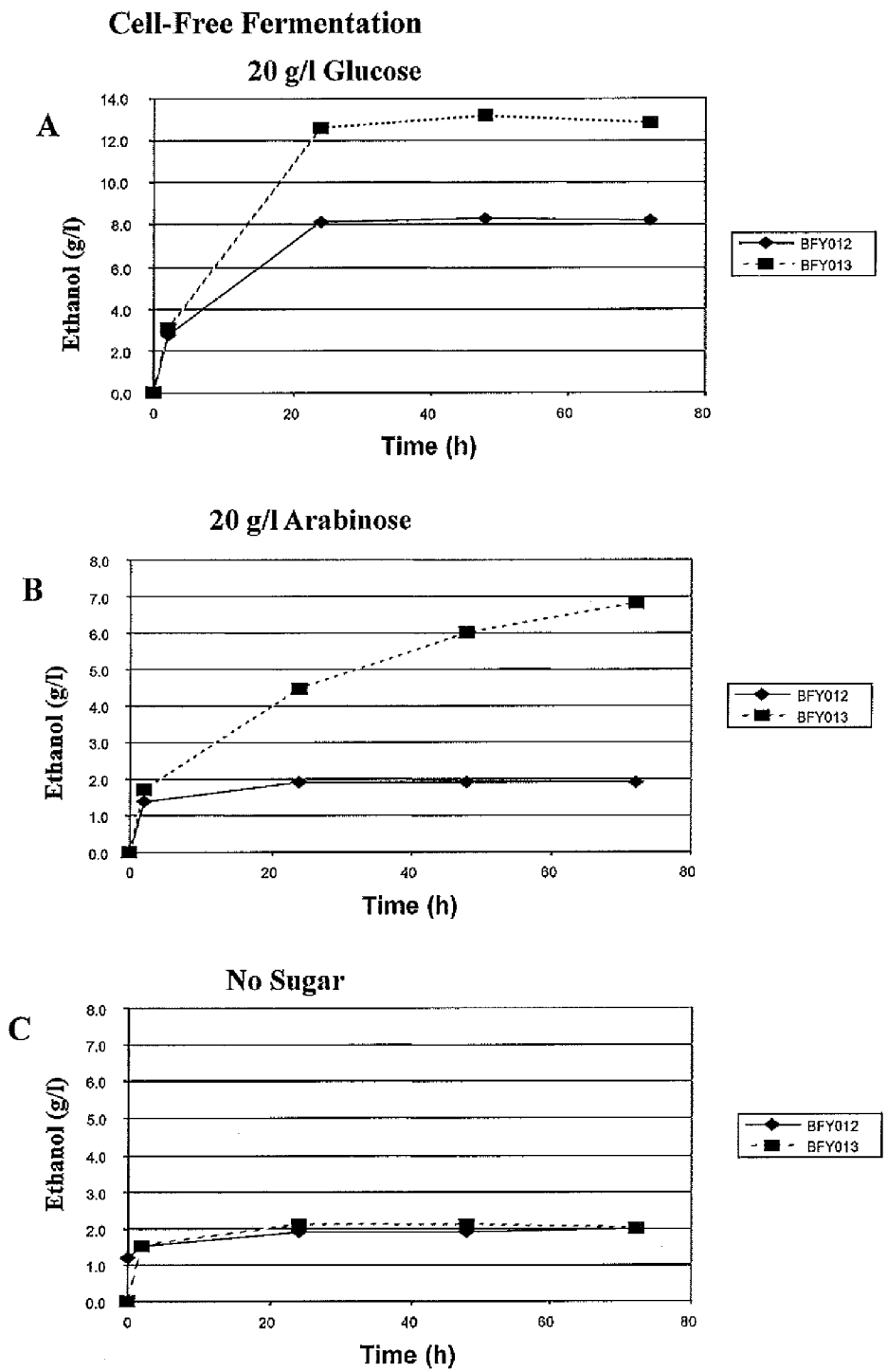
FIG. 17 plots ethanol production using yeast cells expressing the three bacterial genes araB, araA, and araD, as a function of the incubation time in a cell-free fermentation system.
Figure 18:
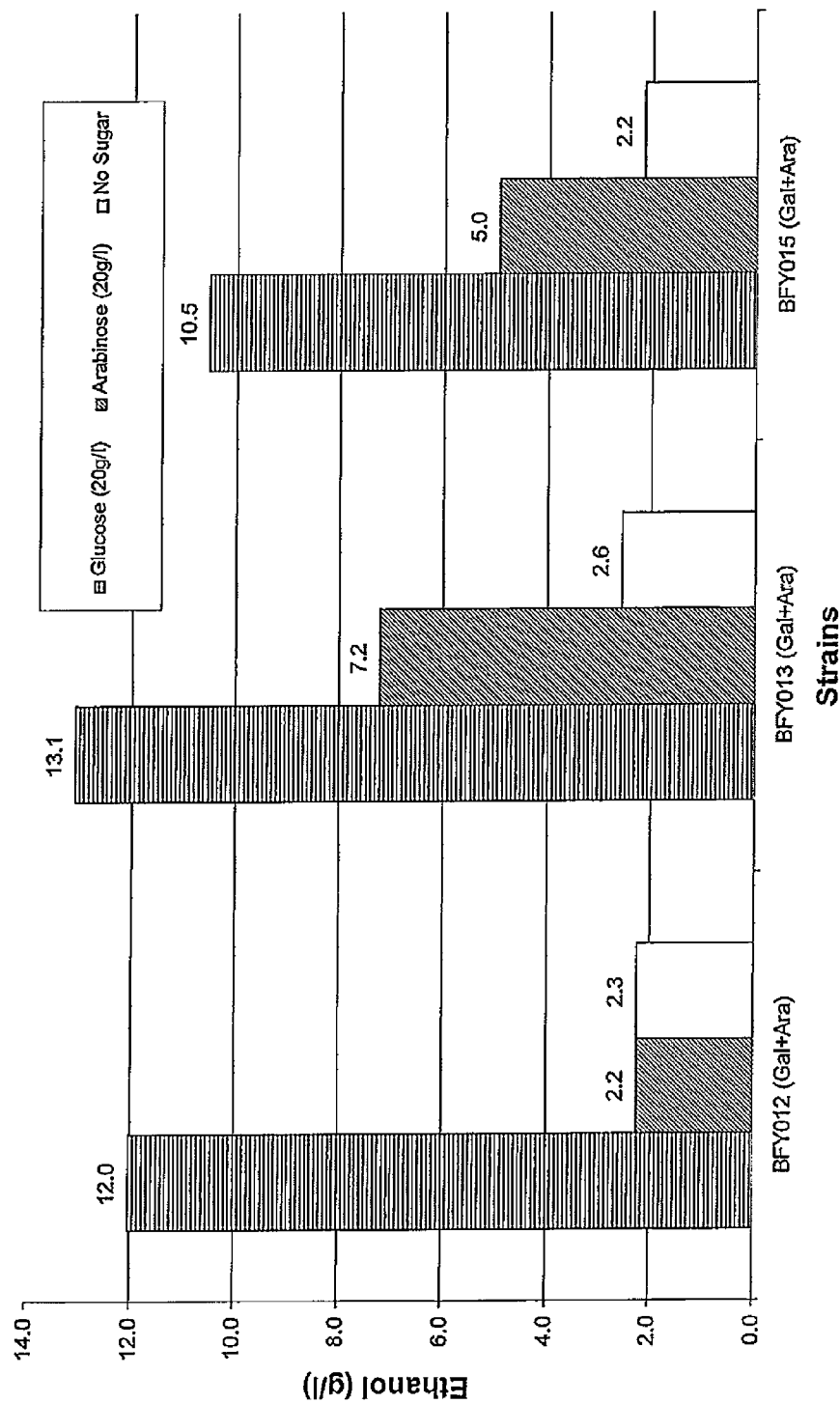
FIG. 18 shows histogram with the result of ethanol production in cell-free fermentation using yeast cells expressing the three bacterial genes araB, araA, and araD.

For fermentation of arabinose in a cell-free system, yeast transformants were grown in the presence of both galactose and arabinose in YNB. Cells were collected by centrifugation and washed in water. Cell walls were removed by enzymatic digestion and the cells were then lysed in a lysis buffer containing 20 mM potassium phosphate buffer, pH 7 and 10 mM MgCl$_2$ and 1 mM DTT. Cells debris were removed by centrifugation, and the supernatant was transferred to a tube where various chemicals were added to the supernatant such that the fermentation mix contained 7 mM Mg acetate, 5 mM ATP, 0.1 mM diphosphoglyceric acid, 4 mM Na arsenate and 2 mM NAD$^+$. Fermentation was started by adding appropriate sugar to the fermentation mix in the tube. The tube was incubated at 30° C., and samples were taken at the time indicated. The samples were boiled, centrifuged, filtered and analyzed for ethanol concentration by gas chromatography (GC) as previously described. Results of the cell-free fermentation are shown in Table 12, FIG. 16, FIG. 17 and FIG. 18.

TABLE 12

Ethanol Concentration (g/l) from Cell-Free Fermentation

| | Glucose | | | | | Arabinose | | | | | No sugar | | | | |
|---|---|---|---|---|---|---|---|---|---|---|---|---|---|---|---|
| Time (hrs) | 0 | 2 | 24 | 48 | 72 | 0 | 2 | 24 | 48 | 72 | 0 | 2 | 24 | 48 | 72 |
| BFY012 | 0.0 | 2.7 | 8.1 | 8.3 | 8.2 | 0.0 | 1.4 | 1.9 | 1.9 | 1.9 | 1.2 | 1.5 | 1.9 | 1.9 | 2.0 |
| BFY013 | 0.0 | 3.1 | 12.6 | 13.2 | 12.8 | 0.0 | 1.7 | 4.5 | 6.0 | 6.8 | 0.0 | 1.5 | 2.1 | 2.1 | 2.0 |
| BFY012 (20 mM MnCl$_2$) | 1.3 | 2.6 | 9.2 | 9.0 | 8.5 | 1.2 | 1.4 | 1.9 | 1.9 | 2.1 | 0.0 | 1.4 | 2.0 | 2.0 | 1.8 |
| BFY013 (20 mM MnCl$_2$) | 1.3 | 3.0 | 12.8 | 13.1 | — | 1.3 | 1.8 | 4.6 | 6.1 | 6.8 | 1.3 | 1.6 | 2.0 | 2.0 | — |

Example 16

Mixed-Sugar Fermentation in *S. cerevisiae*

Yeast strains adapted to contain the araB and araD genes from *E. coli*, the araA isomerase gene from *B. subtilis*, and the GAL2 overexpression plasmid have been described previously (see for example, Example 11). Adapted strains, BFY534 for example, were tested for fermentation of glucose, arabinose, and a mixture of arabinose and glucose. In particular, 125 ml non-baffled flasks containing 50 ml of yeast-extract-peptone media (including adapted yeast) and either no sugar, glucose, L-arabinose, or both glucose and L-arabinose were prepared. The flasks were closed with Saranwrap held in place with rubber bands. The fermentations were performed at 30° C. with gentle shaking (80 rpm). In all cases, each sugar was present at a concentration of 20 g/L.

Figure 19:
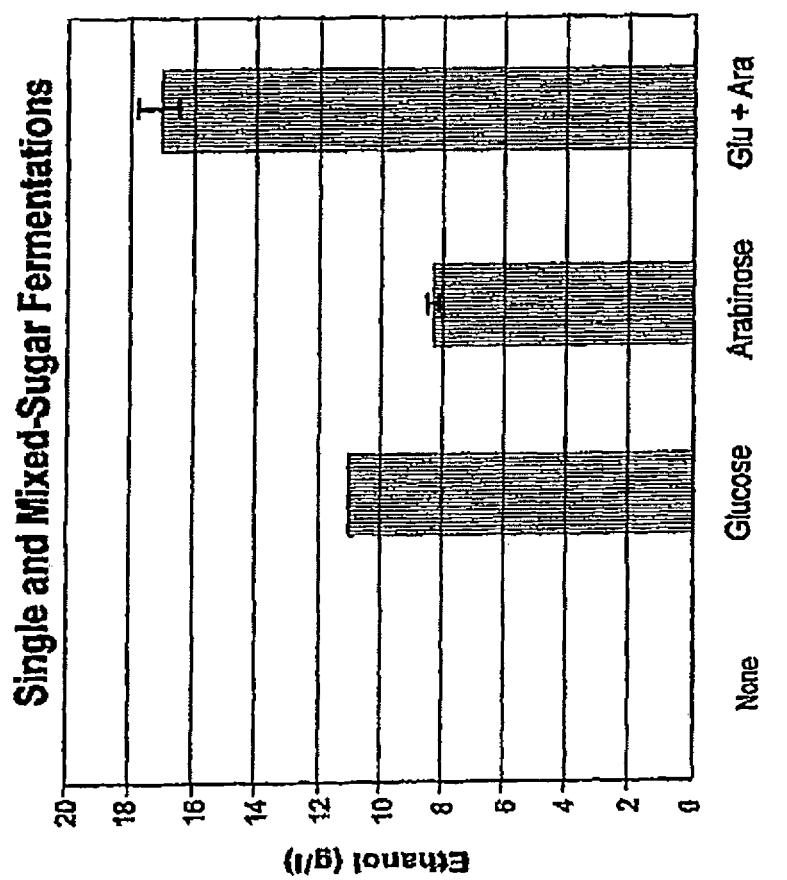
FIG. 19 plots ethanol production using yeast cells expressing the three bacterial genes araB, araA, and araD, under single- and mixed-sugar fermentations.

The results are illustrated in FIG. 19, where a greater than 50% increase in ethanol production was obtained in co-fermentation of glucose and L-arabinose, compared to the ethanol yield of glucose alone.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

This specification contains numerous citations to references such as patents, patent applications, and scientific publications. Each is hereby incorporated by reference for all purposes.

LIST OF REFERENCES CITED

Alves-Araujo, C., M. Hernandez-Lopez, M. Sousa, J. Prieto, and F. Randez-Gil. 2004. Cloning and characterization of the MAL11 gene encoding a high-affinity maltose transporter from *Torulaspora delbrueckii*. FEMS Yeast Research 4:467-476.

Arnold, F. H. Nature Biotechnol, 1998, 16, 617-618.

Barnett, J. A. 1976, The utilization of sugars by yeasts; Adv. Carhohydr. Chem. Biochem. 32:125-234.

Bowie et al., 1990, Science 247:130640.
Cosman et. al., 2001 Immunity 14:123-33.
Crameri A. et al., 1998, Nature 391: 288-91.
Day, R., V. Higgins, P. Rogers, and I. Dawes. 2002. Characterization of the putative maltose transporters encoded by YDL247w and YJR160c. Yeast 19:1015-1027.
Deanda, K., M. Zhang, C. Eddy, and S. Picataggio. 1996. Development of an arabinose-fermenting *Zymomonas mobilis* strain, by metabolic pathway engineering. Appl. Environ. Microbiol. 62:4465-4470.
Dujon B. S. D., Fischer G, Durrens P, Casaregola S, Lafontaine I, De Montigny J, Marck C, Neuveglise C, Talla E, Goffard N, Frangeul L, Aigle M, Anthouard V, Babour A, Barbe V, Barnay S, Blanchin S, Beckerich J M, Beyne E, Bleykasten C, Boisrame A, Boyer J, Cattolico L, Confanioleri F, De Daruvar A, Despons L, Fabre E, Fairhead C, Ferry-Dumazet H, Groppi A, Hantraye F, Hennequin C, Jauniaux N, Joyet P, Kachouri B, Kerrest A, Koszul R, Lemaire M, Lesur I, Ma L, Muller H, Nicaud J M, Nikolski M, Oztas S, Ozier-Kalogeropoulos O, Pellenz S, Potter S, Richard G F, Straub M L, Sulenu A, Swennen D, Tekaia F, Wesolowski-Louvel M, Westhof E, Wirth B, Zeniou-Meyer M, Zivanovic I, Bolotin-Fukuhara M, Thierry A, Bouchier C, Caudron B, Scarpelli C, Gaillardin C, Weissenbach J, Wincker P, Souciet J L. 2004, Genome evolution in yeasts. Nature 430:35-44.
Guthrie, C., and G. R. Fink, eds. 1991. Guide to Yeast Genetics and Molecular Biology. Methods in Enzymology, Vol. 194, Academic Press.
Hellinga, H. W. Nature Structural. Biol. 1998, 5, 525-7.
Hespell, R. B. 1998. Extraction and characterization of hemicellulose from the corn fiber produced by corn wet-milling processes. J. Agric. Food Chem. 46:2615-2619.
Hill, J., K. Ian, G. Donald, and D. Griffiths, 1991. DMSO-enhanced whole cell yeast transformation. Nucleic Acids Research 19:5791.
Hofmann, K., and S. W. 1993. A database of membrane spanning proteins segments. Biol. Chem. 374:166.
Kötter, P., R. Amore, C. P, Hollenberg, and M. Ciriacy. 1990, Isolation and characterization of the *Pichia stipitis* xylitol dehydrogenase gene, XYL2, and construction of a xylose-utilizing *Saccaromyces cerevisiae* transformant. Curr. Genet. 18:493-500.
Kruckeberg, A. 1996. The hexose transporter family of *Saccharomyces cerevisiae*. Arch. Microbiol. 166:283-292.
Landschultz et al., 1988, *Science,* 240:1759,
Luckow and Summers, 1988 *Bio/Technology* 6:47.
McMillan, J. D., and B. L. Boynton. 1994. Arabinose utilization by xylose-fermenting yeasts and fungi. Appl. Biochem. Biotechnol. 45-46:569-584.
Pina, C., P. Goncalves, C. Prista, and M. Loureiro-Dias. 2004. Ffz1, a new transporter specific for fructose front *Zygosaccharomyces bailil*. Microbiol 150:2429-2433.
Saltou, N., and M. Nei. 1987 The neighbor-joining method: a new method for reconstructing phylogenetic trees. Mol Biol Evol July; 4(4):406-25.
Sambrook, J., E. Fritsch, and T. Maniatis. 1989. Molecular Cloning: a Laboratory Manual, 2nd. ed. Cold Spring Harbor Laboratory Press, NY.
Sedlak, M., and N. W. Ho, 2001. Expression of *E. coli* araBAD operon encoding enzymes for metabolizing L-arabinose in *Saccharomyces cerervisiae*. Enzyme Microb. Technol. 28:16-24.
Stambuk, B., M. Franden, A. Singh, and M. Zhang. 2003. D-Xylose transport by *Candida succiphila* and *Kluyveromyces marxianus*. Appl Biochem Biotechnol 105-108: 255-263.
Tietz, Norbert W., ed. "Determination of Alcohols by Gas Chromatography." *Fundamentals of Clinical Chemistry*. Saunders Company: Philadelphia, 1976, pp. 1110-1111.
Van den Burg, B.; Vriend, G.; Veltman, O. R.; Venema, G.; Eijsink, V. G. H. 1998. Engineering an enzyme to resist boiling. Proc. Nat. Acad. Sci. U.S., 95:2056-60.
Wahlbom, C. F., and B. Hahn-Hägerdal, 2002, Furfural, 5-hydroxymethyl furfural, and acetoin act as external electron acceptors during anaerobic fermentation of xylose in recombinant *Saccharomyces cerevisiae*. Biotechnol. Bioeng. 78:172-178.
Weierstall, T., C. Hollenberg, and E. Boles. 1999. Cloning and characterization of three genes (SUTI-3) encoding glucose transporters of the yeast *Pichia stipitis*, Mol Microbiol 31:871-883.
Zhang, M., C. Eddy, K. Deanda, M. Finkelstein, and S. Picataggio. 1995. Metabolic engineering of a pentose metabolism pathway in ethanologenic *Zymomonas mobilis*. Science 267:240-243.
Zhao, H.; Giver, L.; Shao, Z.; Affholter, J. A.; Arnold, F. H. Nature Biotechnol, 1998, 16, 258-62.

---

We claim:

1. An ethanol producing yeast strain, comprising at least one heterologous polynucleotide encoding a yeast arabinose transporter that comprises an amino acid sequence at least 95% identical to SEQ ID NO:2 or SEQ ID NO:4, wherein the yeast strain is capable of growth and ethanol production utilizing arabinose as a carbon source.

2. The ethanol producing yeast strain of claim 1, wherein the yeast arabinose transporter comprises the amino acid sequence of SEQ ID NO:2 or SEQ ID NO:4.

3. The ethanol producing yeast strain of claim 1, wherein the ethanol producing yeast strain is aldose reductase (AR) deficient (AR⁻).

4. The ethanol producing yeast strain of claim 1, wherein the ethanol producing yeast strain overexpresses a GAL2-encoded galactose permease.

5. The ethanol producing yeast strain of claim 1, wherein the yeast strain is from the genus *Saccharomyces*.

6. The ethanol producing yeast strain of claim 5, wherein the yeast strain is *Saccharomyces cerevisiae*.

7. The ethanol producing yeast strain of claim 1, further comprising one or more bacterial genes that facilitate arabinose utilization and fermentation in the ethanol producing yeast strain.

8. The ethanol producing yeast strain of claim 7, wherein the one or more bacterial genes that facilitate arabinose utilization and fermentation are selected from the group consisting of araA, araB and araD.

9. The ethanol producing yeast strain of claim 8, comprising araA, araB and araD.

10. The ethanol producing yeast strain of claim 1, wherein the yeast strain is strain BFY013, BFY534, BFY598 or BFY626.

* * * * *